US008673943B2

(12) United States Patent
Tam et al.

(10) Patent No.: US 8,673,943 B2
(45) Date of Patent: Mar. 18, 2014

(54) FLUORINATED DERIVATIVES OF DEFERIPRONE

(75) Inventors: Tim Fat Tam, Vaughan (CA); Regis Leung-Toung, Mississauga (CA); Yingsheng Wang, Toronto (CA); Yanqing Zhao, Toronto (CA)

(73) Assignee: Apotex Technologies Inc., Toronto, Ontario (CA)

( * ) Notice: Subject to any disclaimer, the term of this patent is extended or adjusted under 35 U.S.C. 154(b) by 368 days.

(21) Appl. No.: 13/245,262

(22) Filed: Sep. 26, 2011

(65) Prior Publication Data

US 2012/0095061 A1 Apr. 19, 2012

Related U.S. Application Data

(62) Division of application No. 12/078,079, filed on Mar. 27, 2008, now Pat. No. 8,026,261.

(60) Provisional application No. 60/907,290, filed on Mar. 28, 2007.

(51) Int. Cl.
*C07D 213/69* (2006.01)
*A61K 31/44* (2006.01)

(52) U.S. Cl.
USPC ............ 514/348; 514/460; 546/296; 549/418

(58) Field of Classification Search
None
See application file for complete search history.

(56) References Cited

U.S. PATENT DOCUMENTS

| 2,918,402 | A | 12/1959 | Fredrick |
|---|---|---|---|
| RE25,831 | E | 8/1965 | Moore |
| 4,585,780 | A | 4/1986 | Hider et al. |
| 5,154,926 | A | 10/1992 | Kawasaki et al. |
| RE34,313 | E | 7/1993 | Hider et al. |
| 5,616,621 | A | 4/1997 | Popli et al. |
| 5,658,919 | A | 8/1997 | Ratnaraj et al. |
| 5,730,997 | A | 3/1998 | Lienhop et al. |
| 5,763,449 | A | 6/1998 | Anaebonam et al. |
| 5,928,885 | A | 7/1999 | Nixon et al. |
| 5,962,461 | A | 10/1999 | Anaebonam et al. |
| 6,133,322 | A | 10/2000 | Rustin et al. |
| 6,472,378 | B2 | 10/2002 | von Borstel |
| 6,506,911 | B2 | 1/2003 | Hider et al. |
| 6,806,256 | B2 | 10/2004 | Ulrich et al. |
| 6,855,711 | B1 | 2/2005 | Warshawsky et al. |
| 6,906,052 | B2 | 6/2005 | Shah |
| 6,956,028 | B2 | 10/2005 | von Borstel |
| 6,989,397 | B1 | 1/2006 | Richardson et al. |
| 2002/0068758 | A1 | 6/2002 | Hider et al. |
| 2003/0158234 | A1 | 8/2003 | Spino et al. |
| 2003/0187019 | A1 | 10/2003 | Ullah et al. |
| 2004/0101521 | A1 | 5/2004 | Anderson |
| 2004/0116401 | A1 | 6/2004 | Shah |
| 2005/0250738 | A1 | 11/2005 | Mosher et al. |
| 2006/0030619 | A1 | 2/2006 | Liu et al. |
| 2006/0093663 | A1 | 5/2006 | Suzuki |
| 2006/0100189 | A1 | 5/2006 | Gurtner et al. |
| 2006/0234927 | A1 | 10/2006 | Youdim et al. |
| 2006/0281748 | A1 | 12/2006 | Gurtner et al. |
| 2007/0197469 | A1 | 8/2007 | Murthy |
| 2008/0242706 | A1 | 10/2008 | Tam et al. |
| 2009/0023784 | A1 | 1/2009 | Munnich et al. |

FOREIGN PATENT DOCUMENTS

| CA | 1095921 | 2/1981 |
|---|---|---|
| CA | 1290096 | 10/1991 |
| CA | 2100158 | 7/1992 |
| CA | 2287907 | 12/1996 |
| CA | 2226340 | 1/1997 |
| CA | 1340608 | 6/1999 |
| DE | 10336497 A1 | 3/2005 |
| EP | 0120670 | 10/1984 |
| EP | 0138420 | 5/1985 |
| EP | 0336369 | 11/1989 |
| EP | 1025858 A1 | 8/2000 |
| GB | 2136807 | 9/1984 |
| WO | WO 9520584 | 8/1995 |
| WO | 9527485 | 10/1995 |
| WO | 0117530 A1 | 3/2001 |
| WO | 0202114 A1 | 1/2002 |
| WO | 03075910 A1 | 9/2003 |
| WO | 2007095728 A1 | 8/2007 |
| WO | 2008116301 A1 | 10/2008 |
| WO | 2009103950 A1 | 8/2009 |

OTHER PUBLICATIONS

Block, Lawrence H., "Medicated Topicals", Remington: The Science and Practice of Pharmacy, Ed. Daniel Limmer, 2000, pp. 836-857, Lippincott Williams & Wilkins, Baltimore.
Buss, Joan L. et al., "The Role of Iron Chelation in Cancer Therapy", Current Medical Chemistry, 2003, pp. 1021-1034, vol. 10.
Carmichael, James et al., "Evaluation of a Tetrazolium-based Semiautomated Colorimetric Assay: Assessment of Chemosensitivity Testing", Cancer Research, Feb. 15, 1987, pp. 936-942, vol. 47.
Cooper, Mindy A. et al., "Urinary Iron Speciation in Nephrotic Syndrome", American Journal of Kidney Diseases, Feb. 1995, pp. 314-319, vol. 25, No. 2.
Dhungana, Suraj et al., "Fe(III) Coordination Properties of a New Saccharide-Based Exocyclic Trihydroxamate Analogue of Ferrichrome", Inorganic Chemistry, 2003, pp. 42-50, vol. 42.
Dean, Roger T. et al., "The Action of Nine Chelators on Iron-Dependent Radical Damage", Free Radical Res., 1994, pp. 83-101, vol. 20, No. 2.
Gutteridge, John M.C., "Superoxide-Dependent Formation of Hydroxyl Radicals from Ferric-Complexes and Hydrogen Peroxide: An Evaluation of Fourteen Iron Chelators", Free Radical Res. Comms., 1990, pp. 119-125, vol. 9, No. 2.

(Continued)

*Primary Examiner* — Zinna Northington Davis
(74) *Attorney, Agent, or Firm* — The Webb Law Firm

(57) ABSTRACT

The present invention relates to novel derivatives of deferiprone. In particular, the present invention relates to fluorinated derivatives of deferiprone or pharmaceutically acceptable salts thereof, pharmaceutical compositions comprising same, processes for the manufacture thereof and their use in the treatment of neurodegenerative diseases caused by the presence of free iron or iron accumulation in neural tissues and in diseases wherein excess iron must be removed or redistributed.

5 Claims, 5 Drawing Sheets

(56) References Cited

OTHER PUBLICATIONS

Dehkordi, Lotfollah S., "Basic 3-hydroxypyridin-4-ones: Potential antimalarial agents", European Journal of Medicinal Chemistry, 2008, pp. 1035-1047, vol. 43.

Molina-Holgado, Francisco et al., "Metals ions and neurodegeneration", Biometals, 2007, pp. 639-654, vol. 20.

Kang, Sam Sik et al., "Neuroprotective effects of flavones on hydrogen peroxide-induced apoptosis in SH-SY5Y neuroblastoma cells", Bioorganic & Medicinal Chemistry Letters, 2004, pp. 2261-2264, vol. 14.

Kerns, E. et al., "Blood-Brain Barrier, Drug-Like Properties: Concepts, Structure Design and Methods", 2008, Elsevier.

Kurz, Tino et al., "Relocalized redox-active lysosomal iron is an important mediator of oxidative-stress-induced DNA damage", Biochemical Journal, 2004, pp. 1039-1045, vol. 378.

Porter, Stuart C., "Coating of Pharmaceutical Dosage Forms," Remington: The Science and Practice of Pharmacy, Ed. Daniel Limmer, 2000, pp. 894-902, Lippincott Williams & Wilkins, Baltimore.

Mosmann, Tim, "Rapid Colorimetric Assay for Cellular Growth and Survival: Application to Proliferation and Cytotoxicity Assays", Journal of Immunological Methods, 1983, pp. 55-63, vol. 65.

Liu, Zu D. et al., "Design, Synthesis and Evaluation of N-Basic Substituted 3-Hydroxypyridin-4-ones: Orally Active Iron Chelators with Lysosomotrophic Potential", Journal of Pharmacy and Pharmacology, 2000, pp. 263-272, vol. 52.

Pierre, J.L. et al., "Iron and activated oxygen species in biology: The basic chemistry", BioMetals, 1999, pp. 195-199, vol. 12.

Persson, H. Lennart et al., "Iron-binding drugs targeted to lysosomes: a potential strategy to treat inflammatory lung disorders", Expert Opinion on Investigational Drugs, 2005, pp. 997-1008, vol. 14, No. 8.

Sciarra, John J. et al., "Aerosols", Remington: The Science and Practice of Pharmacy, Ed. Daniel Limmer, 2000, pp. 963-979, Lippincott Williams & Wilkins, Baltimore.

Hecht, Gerald, "Opthalmic Preparations", Remington: The Science and Practice of Pharmacy, Ed. Daniel Limmer, 2000, pp. 821-835, Lippincott Williams & Wilkins, Baltimore.

Lee, Thomas Wai-Yip et al., "Controlled-Release Drug-Delivery Systems", Remington: The Science and Practice of Pharmacy, Ed. Daniel Limmer, 2000, pp. 903-929, Lippincott Williams & Wilkins, Baltimore.

Nairn, J.G., "Solutions, Emulsions, Suspensions, and Extracts", Remington: The Science and Practice of Pharmacy, Ed. Daniel Limmer, 2000, pp. 721-752, Lippincott Williams & Wilkins, Baltimore.

Turco, Salvatore J., "Intravenous Admixtures", Remington: The Science and Practice of Pharmacy. Ed. Daniel Limmer, 2000, pp. 807-820, Lippincott Williams & Wilkins, Baltimore.

Rudnic, Edward M. et al., "Oral Solid Dosage Forms",Remington: The Science and Practice of Pharmacy, Ed. Daniel Limmer, 2000, pp. 858-893, Lippincott Williams & Wilkins, Baltimore.

Hershko, Chaim et al. "Objectives and Mechanism of Iron Chelation Therapy", Annals of the New York Academy of Science, 2005, pp. 124-135, vol. 1054.

Hershko, Chaim et al. "ICL670A: a new synthetic oral chelator: evaluation in hypertransfused rats with selective radioiron probes of hepatocellular and reticuloendothelial iron stores and in iron-loaded rat heart cells in culture", Blood, 2001, pp. 1115-1122, vol. 97, No. 4.

Porter, John B., "A Risk-Benefit Assessment of Iron-Chelation Therapy", Drug Safety,1997, pp. 407-421, vol. 17, No. 6.

Lodi, Raffaele et al. "Mitochondrial Dysfunction in Friedreich's ataxia", Biological Signals and Receptors, 2001, pp. 263-270, vol. 10.

Crivori, P. et al., "Predicting Blood-Brain Barrier Permeation from Three-Dimensional Molecular Structure", Journal of Medicinal Chemistry, 2000, pp. 2204-2216, vol. 43.

File History for PCT WO 2007/085728, published as WO 2007/095728, (Aug. 23, 2007).

File History for U.S. Appl. No. 12/279,930, published as US 2009/0023784, (Jan. 22, 2009).

Apopharma, "Safety and Efficacy of Ferriprox™ (Deferiprone) Oral Solution in Iron Overloaded Pediatric Patients", NCT00529152, Sep. 12, 2007, ClinicalTrials.gov.

"Annex I—Summary of Product Characteristics" http://www.ferriprox.com/aboutferriprox/SPC_solution.pdf. on Nov. 12, 2008.

Berkovitch et al. "The Efficacy of Oral Deferiprone in Acute Iron Poisoning", American Journal of Emergency Medicine, 2000, pp. 36-40, vol. 18, No. 1.

Giardina et al. "Chelation Therapy in β-Thalassemia: An Optimistic Update", Seminars in Hematology, Oct. 2001, pp. 360-366, vol. 38, No. 4.

"Ferriprox—Procedural steps taken and scientific information after the authorisation changes made after Jan. 6, 2004". http:/www.emea.europa.eu/humandocs/PDFs/EPAR/Ferriprox/038799en8b.pdf on Nov. 12, 2008.

"Ferriprox—Procedural steps taken and scientific information after the authorisation changes made after, Jan. 6, 2004", available at http://www.emea.europa.eu/humandocs/PDFs/EPAR/Ferriprox/038799en8b.pdf, document printed Nov. 12, 2008.

European Commission Decision of Aug. 25, 1999 (labeled "Not for Publication") approving Apotex's Ferriprox® tablets, available at http://ec.europa.eu/health/documents/community-register/html/h108.htm (Jul. 17, 2013).

European Commission Decision of Nov. 19, 2007 (labeled "Not for Publication") approving Apotex's Ferriprox® 100mg/ml oral solution, available at http://ec.europa.eu/health/documents/community-register/html/h108. htm (Jul. 17, 2013).

Annex I, "Summary of Product Characteristics", to European Commission Decision of Nov. 19, 2007 (labeled "Not for Publication") approving Apotex's Ferriprox® 100mg/ml oral solution, available at http://ec.europa.eu/health/documents/community-register/html/h108.htm (Jul. 17, 2013).

"Summary of Community Decisions on Marketing Authorizations in Respect of Medicinal Products from Nov. 1, 2007 to Nov. 30, 2007," Official Journal of the European Union C316/42 (Dec. 28, 2007), http://ec.europa.eu/health/documents/community-register/html/h108.htm.

Akers, Michael J., et al.. "Parenteral Preparations", Remington: The Science and Practice of Pharmacy, Ed. David B. Troy, 2006, pp. 802-836, Lippincott Williams & Wilkins, Baltimore.

Block, Lawrence H. "Medicated Topicals", Remington: The Science and Practice of Pharmacy, Ed. David B. Troy, 2006, pp. 871-888, Lippincott Williams & Wilkins, Baltimore.

Crowley, Michael M. "Solutions, Emulsions, Suspensions, and Extracts", Remington: The Science and Practice of Pharmacy, Ed. David B. Troy, 2006, pp. 745-775, Lippincott Williams & Wilkins, Baltimore.

Ding, Xuan et al. "Extended-Release and Targeted Drug Delivery Systems", Remington: The Science and Practice of Pharmacy, Ed. David B. Troy, 2006, pp. 939-964, Lippincott Williams & Wilkins, Baltimore.

Lang, John C. et al. "Opthalmic Preparations", Remington: The Science and Practice of Pharmacy, Ed. David B. Troy, 2006, pp. 850-870, Lippincott Williams & Wilkins, Baltimore.

O'Connor, Robert E. et al. "Powders", Remington: The Science and Practice of Pharmacy. Ed. David B. Troy, 2006, pp. 702-719, Lippincott Williams & Wilkins, Baltimore.

Porter, Stuart C. "Coating of Pharmaceutical Dosage Forms," Remington: The Science and Practice of Pharmacy, Ed. David B. Troy, 2006, pp. 929-938, Lippincott Williams & Wilkins, Baltimore.

Rudnic, Edward M. et al. "Oral Solid Dosage Forms",Remington: The Science and Practice of Pharmacy, Ed. David B. Troy, 2006, pp. 889-928, Lippincott Williams & Wilkins, Baltimore.

Schlindwein, Walkiria et al. "New lipophilic 3-hydroxy-4-pyridinonate iron(III) complexes: synthesis and EXAFS structural characterisation", Dalton Transactions, 2006, pp. 1313-1321.

Sciarra, John C. et al. "Aerosols", Remington: The Science and Practice of Pharmacy, Ed. David B. Troy, 2006, pp. 1000-1017, Lippincott Williams & Wilkins, Baltimore.

Turco, Salvatore J. "Intravenous Admixtures", Remington: The Science and Practice of Pharmacy. Ed. David B. Troy, 2006, pp. 837-849, Lippincott Williams & Wilkins, Baltimore.

(56) References Cited

OTHER PUBLICATIONS

Avramovich-Tirosh, Y., et al., Journal of Neurochemistry, 100, 490-502, (2007).
Barnham, K.J., et al., Drug Design Reviews—Online, 1, 75-82, (2004).
Bush, A.I., et al., Science, vol. 265, No. 5177, 1464-1467, (1994).
Cherny, R.A., et al., Journal of Biological Chemistry, vol. 274, No. 33, 23223-23228, (1999).
Escuder-Gilabert, L., et al., Journal of Chromatography B, 807, 193-201, (2004).
Gabita, S.P., et al., Journal of Neurochemistry, 71, 2034-2040, (1998).
Gaeta, A., et al., British Journal of Pharmacology, 146, 1041-1059, (2005).
Kontoghiorghes, G. J., et al., Current Medicianl Chemistry, 11, 2161-2183, (2004).
Lovell, M.A., et al., Journal of the Neurological Sciences, 158, 4747-4752, (1998).
Manitpisitkul, P., et al., Drug Discovery, vol. 9, No. 15, 652-658, (2004).
Pardridge, W.M., Journal of Neurochemistry, vol. 70, No. 5, 1781-1792, (1998).
Ritchie, C.W., et al., Arch. Neurol., vol. 60, 1685-1691, (2003).
Sayre, L.M., et al., Journal of Neurochemistry, 74, 270-279, (2000).
Schlindwein, Walkiria et al., "new lipophilic 3-hydroxy-4-pridiononate iron (III) complexes: synthesis and EXAFS structural characterization", Dalton Transactions, (10), 1313-1321 (2006).
Usansky, H.H., et al., Pharmaceutical Research, 20, 390-396, (2003).
Olivieri, Nancy F. et al. "Iron-Chelation Therapy with Oral Deferiprone in Patients with Thalassemia Major", The New England Journal of Medicine, 1995, pp. 918-922, vol. 332, No. 14.
Olivieri, Nancy F. et al. "Long-Term Safety and Effectiveness of Iron-Chelation Therapy with Deferiprone for Thalassemia Major", The New England Journal of Medicine, 1998, pp. 417-423, vol. 339, No. 7.
Becker, Erika et al. "Frataxin: its role in iron metabolism and the pathogenesis of Friedreich's ataxia", The International Journal of Biochemistry & Cell Biology, 2001, pp. 1-10, vol. 33.
Boddaert, Nathalie et al. "Selective Iron Chelation in Friedreich Ataxia. Biological and Clinical Implications", Blood, 2007, pp. 401-408, vol. 110.
Breuer, William et al. "Desferrioxamine-chelatable iron, a component of serum non-transferrin-bound iron, used for assessing chelation therapy", Blood, 2001, pp. 792-798, vol. 97, No. 3.
Campuzano, Victoria et al. "Friedreich's Ataxia: Autosomal Recessive Disease Caused by an Intronic GAA Triplet Repeat Expansion", Science, 1996, vol. 271.
Cano, Stefan J. et al., "International Cooperative Ataxia Rating Scale (ICARS): Appropriate for Studies of Friedreich's Ataxia?", Movement Disorders, 2005, pp. 1585-1591, vol. 20, No. 12.
Chamberlain, Susan et al., "Mapping of mutation causing Friedreich's ataxia to human chromosome 9", Nature, 1988, pp. 248-250, vol. 334.
Chantrel-Groussard, Karine et al., "Disabled early recruitment of antioxidant defenses in Friedreich's ataxia", Human Molecular Genetics, 2001, pp. 2061-2067, vol. 10, No. 19.
Delatycki, Martin B. et al. "Direct Evidence that Mitochondrial Iron Accumulation Occurs in Friedreich Ataxia", Annals of Neurology, 1999, pp. 673-675, vol. 45, No. 5.
Delatycki, Martin B. et al. "Friedreich ataxia: from genes to therapies?", Medical Journal of Australia, 2005, p. 439, vol. 182. No. 9.
Delatycki, Martin B. et al. "Friedreich ataxia: an overview", Journal of Medical Genetics, 2000, pp. 1-8, vol. 37.
Forni, Gian Luca et al., "Regression of symptoms after selective iron chelation therapy in a case of neurodegeneration with brain iron accumulation.", Mov Discord, 2008, pp. 904-907, vol. 23, No. 6.
Franchini, Massimo et al. "Iron-chelation therapy: an update", The Hematology Journal, 2004, pp. 287-292, vol. 5.
Gakh, Oleksandr et al. "Mitochondrial iron detoxification is a primary function of frataxin that limits oxidative damage and preserves cell longevity", Human Molecular Genetics, 2006, pp. 467-479, vol. 15, No. 3.
Glickstein, Hava et al. "Intracellular labile iron pools as direct targets of iron chelators: a fluorescence study of chelator action in living cells", Blood, 2005, pp. 3242-3250, vol. 106, No. 9.
Goncalves, Sergio et al. "Deferiprone targets aconitase: Implication for Friedreich's ataxia treatment", BMC Neurology, 2008, vol. 8, No. 20.
Haacke, E. Mark et al. "Imaging iron stores in the brain using magnetic resonance imaging", Magnetic Resonance Imaging, 2005, pp. 1-25, vol. 23.
Hausse, A. O. et al. "Idebenone and reduced cardiac hypertrophy in Friedreich's ataxia", Heart, 2002, pp. 346-349, vol. 87.
Hershko, Chaim et al. "Iron overload and chelation", Hematology, 2005, pp. 171-173, vol. 10, Supplement 1.
Lim, C.K. et al. "Protection against Hydrogen Peroxide-Mediated Cytotoxicity in Friedreich's Ataxia Fibroblasts using Novel Iron Chelators of the 2-Pyridylcarboxaldehyde Isonicotinoyl Hydrazone Class", Molecular Pharmacology, 2008, pp. 225-235, vol. 74, No. 1.
Avis, Kenneth E., et al., "Parenteral Preparations", Remington: The Science and Practice of Pharmacy, Ed. Daniel Limmer, 2000, pp. 780-806, Lippincott Williams & Wilkins, Baltimore.
Lovejoy, David B. et al. "PCTH: A Novel Orally Active Chelator for the Treatment of Iron Overload Disease", Hemoglobin, 2006, pp. 93-104, vol. 30, No. 1.
Mandel, Silvia A. et al., "Multifunctional Activities of Green Tea Catechins in Neuroprotection", Neurosignals, 2005, pp. 46-60, vol. 14.
Molina-Holgado, Francisco et al. "Neuroprotective Actions of an Iron Chelator Against Alzheimer's Disease-Relevant Insults", Alzheimer's and Dementia, 2006, p. S631, vol. 2, Issue 3.
Pearce, J.M. "Friedreich's ataxia", Journal of neurology neurosurgery and psychiatry, 2004, p. 688, vol. 75, No. 5.
Pennell, Dudley J. et al. "Randomized controlled trial of deferiprone or deferoxamine in beta-thalassemia major patients with asymptomatic myocardial siderosis", Blood, 2006, pp. 3738-3744, vol. 107, No. 9.
Pootrakul, Pensri et al. "Labile plasma iron (LPI) as an indicator of chelatable plasma redox activity in iron-overloaded $\beta$-thalassemia/HbE patients treated with an oral chelator", Blood, 2004, pp. 1504-1510, vol. 104, No. 5.
Tam, Tim F., "Iron Chelator Research: Past, Present, and Future", Current Medicinal Chemistry, 2003, pp. 983-995, vol. 10.
Sopher, Bryce L. et al., "Cytotoxicity mediated by conditional expression of a carboxyl-terminal derivative of the $\beta$-amyloid precursor protein", Molecular Brain Research, 1994, pp. 207-217, vol. 26.
Richardson, Des R. "The therapeutic potential of iron chelators", Expert Opinion on Investigational Drugs, 1999, pp. 2141-2158, vol. 8. No. 12.
Richardson, D.R. et al. "Development of potential iron chelators for the treatment of Friedreich's ataxia: ligands that mobilize mitochondrial iron", Biochemica et Biophysica Acta, 2001, pp. 133-140, vol. 1536, Nos. 2-3.
Richardson, D.R., "Friedrich's ataxia: iron chelators that target the mitochondrion as a therapeutic strategy?", Expert Opinion on Investigational Drugs, 2003, pp. 235-245, vol. 12, No. 2.
Richardson, Des R. "The controversial role of deferiprone in the treatment of thalassemia", Journal of Laboratory and Clinical Medicine, 2001, pp. 324-329, vol. 137, No. 5.
Richardson, Des R., "Novel chelators for Central Nervous System Disorders That Involve Alterations in the Metabolism of Iron and Other Metal Ions", Annals of the New York Academy of Sciences, 2004, pp. 326-341, vol. 1012.
Rötig, Agnès et al., Aconitase and mitochondrial iron-sulphur protein deficiency in Friedreich ataxia, Nature Genetics, 1997, pp. 215-217, vol. 17.
Rund, Deborah et al., "$\beta$-Thalassemia", The New England Journal of Medicine, 2005, pp. 1135-1146, vol. 353.

(56) References Cited

OTHER PUBLICATIONS

Rustin, Pierre et al., "Effect of idebenone on cardiomyopathy in Friedreich's ataxia: a preliminary study", The Lancet, 1999, pp. 477-479, vol. 354.

Shvartsman, Maya et al., "Non-transferrin-bound iron reaches mitochondria by a chelator-inaccessible mechanism:biological and clinical implications", American Journal of Physiology—Cell Physiology, 2007, pp. C1383-C1394, vol. 293.

Simon, Delphine et al., "Friedreich Ataxia Mouse Models with Progressive Cerebellar and Sensory Ataxia Reveal Autophagic Neurodegeneration in Dorsal Root Ganglia", The Journal of Neuroscience, 2004, pp. 1987-1995, vol. 24. No. 8.

Sturm, Brigitte et al., "Friedreich's Ataxia, No Changes in Mitochondrial Labile Iron in Human Lymphoblasts and Fibroblasts—A Decrease in Antioxidative Capacity?", The Journal of Biological Chemistry, 2009, pp. 6701-6706, vol. 280, No. 8.

Voncken, Max et al., "Friedreich ataxia—update on pathogenesis and possible therapies", Neurogenetics, 2004, pp. 1-8, vol. 5.

Waldvogel, Daniel et al., "Increased Iron in the Dentate Nucleus of Patients with Friedreich's Ataxia", Annals of Neurology, 1999, pp. 123-125, vol. 46, No. 1.

Whitnall, Megan et al., "The MCK mouse heart model of Friedreich's ataxia: Alterations in iron-regulated proteins and cardiac hypertrophy are limited by iron chelation", PNAS, 2008, pp. 9757-9762, vol. 105, No. 28.

Whitnall, Megan et al., "Iron: A new Target for Pharmacological Intervention in Neurodegenerative Diseases", Seminars in Pediatric Neurology, 2006, pp. 186-197, vol. 13.

Sohn, Yang-Sung et al., "Redistribution of accumulated cell iron, A modality of chelation with therapeutic implications", Blood First Edition Paper, prepublished online Nov. 1, 2007.

Wilson, Robert B. et al., "Normal Serum Iron and Ferritin Concentrations in Patients with Friedreich's Ataxia", Annals of Neurology, 1998, pp. 132-134, vol. 44.

Friedreich, N., Virchow's Arch Path Anat, 1863, pp. 391-419, vol. 26.

Lodi, Raffaele et al. "Antioxidant Treatment Improves In Vivo Cardiac and Skeletal Muscle Bioenergetics in Patients with Friedreich's Ataxia", Annals of Neurology, May 2001, pp. 590-596, vol. 49, No. 5.

Figure 1

Physical Properties of Compounds of Formula I and Deferiprone

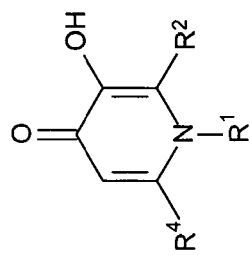

| | $R^4$ | $R^1$ | $R^2$ | $D_{7.4}$ | pKas | Log $k_{BMC}$ | Calculated Log BB | MW |
|---|---|---|---|---|---|---|---|---|
| Deferiprone | H | $CH_3$ | $CH_3$ | 0.17 | 3.55, 9.92 | -0.07 | -1.05 | 139.15 |
| Apo6719 | $CHF_2$ | $CH_3$ | H | 0.34 | 2.65, 8.28 | 0.02 | -0.96 | 175.13 |
| Apo6736 | $CHF_2$ | $CH_3$ | $CH_2OH$ | 0.37 | 2.34, 8.52 | 0.10 | -0.88 | 205.16 |
| Apo6757 | $CHF_2$ | $CH_3$ | $CH(OH)CH_3$ | 0.86 | nd | 0.25 | -0.73 | 219.18 |
| Apo6732 | $CHF_2$ | $CH_2CH_3$ | H | 0.97 | nd | 0.24 | -0.74 | 189.16 |
| Apo6756 | $CHF_2$ | c-Pr | H | 0.99 | nd | 0.23 | -0.75 | 201.17 |
| Apo6742 | $CHF_2$ | $CH_3$ | $CH_3$ | 1.04 | 2.96, 9.14 | 0.25 | -0.73 | 189.16 |
| Apo6727 | $CHF_2$ | allyl | H | 1.82 | nd | 0.44 | -0.54 | 201.17 |
| Apo6762 | $CH_3$ | $CH_3$ | $CH_2CF_3$ | 2.17 | 3.57, 10.37 | 0.56 | -0.42 | 221.18 |
| Apo6761 | $CHF_2$ | $CH_3$ | $CH_2CH_3$ | 3.33 | nd | 0.48 | -0.50 | 203.19 |
| Apo6725 | $CHF_2$ | $CH_2$-c-Pr | H | 3.82 | nd | 0.66 | -0.32 | 215.20 |
| Apo6729 | $CH_3$ | $CH_3$ | $CH(OH)CF_3$ | 3.95 | 2.77, 7.78 | 0.76 | -0.22 | 237.18 |

Figure 2

Log $K_{BMC}$ Values of 31 Reference Drug Substances

| Drug Name | Log $K_{BMC}$ (Lit. values)[1,2] | Log BB (Lit. values)[1] | Log $K_{BMC}$ (this work)[2] | Log $K_{BMC}$ Test article in 4 mM EDTA (this work)[3] |
|---|---|---|---|---|
| Atenolol | -0.34 | -1.42 | -0.24 | -0.25 |
| Ranitidine | 0.11 | -1.23 | -0.19 | -0.20 |
| Theophyline | 0.22 | -0.29 | 0.19 | 0.21 |
| Caffeine | 0.26 | -0.06 | 0.20 | 0.21 |
| Cimetidine | 0.28 | -1.42 | 0.52 | 0.50 |
| Antipyrine | 0.34 | -0.10 | 0.28 | 0.29 |
| Salicylic acid | 0.55 | -1.10 | 0.57 | 0.58 |
| Acetylsalicylic acid | 0.57 | -0.50 | 0.56 | 0.58 |
| Acetaminophen | 0.66 | -0.31 | 0.61 | 0.62 |
| Carbamazepine epoxide | 0.84 | -0.34 | 0.86 | 0.87 |
| Clonidine HCl | 0.92 | 0.11 | 0.66 | 0.60 |
| Ibuprofen | 1.19 | -0.18 | 1.31 | 1.34 |
| Carbamazepine | 1.21 | -0.07 | 1.15 | 1.16 |
| Alprazolam | 1.44 | 0.04 | 1.32 | 1.33 |
| Clobazam | 1.45 | 0.35 | 1.36 | 1.36 |
| Phenytoin | 1.54 | -0.04 | 1.44 | 1.45 |
| Propranolol HCL | 1.62 | 0.64 | 1.29 | 1.25 |
| Diazepam | 1.65 | 0.52 | 1.55 | 1.54 |
| Benzene | 1.66 | 0.37 | 1.58 | 1.59 |
| Pyrilamine | 1.67 | 0.50 | 1.53 | 1.47 |
| Midazolam | 1.70 | 0.36 | 1.55 | 1.56 |
| Hydroxyzine HCl | 1.74 | 0.39 | 1.65 | 1.63 |
| Desipramine HCl | 1.79 | 1.20 | 1.52 | 1.51 |
| Toluene | 1.86 | 0.37 | 1.77 | 1.78 |
| Amitriptyline HCl | 2.37 | 0.90 | 2.05 | 2.04 |
| Fluphenazine HCl | 1.99 | 1.51 | 1.72 | 1.71 |
| Haloperidol | 2.01 | 1.34 | 1.80 | 1.78 |
| Promazine HCl | 2.24 | 1.23 | 1.92 | 1.91 |
| Chlorpromazin HCl | 2.43 | 1.06 | 2.04 | 2.04 |
| Imipramine HCl | 2.49 | 1.06 | 1.95 | 1.97 |
| Trifluoperazin | 2.55 | 1.44 | 2.14 | 2.26 |

[1] Escuder-Gilabert, L., *et al.*, Journal of Chromatography B, 2004, 807, 193-201.

[2] HPLC conditions (from note 1) - Column: Kromasil C18, 5µM, 150 x 4.6 mm; Guard column: Kromasil C18, 5µM, 50 x 4.6 mm; Mobile phase: 40 mM Brij35, 157 mM NaCl, 50 mM phosphate buffer, pH 7.4; Method: isocratic; Flow rate: 1.0 mL/min; T = 36.5°C.

[3] HPLC conditions - Column: Kromasil C18, 5µM, 150 x 4.6 mm; Guard column: Kromasil C18, 5µM, 50 x 4.6 mm; Mobile phase: 40 mM Brij35, 157 mM NaCl, 4mM EDTA, 50 mM phosphate buffer, pH 7.4; Method: isocratic; Flow rate: 1.0 mL/min; T = 36.5°C.

Relationship between Log $K_{BMC}$ and Log BB of 31 Reference Drug Substances

Plot 1 regression: Log BB = -0.98 + Log $k_{BMC}$   $r^2$ = 0.72

Figure 4

Properties of Fluorinated Analogues of Deferiprone

| Compound | L1 | CP502 | Apo6719 | Apo6736 | Apo6742 | Apo6729 | Apo6762[1] |
|---|---|---|---|---|---|---|---|
| $pKa_1$ | 9.92 | 8.40 | 8.28 | 8.52 | 9.14 | 7.78 | 10.37 |
| $pKa_2$ | 3.55 | 2.70 | 2.65 | 2.34 | 2.96 | 2.77 | 3.57 |
| $\log K_1$ | 14.85 | 12.93 | 12.24 | 12.88 | 13.78 | 12.76 | 15.56 |
| $\log K_2$ | 12.40 | 11.32 | 10.79 | 10.84 | 11.43 | 10.74 | 12.94 |
| $\log K_3$ | 9.99 | 9.39 | 8.96 | 9.13 | 9.40 | 8.72 | 10.00 |
| $\log \beta_3$ | 37.24 | 33.64 | 31.99 | 32.85 | 34.61 | 31.72 | 38.51 |
| $pFe^{3+}$ | 20.2 | 20.8 | 19.7 | 19.9 | 19.9 | 20.7 | 20.2 |
| $D_{7.4}$ | 0.17 | 0.03 | 0.34 | 0.37 | 1.04 | 3.95 | 2.17 |

[1] Solution is prepared in 0.1 M NaCl in 1:1 MeOH and $H_2O$. The experiment is carried out in mix-solvent of 0.1 M NaCl in DI-water and MeOH (50/50, v/v).

Speciation Plot of Fe(III) - Apo6719 (a compound of Formula I) Complexes $[Fe(III)]_{total} = 1 \times 10^{-6}$ M and $[L]_{total} = 1 \times 10^{-5}$ M

FLUORINATED DERIVATIVES OF DEFERIPRONE

CONTINUING DATA

This application is a divisional application of U.S patent application Ser. No. 12/078,079 filed Mar. 27, 2008 now U.S. Pat. No. 8,026,261 which claims the benefit of U.S. Provisional Application No. 60/907,290 filed Mar. 28, 2007.

FIELD OF THE INVENTION

The present invention relates to novel derivatives of deferiprone. In particular, the present invention relates to fluorinated derivatives of deferiprone or pharmaceutically acceptable salts thereof, pharmaceutical compositions comprising same, processes for the manufacture thereof and their use in the treatment of neurodegenerative diseases caused by the presence of free iron or iron accumulation in neural tissues and in diseases wherein excess iron must be removed or redistributed.

BACKGROUND OF THE INVENTION

The crucial role of metal ions in neurodegeneration and the use of chelators as a promising therapeutic strategy have been reviewed by Gaeta and Hider (Gaeta, A. and Hider, R. C., British Journal of Pharmacology, 2005, 146, 1041-1059). In patients with Parkinson's disease (PD), the selective degeneration of the dopamine-containing region of the brain occurs. The iron levels in the substantia nigra (SN) are elevated. Fe(II) can react with hydrogen peroxide to generate hydroxyl radical, which in turn leads to cellular degeneration via the destruction of proteins, nucleic acids and phospholipids. It is proposed that reducing the free iron level with chelators can inhibit the onset of the disease, i.e., neural degeneration. The latter results in reducing dopaminergic cell loss. Examples of small molecule chelators for this utility are deferiprone, clioquinol, and desferrioxamine. These chelators have been claimed to reduce free iron levels in neural tissues as a means to reduce neural degeneration (US 2004/0101521). The reduction of iron-induced oxidative stress is protective to the neuron. Iron chelation appears to be one of the new approaches to combat neurodegenerative disease such as Alzheimer's disease (AD) and PD. An effective chelator can, in principle, prevent generation of hydroxyl radical induced by iron-hydrogen peroxide, and mobilize free chelatable iron from the brain, thus exerting its neuroprotective function.

Current drugs used for PD therapy include L-dopa, dopamine (DA) agonists, catechol O-methyl transferase inhibitors such as talcapone, and monoamine oxidase B (MAO-B) inhibitors such as rasagiline and selegiline. However, these drugs cannot mitigate the progression of the disease process. A research group from Israel reported the use of novel bifunctional iron chelators as potential agents in AD, PD and other neurodegenerative diseases (U.S. Pat. No. 6,855,711). The rationale is based on the observation that increased level of iron, and MAO-B activity in the brain are the major pathogenic factors in PD and other neurodegenerative diseases. Since iron chelators and MAO-B inhibitors have been shown to possess neuroprotective activity in animals, it is logical to connect the MAO-B inhibitor onto an iron chelator and apply such agents for the treatment and/or prevention of neurodegenerative diseases. One of the lead compounds is M30, an 8-hydroxyquinoline derivative (iron chelator) attached to a MAO-B inhibitor (Avramovich-Tirosh, Y., et al., Journal of Neurochemistry, 2007, 100, 490-502).

Amyloids are insoluble fibrous protein aggregations (usually polymeric). From a chemical perspective, amyloids form insoluble beta-pleated sheet structures and cannot be destroyed by proteases. Amyloid β (Aβ or Abeta) is a small peptide of 39-43 amino acids that is the main constituent of amyloid plaques in the brains of AD patients. AD is a dementia that results in the irreversible deterioration of mental function and eventually leads to the death of the patient. Aβ is also found in the brains of patients with Down's syndrome. Due to its more hydrophobic nature, the $A\beta_{42}$ fragment is the most amyloidogenic form of the peptide allowing them to build up with other fragments to form AD plaque.

New therapeutic approaches to the treatment or prevention of AD involve slowing, or reversing Aβ accumulation. The mechanism of toxicity and the neurochemical events that cause Aβ deposition are still unclear, but transition metals such as copper, zinc (II) and iron (III) are found concentrated in and around amyloid plaques (Lovell, M. A., et al., J. Neurol. Sci. 1998, 158: 47-52). Aβ is known to exhibit a high affinity for transition metal ions. The binding of metal, in particular $Zn^{++}$, and to a lesser extent $Cu^{++}$ and $Fe^{3+}$, to Aβ markedly increases its aggregation and the formation of amyloid deposits (Bush, A. I., et al., Science, 1994, 265: 1464-1467). Cherny et al. demonstrated that both processes (aggregation and deposition) can be reversed in the presence of metal-chelating agents (Cherny, R. A., et al., J. Biol. Chem. 1999, 274: 23223-23228). The binding of redox active transition metals (i.e., $Cu^{2+}$ and $Fe^{3+}$) to Aβ also leads to the generation of reactive oxygen species (Sayre, L. M., et al., J. Neurochem. 2000, 74: 270-279), which are known to have deleterious effects on a wide variety of biomolecules. Bio-metal- and amyloid-mediated production of reactive oxygen species are believed to be responsible, at least in part, for the oxidative stress observed in the brains of AD patients (Gabbita, S. P., et al., J. Neurochem. 1998, 71: 2034-2040).

Barnham et al. reported the use of chelators as metal-protein attenuating compounds (MPAC) for the treatment of AD (Barnham, K. J., et al., Drug Design Reviews—Online, 2004, 1, 75-82). The chelator is proposed to chelate the metal at the accumulation site in the brain and redistribute to other tissues inside the brain. The chelator clioquinol, 5-chloro-8-hydroxy-7-iodo-quinoline has been used as an oral drug in a phase II clinical trial (Ritchie, C. W., et al., Arch Neurol, 2003, 60, 1685-1691). Due to manufacturing problems with clioquinol and the presence of the 5,7-diiodo analogue, a replacement analogue to clioquinol is being developed by Prana Biotechnology Ltd. (Melbourne, Australia) for the treatment of AD.

The design and development of deferiprone, a low molecular weight iron chelator has been reviewed (Kontoghiorghes, G. J., et al., Current Medicinal Chemistry, 2004, 11 2161-83). In addition to its use in the treatment of the above neurogenerative diseases, deferiprone may also be used to redistribute iron in conditions such as Hallervorden-Spatz syndrome and Friedreich's ataxia.

The bidentate chelator deferiprone, 3-hydroxy-1,2-dimethyl-1H-pyridin-4-one is a drug used in the treatment of iron overload disease. The same drug can be used in non-iron overloaded conditions and towards the treatment of neurogenerative diseases (US 2004/0101521). In order to use a chelator to mobilize free chelatable iron from the brain and exert its neuroprotective function, the chelator must penetrate the blood brain barrier (BBB) to reach the neural tissues. Deferiprone is chosen because of its low molecular weight (139) and its ability to penetrate the BBB. For example, deferiprone has a distribution coefficient of 0.17 at pH 7.4 and its ability to penetrate the BBB can be estimated by an experimentally determined physico-chemical parameter $k_{BMC}$ wherein BMC is known as biopartitioning micellar chromatography. Escuder-Gilabert et al. reported the potential of BMC as an in vitro technique for predicting drug penetration across the BBB (Escuder-Gilabert, L., et al., Journal of Chromatography B, 2004, 807, 193-201) and demonstrated the usefulness of BMC for correlating experimentally determined BBB penetration of drugs and determined the $k_{BMC}$ of more than 30 known central nervous system (CNS) drug substances.

SUMMARY OF THE INVENTION

It is an object of the present invention to provide fluorinated analogues of deferiprone and the composition of such compounds, which analogues are active as iron chelators and hence useful in the treatment of neurodegenerative diseases caused by the presence of free iron or accumulation of iron in neural tissues.

It is another object of the present invention to provide fluorinated analogues of deferiprone and the composition of such compounds, which analogues are useful as chelators in the removal of iron in diseases wherein excess iron must be removed or redistributed.

It is a further object of the present invention to provide processes for the synthesis of fluorinated analogues of deferiprone compounds.

If one increases the lipophilicity of the 3-hydroxy-1,2-dimethyl-1H-pyridin-4-one chelator pharmacophore by attaching properly designed substituents, one would expect to significantly improve the $k_{BMC}$ value of the new analogues. This approach predicts that new compounds will penetrate the BBB and a reasonable amount of drug substance will be available in the brain to exert its pharmacological action. We attached fluoroalkyl substituents at the 2 or 6 position of the 3-hydroxy-4-pyridinone skeleton, and evaluated the $k_{BMC}$ values of fluoro derivatives of deferiprone using the above methods. The chemical stability of these novel fluoro analogues of deferiprone was also evaluated. Employing BMC as an in vitro technique for predicting drug penetration across the BBB, we invented a series of stable fluorinated deferiprone analogues with improved $k_{BMC}$ values over deferiprone. These compounds have advantages over deferiprone in the penetration of the BBB. Availability of the drug in the brain ensures that the compound can chelate free iron in neural tissues, thus enabling the removal or redistribution of free iron ion. Since the chelator may be used to redistribute iron, chelators with the 3-hydroxy-4-pyranone skeleton may also be used if the fluoroalkyl substituent attachment to the pyranone ring improves its BBB penetration properties.

There is very limited information on the synthesis of fluorinated derivatives of 3-hydroxy-pyridin-4-one and their use in medicinal chemistry. EP 0 336 369 A1 reported compound (A) as a crude material and the conversion of the $CHF_2$ functionality to CHO with trifluoroacetic acid

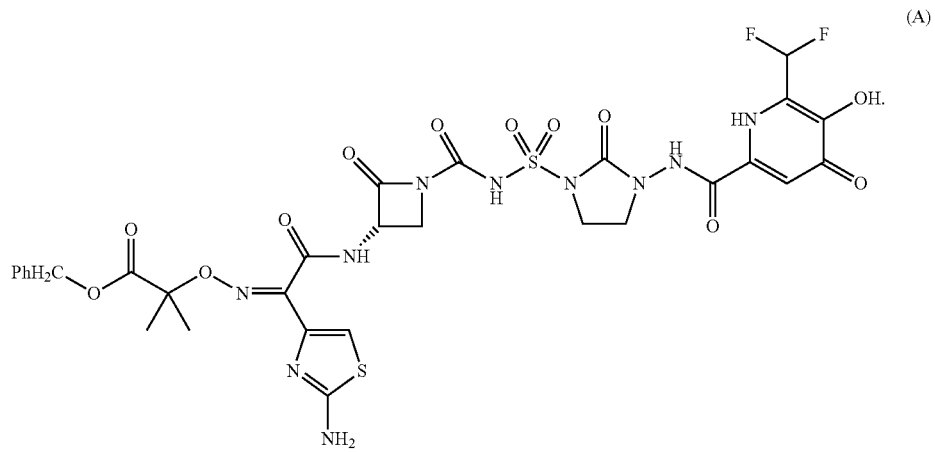

EP 0 120 670 B1 generally discloses an iron complex of a 3-hydroxypyridone of the chemical structure (B)

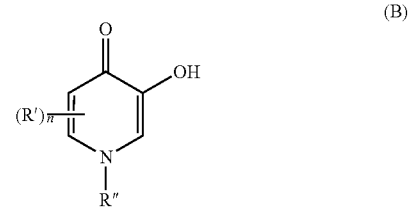

in which each R' separately is a $C_{1-6}$ aliphatic hydrocarbon group or a $C_{1-3}$ alkyl group substituted by a $C_{1-4}$ alkoxy, halogen or hydroxy group, R" is a $C_{1-6}$ aliphatic hydrocarbon group, a formyl or ($C_{1-4}$ alkyl)-carbonyl group, or a $C_{1-8}$ aliphatic hydrocarbon group substituted by one or more substituents selected from formyl, ($C_{1-4}$ alkyl)-carbonyl, $C_{1-4}$ alkoxy, carbamoyl, sulphamoyl, mono- and di-$C_{1-6}$ aliphatic hydrocarbyl N-substituted carbamoyl and N-substituted sulphamoyl, formylamino, (($C_{1-6}$ aliphatic hydrocarbyl)-carbonylamino, ($C_{1-6}$ aliphatic hydrocarbyl)-sulphonylamino, mono-$C_{1-6}$ aliphatic hydrocarbyl N-substituted formylamino, N-substituted ($C_{1-6}$ aliphatic hydrocarbyl)-carbonylamino and N-substituted ($C_{1-6}$ aliphatic hydrocarbyl)-sulphonylamino, formyloxy, ($C_{1-6}$ aliphatic hydrocarbyl)-carbonyloxy, ($C_{1-6}$ aliphatic hydrocarbyl)-oxycarbonyl, ($C_{1-6}$ aliphatic hydrocarbyl)-sulphonyloxy, ($C_{1-6}$ aliphatic hydrocarbyl)-oxysulphonyl, halogen and hydroxy groups, and n is 0, 1, 2 or 3. However, EP 0 120 670 B1 does not specifically disclose mono halo compounds of formula (B) wherein R' is a $C_{1-3}$ aliphatic hydrocarbon group substituted by a halogen and R'' is a $C_{1-6}$ aliphatic hydrocarbon group, their characterization or methods for their synthesis.

In our search for a new analogue of deferiprone with better partition coefficient and BBB penetration properties, we first investigated the synthesis of a compound with the chemical structure (C)

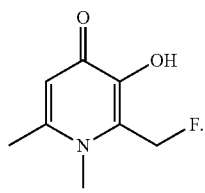
(C)

We have determined that compound (C) is an unstable compound in aqueous solution. We then investigated the synthesis of a compound with the chemical structure (D)

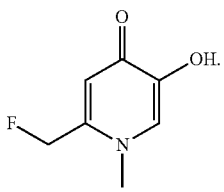
(D)

We determined that this compound can be prepared, but it is also unstable in aqueous solution. These results led to further structural refinement and design of 3-hydroxy-4-pyridinones that are more lipophilic than deferiprone, and with better BBB penetration properties than deferiprone in a biopartitioning micellar high pressure liquid chromatography (HPLC) system. The novel F-analogues of deferiprone of the present invention can be used to replace deferiprone and other less effective chelators in the treatment of neurodegenerative diseases.

The present invention is based upon the preparation of a class of 3-hydroxy-4-pyridinone derivatives and selected 3-hydroxy-4-pyranone derivatives that are chemically stable with higher BBB permeability than deferiprone. The ability of a chelator to remove iron in a biological system is governed by the pFe(III). pFe(III) is a chemical parameter and is defined as $-\log [Fe(III)]$, the free unbound iron concentration in a system with $1 \times 10^{-5}$ M chelator and $1 \times 10^{-6}$ M Fe(III). Compounds of the present invention have pFe(III) values above 19 and are extremely useful in extracting excess iron from the body. Examples of compounds in the prior art that have pFe(III) values above 19 and that are useful in extracting excess iron from the body include deferiprone (L1), deferasirox (ICL670), desferral (desferrioxamine, DFO).

Thus, in accordance with one aspect of the present invention, there are provided compounds of formula (I)

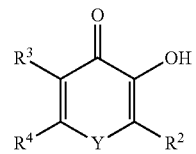
(I)

or pharmaceutically acceptable salts thereof,
wherein (i):
Y is $NR^1$, wherein $R^1$ is selected from the group consisting of hydrogen, $C_1$-$C_6$ alkyl (preferably $C_1$-$C_4$ alkyl), cyclopropylmethyl, allyl and cyclopropyl;
$R^2$ is selected from the group consisting of hydrogen, $C_1$-$C_4$ alkyl, and $R^5$CHOH wherein
$R^5$ is selected from the group consisting of hydrogen, $C_1$-$C_3$ alkyl and trifluoromethyl;
$R^3$ is selected from the group consisting of methyl, hydrogen and $CF_3CHOH$;
$R^4$ is $CHF_2$; and
wherein the compound of formula (I) is a compound of formula (II)

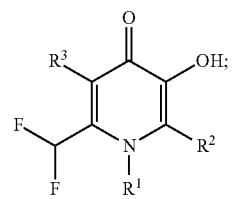
(II)

or (ii):
Y is $NR^1$, wherein $R^1$ is defined as above;
$R^2$ is selected from the group consisting of $CHF_2$, $CF_3CH_2$, and $CF_3CHOH$;
$R^3$ and $R^4$ are each selected from the group consisting of methyl and hydrogen; and
wherein the compound of formula (I) is a compound of formula (III)

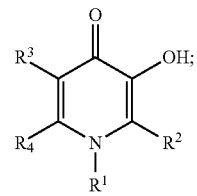
(III)

or (iii):
Y is $NR^1$, wherein $R^1$ defined as above;
$R^2$ is selected from the group consisting of hydrogen and $C_1$-$C_4$ alkyl, with the proviso that when $R^4$ is hydrogen, $R^2$ is not hydrogen;
$R^3$ is $CF_3CHOH$;
$R^4$ is selected from the group consisting of hydrogen and methyl; and
wherein the compound of formula (I) is a compound of formula (IIIC)

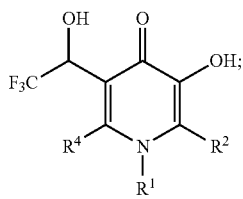

(IIIC)

or (iv):
Y is O;
R² is CF₃CHOH;
R³ is selected from the group consisting of methyl and hydrogen;
R⁴ is selected from the group consisting of hydrogen and $C_1$-$C_4$ alkyl; and
wherein the compound of formula (I) is a compound of formula (IV)

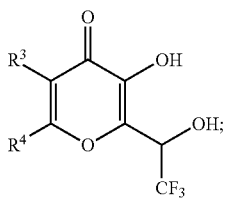

(IV)

or (v):
Y is O;
R² is hydrogen;
R³ is hydrogen;
R⁴ is difluoromethyl; and
wherein the compound has the following chemical structure

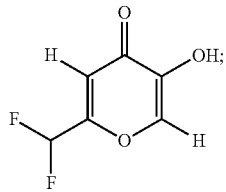

or (vi):
Y is O or NR¹, wherein R¹ is defined as above;
R² is selected from the group consisting of hydrogen, $CHF_2$, $CH_2CF_3$, $C_1$-$C_6$ alkyl (preferably $C_1$-$C_4$ alkyl), and R₅CHOH, wherein R⁵ is selected from the group consisting of hydrogen, $C_1$-$C_6$ alkyl (preferably $C_1$-$C_4$ alkyl) and trifluoromethyl;
R³ is selected from the group consisting of methyl, hydrogen, $CH_2CF_3$, $CF_3CHOH$ and $C_1$-$C_6$ alkyl (preferably $C_1$-$C_4$ alkyl); and
R⁴ is selected from the group consisting of $CHF_2$, $CF_3CHOH$, $CH_2CF_3$, methyl, hydrogen and $C_1$-$C_6$ alkyl (preferably $C_1$-$C_4$ alkyl);
with the proviso that when R₃ is CF₃CHOH and R⁴ is hydrogen, R² is not hydrogen.

In accordance with another aspect of the present invention, there is provided a pharmaceutical composition comprising a compound of the formula (I) and at least one pharmaceutically acceptable carrier.

In accordance with another aspect of the invention, there is provided a method of treating a neurodegenerative disease in a patient, wherein the method comprises administering to the patient an effective amount of a compound of the formula (I).

In an embodiment of the present invention, the neurodegenerative disease is caused by the presence of free iron or iron accumulation in neural tissues.

In an embodiment of the present invention, the neurodegenerative disease is selected from the group consisting of Parkinson's disease and Alzheimer's disease.

In accordance with another aspect of the invention, there is provided a method of treating an iron overload disease in a patient, wherein the method comprises administering to the patient an effective amount of a compound of the formula (I).

In an embodiment of the present invention, the iron overload disease is selected from the group consisting of Friedreich's ataxia, β-thalassemia and Hallervorden-Spatz syndrome.

In accordance with another aspect of the present invention, there is provided the use of a compound of the formula (I) as a chelator for the removal of excess iron from the body of a patient.

In accordance with another aspect of the present invention, there is provided the use of a compound of the formula (1) as a chelator for the redistribution of iron within the body of a patient.

Other and further advantages and features of the present invention will be apparent to those skilled in the art from the following detailed description thereof taken in conjunction with the accompanying drawings.

BRIEF DESCRIPTION OF THE DRAWINGS

In the accompanying drawings:
FIG. 1 provides a table illustrating the physical properties of selected compounds of formula (I) according to the present invention and deferiprone.
FIG. 2 provides a table illustrating the chromatographic capacity factor $k_{BMC}$ of 31 reference drug substances.
FIG. 4 provides a table illustrating the chemical properties of a series of compounds of formula (I) according to the present invention.

DETAILED DESCRIPTION OF THE PREFERRED EMBODIMENTS OF THE INVENTION

Figure 3:
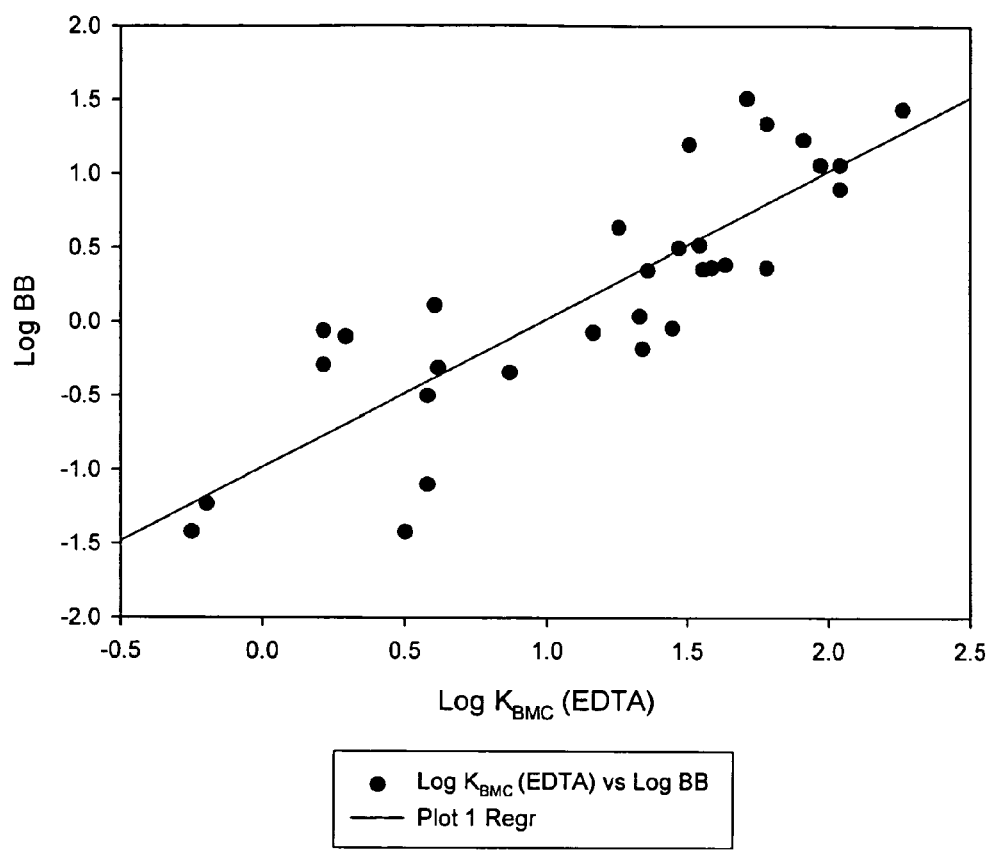
FIG. 3 illustrates the relationship between log BB and log $k_{BMC}$ of 31 reference drug substances.

As used herein:
The term "alkyl" refers to an aliphatic hydrocarbon chain with the formula $C_nH_{2n+1}$. $C_1$-$C_6$ alkyl refers to the alkyl group with 1 to 6 carbon atoms, i.e., n=1 to 6. $C_1$-$C_4$ alkyl refers to the alkyl group with 1 to 4 carbon atoms, i.e., n=1 to 4. $C_1$-$C_3$ alkyl refers to the alkyl group with 1 to 3 carbon atoms, i.e., n=1 to 3. The aliphatic carbon chain can be linear or branched. Examples of an alkyl group include, but are not limited to, methyl, ethyl, propyl, isopropyl, butyl, 2-butyl, isobutyl and tert-butyl.

The distribution coefficient of a solute between two phases is calculated as the ratio of the concentration of the solute in one phase to the concentration of the solute in the other phase under equilibrium conditions. The solute is the compound of interest. One phase is octanol, while the other phase is normally phosphate buffer at a pH of 7.4. The term "$D_{7.4}$" refers to the distribution coefficient at pH 7.4. $D_{7.4}$ reflects the true behavior of an ionizable compound in a solution at pH 7.4. This property is exceptionally useful in evaluating pH-dependent pharmacokinetic properties, drug absorption, bioavailability, metabolism and toxicity.

The term "log BB" refers to the logarithm value of brain to plasma concentration ratio of the solute wherein the solute is the drug substance under study (Usansky, H. H. and Sinko, P. J., Pharmaceutical Research, 2003, 20, 390-396).

The term "$pFe^{3+}$" refers to $-\log [Fe^{3+}]$. $[Fe^{3+}]$ is the concentration of free, unchelated $Fe^{3+}$ in a mixture containing $1\times10^{-5}$ M chelator and $1\times10^{-6}$ M $Fe^{3+}$. The $pFe^{3+}$ is a measure of the effectiveness of a compound in the chelation of $Fe^{3+}$. The higher the pFe value, the less available is the presence of unchelated Fe(III). Free iron ion can result in redox reactions in biological systems.

The term "log $k_{BMC}$" refers to the logarithm of the chromatographic capacity factor (reference retention time) in BMC, a special type of HPLC (Escuder-Gilabert, L., et al., Journal of Chromatography B, 2004, 807, 193-201). This analytical technique was used to correlate the log $k_{BMC}$ of 31 reference drug substances with known experimentally determined log BB values. A linear regression mathematical equation log BB=a(log $k_{BMC}$)+b was obtained from these reference drug substances wherein a and b are constants. The log $k_{BMC}$ of the compounds of the present invention was measured by BMC. The experimental log $k_{BMC}$ of the compounds of the present invention was fit into the log BB=a(log $K_{BMC}$) b equation to obtain a calculated log BB value. The calculated log BB is an indicator of the BBB penetration property of the compounds of the present invention.

The term "DAST" is the chemical diethylaminosulfur trifluoride.

The term "TEMPO" is the chemical 2,2,6,6-tetramethylpiperidinyloxy.

The term "sulfur trioxide pyridine complex" is the chemical $SO_3$-pyridine with a Chemical Abstracts Service (CAS) Registry Number® of 26412-87-3 and is available from Sigma-Aldrich Co. (catalogue number S7556).

The term "3-Hydroxy-pyran-4-one" refers to the following heterocycle

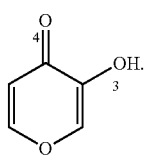

The term "3-Hydroxy-1-methyl-1H-pyridin-4-one" refers to the following heterocycle

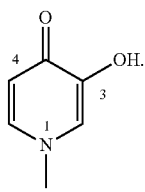

The term "3-Hydroxy-1H-pyridin-4-one" refers to the following heterocycle

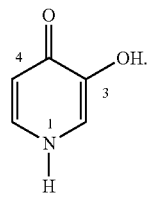

One class of preferred compounds according to the present invention includes compounds having the general formula (II):

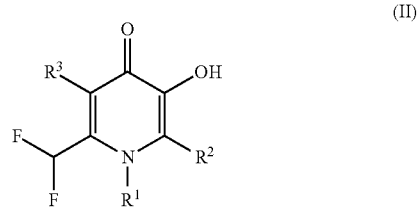

(II)

or their pharmaceutically acceptable salts, wherein $R^1$, $R^2$ and $R^3$ are as previously defined.

Another class of preferred compounds according to the present invention includes compounds having the general formula (III):

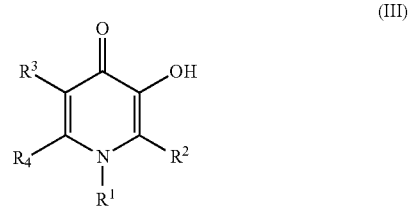

(III)

or their pharmaceutically acceptable salts, wherein $R^1$, $R^2$, $R^3$ and $R^4$ are as previously defined.

Another class of preferred compounds according to the present invention includes compounds having the general formula (IIIC)

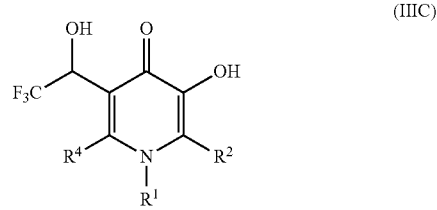

(IIIC)

or their pharmaceutically acceptable salts, wherein, $R^1$, $R^2$ and $R^4$ are as previously defined.

A further class of preferred compounds according to the present invention includes compounds having the general formula (IV):

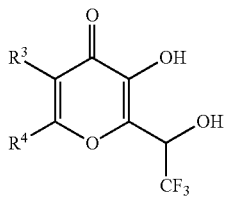

(IV)

or their pharmaceutically acceptable salts, wherein $R^3$ and $R^4$ are as previously defined.

Compounds according to the present invention include compounds having the general formula (I):

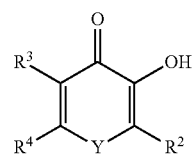

(I)

which are more specifically identified in the following table:

|  | $R^4$ | $Y = NR^1$ | $R^3$ | $R^2$ | General Structure |
|---|---|---|---|---|---|
| Apo6729 | Me | Me | H | CH(OH)CF$_3$ | |
| Apo6814 | Me | H | H | CH(OH)CF$_3$ | |
| Apo6802 | CF$_2$H | Me | H | CH(OH)CF$_3$ | |
| Apo6827 | H | Me | H | CH(OH)CF$_3$ | |
| Apo6965 | CH(OH)CF$_3$ | Me | H | H | |
| Apo6966 | CH(OH)CF$_3$ | Me | H | CH$_2$OH | |
| Apo6987 | CH(OH)CF$_3$ | Me | H | Me | |
| Apo6762 | Me | Me | H | CH$_2$CF$_3$ | |
| Apo6825 | H | Me | H | CH$_2$CF$_3$ | |
| Apo6997 | Me | H | H | CH$_2$CF$_3$ | |
| Apo6986 | CH$_2$CF$_3$ | Me | H | H | |
| Apo6990 | CH$_2$CF$_3$ | Me | H | CH$_2$OH | |
| Apo6991 | CH$_2$CF$_3$ | Me | H | Me | |
| Apo6855 | H | Me | CH$_2$CF$_3$ | Me | |
| Apo6856 | H | H | CH$_2$CF$_3$ | Me | |

-continued

| | R⁴ | Y = NR¹ | R³ | R² | General Structure |
|---|---|---|---|---|---|
| Apo6719 | CF₂H | CH₃ | H | H | |
| Apo6736 | CF₂H | CH₃ | H | CH₂OH | |
| Apo6757 | CF₂H | CH₃ | H | CH(OH)CH₃ | |
| Apo6732 | CF₂H | CH₂CH₃ | H | H | |
| Apo6756 | CF₂H | C—Pr | H | H | |
| Apo6742 | CF₂H | CH₃ | H | CH₃ | |
| Apo6727 | CF₂H | Allyl | H | H | |
| Apo6761 | CF₂H | CH₃ | H | CH₂CH₃ | |
| Apo6725 | CF₂H | CH₂—cPr | H | H | |
| Apo6802 | CF₂H | CH₃ | H | CH(OH)CF₃ | |
| Apo6804 | CF₂H | H | H | H | (II) |
| Apo6854 | H | Me | CH(OH)CF₃ | Me | |
| Apo6803 | H | H | CH(OH)CF₃ | Me | |

(IIIc)

The preferred compounds according to the present invention are chemically stable with log $k_{BMC}$ values higher than that of deferiprone, and are stable in pH 7.4 phosphate buffer and 0.01 M sodium hydroxide solution.

FIG. 1 provides a table illustrating the physical properties of selected compounds of formula (I) according to the present invention. $D_{7.4}$ is the distribution coefficient of the compound in octanol and pH 7.4 phosphate buffer and is a measure of the lipophilicity of the compound in a chemical system. This parameter can be used to predict the ability of the compounds to penetrate the cell. The technique of Escuder-Gilabert et al. (Escudar-Gilabert, L., et al., Journal of Chromatography B, 2004, 807, 193-201) is used to predict the drug penetration across the BBB. Log $k_{BMC}$ is the logarithm of the chromatographic capacity factor (reference retention time) in BMC, a special type of HPLC. The chromatographic capacity factor $k_{BMC}$ of 31 reference drug substances with known experimentally determined log BB values were recorded (FIGS. 2 and 3). BB is known as the blood brain partition coefficient and is defined as the parts of the drug in the brain versus the parts of the drug in the blood. We found that the log BB values of the 31 reference drug substances are proportional to the log $k_{BMC}$ values and follow the mathematical equation: log BB=−0.98+ log $k_{BMC}$ with $r^2$=0.72. $r^2$ is the linear coefficient and reflects the quality of the data fit of log BB against log $k_{BMC}$. We used the above equation to compute a calculated log BB value of the compounds of the present invention as an estimate of the BBB penetration properties of the compounds. Deferiprone is known to penetrate the BBB and has a calculated log BB value of −1.05. All compounds of the present invention with a calculated log BB value>−1.05 will have BBB penetration properties. Although not bound by theory, a log BB value of −0.5 means that approximately 25% of the drug penetrates the BBB and gets into the brain (log BB=−0.5 implies a BB=0.32 [inverse log BB] and thus 1 part of the drug in the brain versus 3 parts of the drug in the blood).

FIG. 4 provides a table illustrating the chemical properties of a series of compounds of formula (I) according to the present invention. The definition of pKa₁ and pKa₂ is shown below:

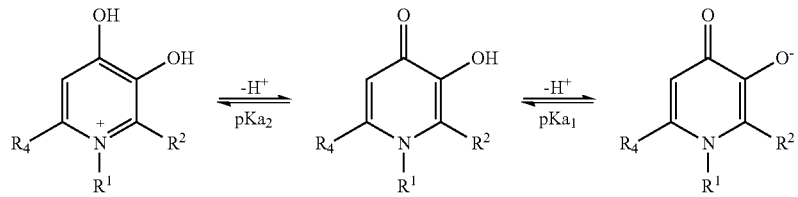

We have determined the pKa values of the compounds of formula (I) according to the present invention and have further determined the ferric complexation constant of the compounds. The metal complexation constant is defined below:

$K_1, K_2, K_3,$ and $\log\beta_3 = \log K_1 + \log K_2 + \log K_3$

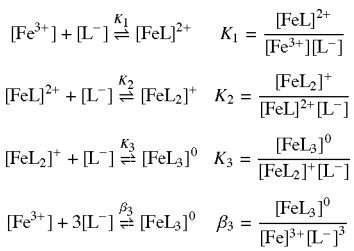

Figure 5:
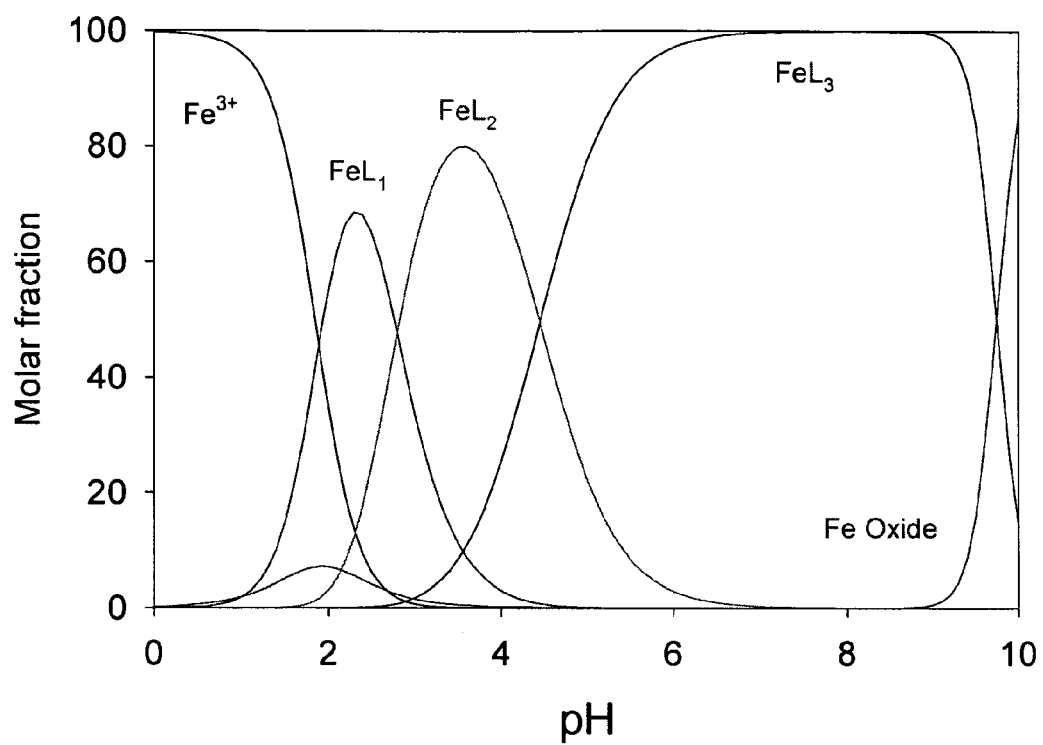
FIG. 5 is a speciation plot of Apo6719, a compound of formula (I) according to the present invention.

Compounds of the present invention are bidentate ligands and chelate Fe(III) in the ratio of 3:1. Therefore there are three complexation constants $K_1$, $K_2$ and $K_3$. $\beta_3$ is the overall complexation constant with Fe(III). With these parameters, one can compute the $pFe^{3+}$ of each chelator. $pFe^{3+}$ is $-\log [Fe^{3+}]$ (free unchelated ferric ion concentration) in a mixture of $1\times10^{-6}$ $Fe^{3+}$ and $1\times10^{-5}$ M chelator. For example, the drug deferiprone has a $pFe^{3+}$ of 20.2, and the published compound CP502 has a $pFe^{3+}$ of 21. Both chemicals are known to be extremely efficient in the removal of $Fe^{3+}$ from the body. Although not bound by theory, a compound with a $pFe^{3+}$ of about 19 and above is efficient in the removal of iron by the formation of $FeL_3$ wherein L is chelator. Computation shows that 100% of the ferric ion is chelated at a pH of about 7 to about 7.4 and there is no free available ferric ion to undergo redox cycle reactions to produce free radicals. FIG. 5 shows the speciation plot of Apo6719, a compound of formula (I) according to the present invention. A $pFe^{3+}$ of 19.7 assures that the compound is effective as an iron chelator in the removal of iron. The x axis is the pH. The y axis shows the molar fraction of the different components of the bidentate chelator. $FeL_3$ refers to one $Fe^{3+}$ is bound by three molecules of the ligand L, which is Apo6719 in this figure. As shown in FIG. 5, at a pH of about 7 to about 9, all of the free iron is bound by the chelator as $FeL_3$.

The chemical stability of fluorinated derivatives of deferiprone was evaluated. For example, the mono fluoro derivative of the formula (V) is unstable in pH 7.4 phosphate buffer and 0.01M sodium hydroxide. The products of decomposition are compounds (VA) and (VB).

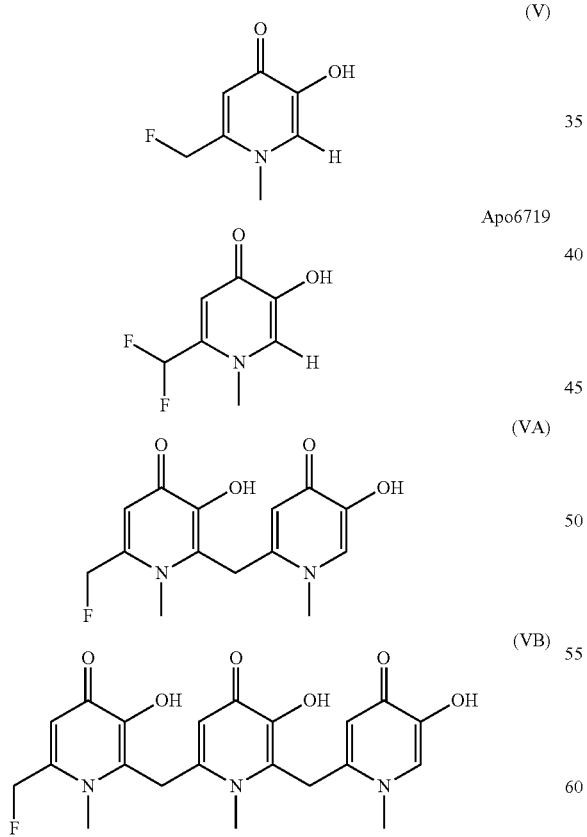

We determined that the difluoro derivative Apo6719 is stable under similar conditions.

The C2-difluoro derivatives of the formulas (VI) and (VII) according to the present invention are also unstable in pH 7.4 phosphate buffer and in 0.01 M sodium hydroxide. Compound (VI) decomposes to give compound (VIA), which is a stable chemical compound that exists as the hydrated aldehyde. Therefore, the compounds (VI) and (VII) are prodrugs to the hydrated aldehyde (VIA) and (VIIA) respectively. Their usefulness is in the role as a prodrug and not as an intact fluorinated 3-hydroxy-4-pyridinone derivative.

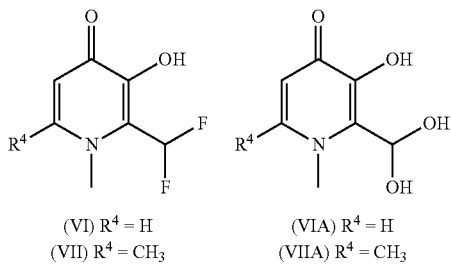

(VI) $R^4 = H$     (VIA) $R^4 = H$
(VII) $R^4 = CH_3$     (VIIA) $R^4 = CH_3$

Hydrolysis of the difluoro group of a 2-difluoromethyl-3-hydroxy-4-pyridinone derivative, wherein hydrogen is attached to the ring nitrogen, to an aldehyde with trifluoroacetic acid can be found in Example 75 of EP 0 336 369 A1.

We have also prepared the compound of formula (VIII) wherein $R^4$ is methyl. The compound (VIIIA) could be prepared, but catalytic hydrogenation resulted in the loss of the fluoride group at the C2 substituent of the 3-hydroxy-4-pyridinone to give compound (VIIIB). Reaction of compound (VIIIA) with 4M hydrochloric acid gives compound (VIIIC).

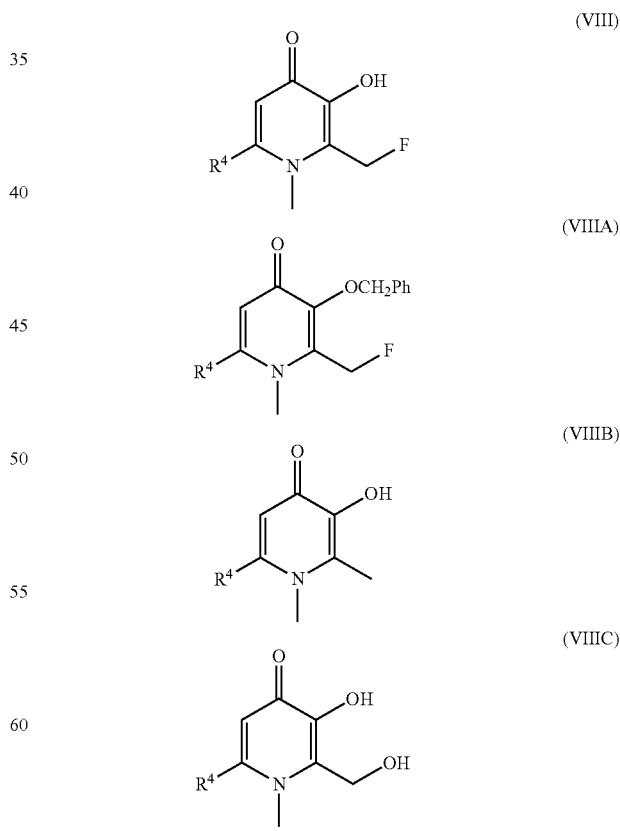

Thus it is not obvious to a person skilled in the art to design fluorinated analogues of deferiprone with the required parameters such as chemical stability, an acceptable $pFe^{3+}$, and better BBB penetration properties than deferiprone.

We determined that compounds of formula (I) according to the present invention wherein $R^4$ is $CHF_2$ are stable in pH 7.4 buffer, sodium hydroxide, deionized water and methanol. Other compounds of formula (I) according to the present invention wherein $R^2$ is selected from the group consisting of $CF_3CHOH$ and $CH_2CH_3$ are stable under similar conditions. With the exception of compounds (VI) and (VII) that are prodrugs, the compounds of formula (I) according to the present invention are stable fluorinated derivatives in a chemical system with high $pFe^{3+}$ values above about 19 and high predicted log BB values. The latter assures that the compounds of formula (I) according to the present invention will penetrate the BBB upon dosing to mammals.

Preferred compounds of formula (II) according to the present invention are those in which $R^1$ is selected from the group consisting of methyl, ethyl, allyl, cyclopropyl and cyclopropylmethyl; $R^2$ is selected from the group consisting of hydrogen, methyl, ethyl, —$CH_2OH$ and $CH_3CH(OH)$—; and $R^3$ is hydrogen. Particularly preferred compounds of formula (II) according to the present invention are those in which $R^1$ is selected from the group consisting of methyl and cyclopropyl; $R^2$ is selected from the group consisting of hydrogen, methyl and ethyl; and $R^3$ is hydrogen.

Preferred compounds of formula (III) according to the present invention are those in which $R^3$ is hydrogen, $R^4$ is selected from the group consisting of hydrogen and methyl, $R^1$ is as defined above, and $R^2$ is selected from the group consisting of $CF_3CH_2$ and $CF_3CH(OH)$—.

Particularly preferred compounds of formula (III) according to the present invention are those in which $R^2$ is selected from the group consisting of $CF_3CH_2$ and $CF_3CH(OH)$—, $R^3$ is hydrogen, $R^4$ is selected from the group consisting of hydrogen and methyl, and $R^1$ is methyl.

Preferred compounds of formula (IV) according to the present invention are those in which $R^2$ is $CF_3CH(OH)$— and $R^3$ and $R^4$ are each hydrogen.

"Pharmaceutically acceptable, non-toxic salts" refers to pharmaceutically acceptable salts of the compounds of the present invention which retain the biological activity of the parent compounds and are not biologically or otherwise undesirable (e.g. the salts are stable). Salts of two types may be formed from the compounds of the present invention: (1) salts of inorganic and organic bases from compounds of formulas (I), (II), (III), (IIIC) and (IV) which have a 3-hydroxy functional group in the 3-hydroxy-4-pyridinone skeleton; and (2) acid addition salts may be formed at the N1-amine functional group of compounds of formulas (II), (III) and (IIIC) of the present invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts.

Pharmaceutically acceptable acid addition salts are formed with inorganic acids such as halo acids, sulfuric acid, nitric acid, phosphoric acid and the like and organic acids such as methanesulfonic acid, ethanesulfonic acid, p-toluenesulfonic acid and the like.

The term "animals" refers to humans as well as all other animal species, particularly mammals (e.g. dogs, cats, horses, cattle, pigs, etc.), reptiles, fish, insects and helminths.

The specific most preferred compounds according to the present invention are the following:

2-difluoromethyl-5-hydroxy-1-methyl-1H-pyridin-4-one

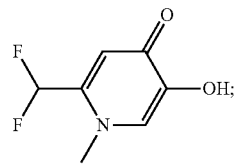

1-cyclopropyl-2-difluoromethyl-5-hydroxy-1H-pyridin-4-one

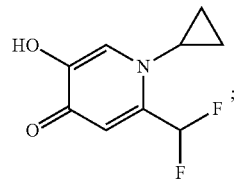 [SMILES: O=c1cc(C(F)F)n(C2CC2)cc1O]

1-cyclopropylmethyl-2-difluoromethyl-5-hydroxy-1H-pyridin-4-one

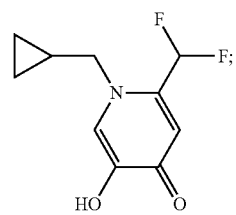 [SMILES: O=c1cc(C(F)F)n(CC2CC2)cc1O]

1-allyl-2-difluoromethyl-5-hydroxy-1H-pyridin-4-one

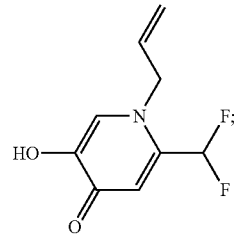

2-difluoromethyl-1-ethyl-5-hydroxy-1H-pyridin-4-one

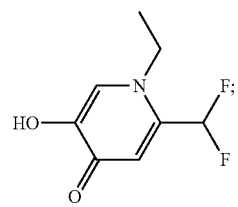

6-difluoromethyl-2-ethyl-3-hydroxy-1-methyl-1H-pyridin-4-one

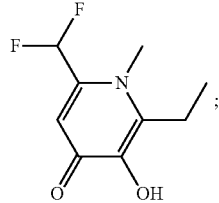

6-difluoromethyl-3-hydroxy-2-(1-hydroxy-ethyl)-1-methyl-1H-pyridin-4-one

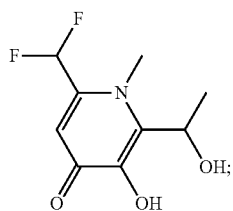

6-difluoromethyl-3-hydroxy-2-hydroxymethyl-1-methyl-1H-pyridin-4-one

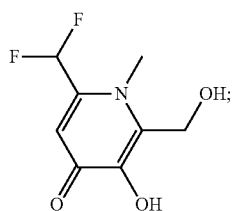

6-difluoromethyl-3-hydroxy-1,2-dimethyl-1H-pyridin-4-one

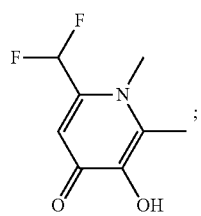

3-hydroxy-1,6-dimethyl-2-(2,2,2-trifluoro-1-hydroxy-ethyl)-1H-pyridin-4-one

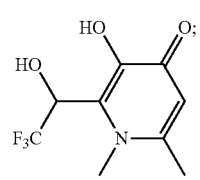 [SMILES: Cc1cc(=O)c(O)c(C(O)C(F)(F)F)n1C]

3-hydroxy-1,6-dimethyl-2-(2,2,2-trifluoro-ethyl)-1H-pyridin-4-one

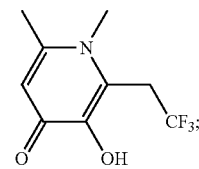

3-hydroxy-1-methyl-2-(2,2,2-trifluoro-ethyl)-1H-pyridin-4-one

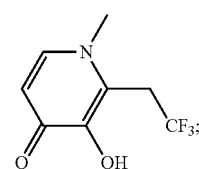

2-difluoromethyl-3-hydroxy-1,6-dimethyl-1H-pyridin-4-one

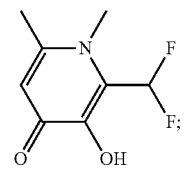

6-difluoromethyl-3-hydroxy-1-methyl-2-(2,2,2-trifluoro-1-hydroxy-ethyl)-1H-pyridin-4-one

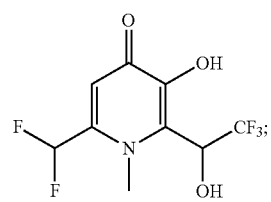 [SMILES: Cn1c(C(F)F)cc(=O)c(O)c1C(O)C(F)(F)F]

3-hydroxy-6-methyl-2-(2,2,2-trifluoro-1-hydroxy-ethyl)-1H-pyridin-4-one

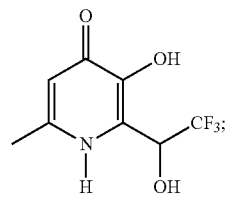

3-hydroxy-2-methyl-5-(2,2,2-trifluoro-1-hydroxy-ethyl)-1H-pyridin-4-one

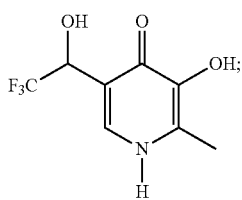

3-hydroxy-6-methyl-2-(2,2,2-trifluoro-1-hydroxy-ethyl)-pyran-4-one

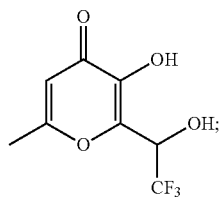

and
2-difluoromethyl-5-hydroxy-pyran-4-one;

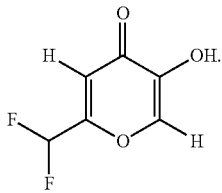

In accordance with another aspect of the present invention, there is provided a method for the preparation of a compound of formula (II)

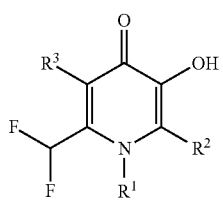

wherein:
R$^1$ is selected from the group consisting of hydrogen, C$_1$-C$_6$ alkyl (preferably C$_1$-C$_4$ alkyl), cyclopropylmethyl, allyl and cyclopropyl;
R$^2$ is selected from the group consisting of hydrogen, C$_1$-C$_6$ alkyl (preferably C$_1$-C$_4$ alkyl) and R$^5$CHOH wherein R$^5$ is selected from the group consisting of hydrogen, C$_1$-C$_6$ alkyl (preferably C$_1$-C$_3$ alkyl) and trifluoromethyl;
R$^3$ is selected from the group consisting of methyl, hydrogen and CF$_3$CHOH; and wherein the method comprises the following processes:
Process (A) which comprises the following steps:

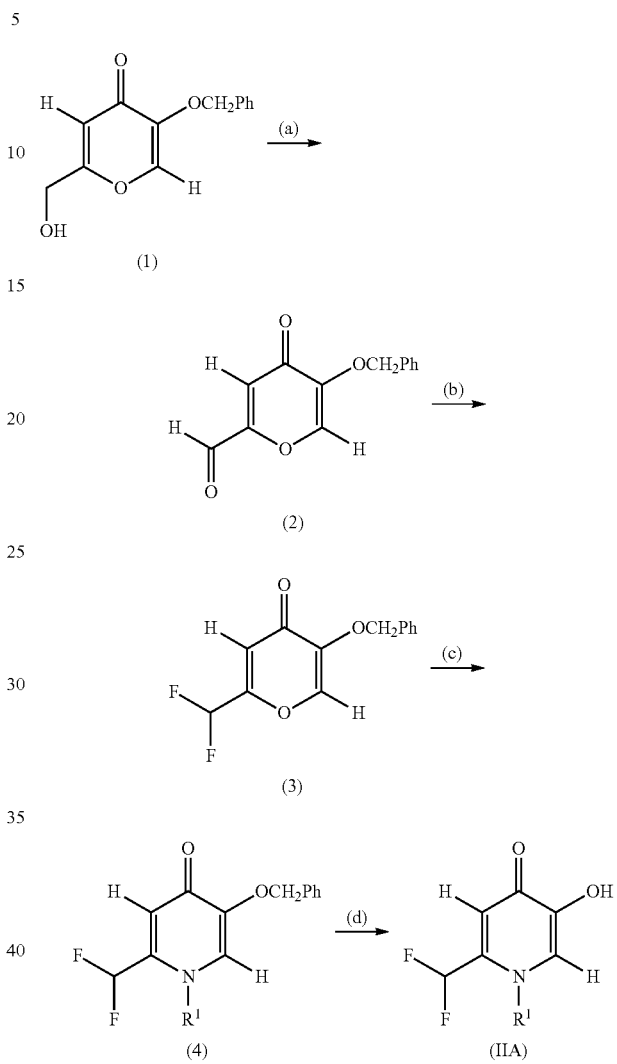

(a) oxidation of a compound (1) with an oxidating agent selected from the group consisting of TEMPO, potassium bromate, sodium hypochlorite and sulfur trioxide pyridine complex to give compound (2);
(b) reacting compound (2) from step (a) with DAST to give compound (3);
(c) reacting compound (3) with an amine of the formula R$^1$NH$_2$ wherein R$^1$ is selected from the group consisting of hydrogen, C$_1$-C$_6$ alkyl (preferably C$_1$-C$_4$ alkyl), allyl, cyclopropyl and cyclopropylmethyl to give compound (4) wherein R$^1$ is defined as in R$^1$NH$_2$; and
(d) hydrogenation of compound (4) with palladium on charcoal to give a compound of formula (IIA) (a compound of formula (II) when R$^2$ and R$^3$ are each hydrogen), with the proviso that when R$^1$ in compound (4) is allyl, boron tribromide is used instead of catalytic hydrogenation;

or

Process (B) which comprises the following steps:

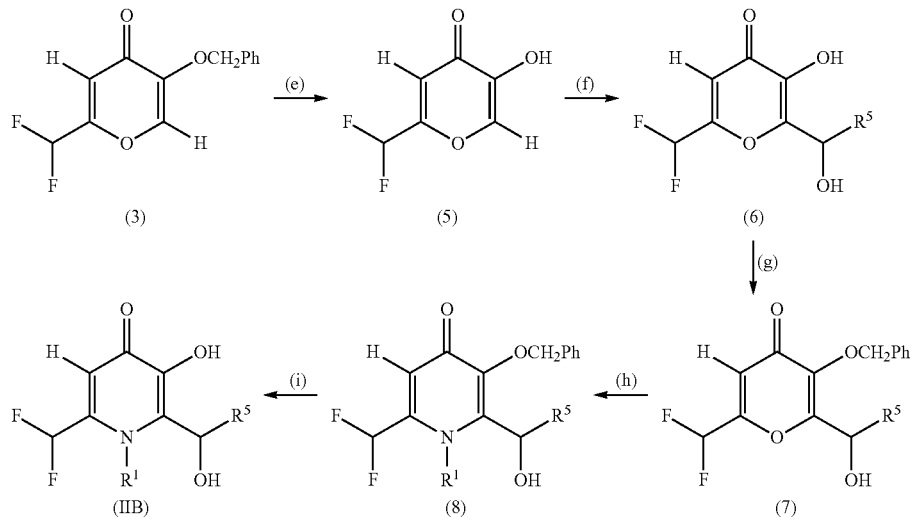

(e) debenzylation of compound (3) from Process (A), step (b), with BBr$_3$ to give compound (5);

(f) reacting compound (5) with an aliphatic aldehyde R$^5$CHO, wherein R$^5$ is selected from the group consisting of hydrogen and C$_1$-C$_6$ alkyl (preferably C$_1$-C$_3$ alkyl) alkyl, to give compound (6) wherein R$^5$ is as defined above;

(g) reacting compound (6) with benzyl bromide and sodium hydroxide to give compound (7) wherein R$^5$ is as defined above;

(h) reacting compound (7) with an amine of the formula R$^1$NH$_2$, wherein R$^1$ is selected from the group consisting of hydrogen, C$_1$-C$_6$ alkyl (preferably C$_1$-C$_4$ alkyl), allyl, cyclopropyl and cyclopropylmethyl, to give compound (8) wherein R$^1$ is as defined in R$^1$NH$_2$; and (i) hydrogenation of compound (8) with palladium on charcoal to give a compound of formula (IIB) (a compound of formula (II) when R$^2$ is R$^5$CHOH), with the proviso that R$^1$ is not allyl;

or

Process (C) which comprises the following steps:

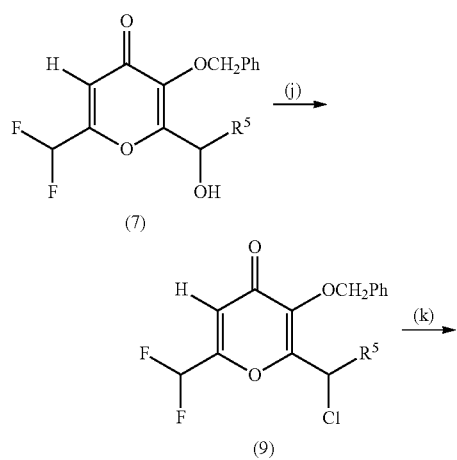

-continued

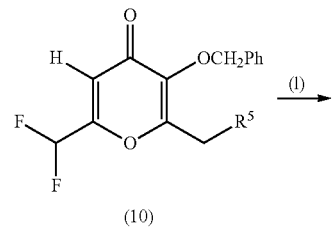

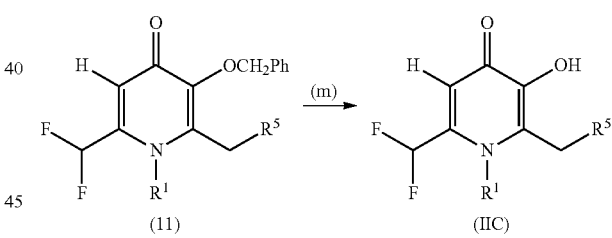

(j) reacting compound (7) from Process (B), step (g), with thionyl chloride to give the chloride (9) wherein R$^5$ is defined as above;

(k) reduction of compound (9), prepared from step (j) in situ, without isolation, with zinc in hydrochloric acid to give compound (10);

(l) reacting compound (10) from step (k) with an amine of the formula R$^1$NH$_2$ wherein R$^1$ is selected from the group consisting of hydrogen, C$_1$-C$_6$ alkyl (preferably C$_1$-C$_4$ alkyl), allyl, cyclopropyl and cyclopropylmethyl to give compound (11) wherein R$^1$ is as defined in R$^1$NH$_2$; and (m) hydrogenation of compound (11) from step (l) with palladium on charcoal to give a compound of formula (IIC) (a compound of formula (II) when R$^2$ is CH$_2$R$^5$), with the proviso that R$^1$ is not allyl;

or
Process (D) which comprises the following steps:

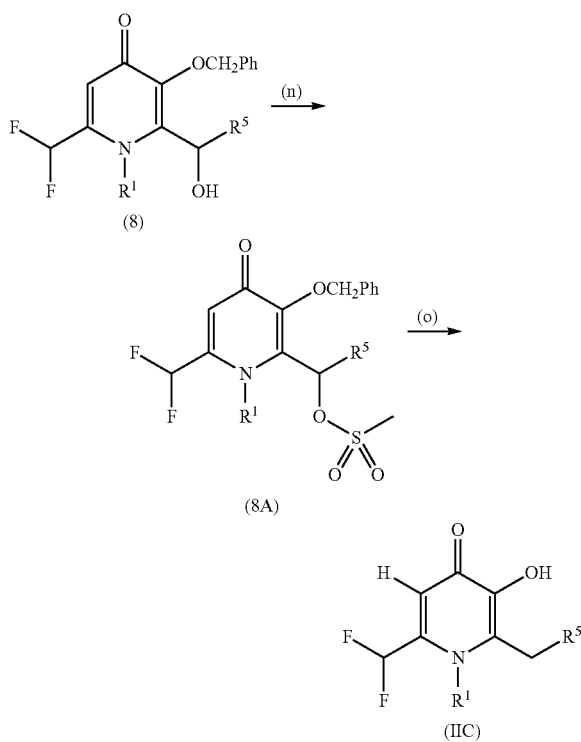

(n) reacting compound (8) from Process (B), step (h), wherein $R^5$ is hydrogen with triethylamine and methanesulfonyl chloride to give compound (8A); and
(o) hydrogenation of compound (8A) with palladium on charcoal to give a compound of formula (IIC) (a compound of formula (II) when $R^2$ is $CH_2R^5$), wherein $R^5$ is hydrogen and with the proviso that $R^1$ is not allyl;
or
Process (E) which comprises the following steps:

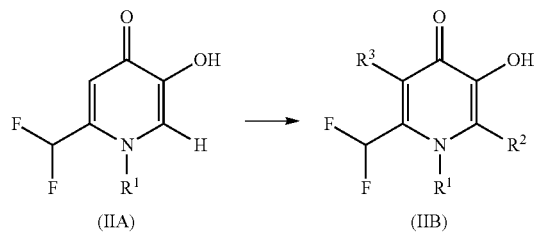

reacting a compound of formula (IIA) with $CF_3CH(O-C_1-C_4$ linear alkyl)OH, preferably $CF_3CH(OCH_3)OH$ or $CF_3CH(OCH_2CH_3)OH$, and most preferably $CF_3CH(OCH_3)OH$, in the presence of potassium carbonate at a temperature of about 100° C. to about 130° C. to give a compound of formula (IIB) wherein $R^3$ is hydrogen, and $R^2$ is $R^5CHOH$ wherein $R^5$ is trifluoromethyl.

In Process (A), step (a), compound (1) is oxidized with TEMPO and sodium hypochlorite to give the aldehyde (2). Although other oxidizing agents such as the Swern oxidation can be used, the preferred method of oxidation is the TEMPO oxidation because there are no sulphur by-products and sodium hypochlorite is easily available. Reaction of (2) with DAST ($Et_2NSF_3$) converts the aldehyde (2) to the C2-difluoromethyl derivative (3), which then undergoes amine insertion of $R^1NH_2$ to give the protected 3-hydroxy-4-pyridinone (4) in an inert solvent such as dimethylformamide or ethanol. Compound (4) is hydrogenated in ethanol or methanol with palladium on charcoal to give the compound of formula (IIA). When $R^1$=allyl in compound (4), the O-benzyl group is removed by treatment with boron tribromide instead of catalytic hydrogenation to avoid the reduction of the double bond at the allyl group.

In Process (B), compound (3) is used as the starting material. Catalytic hydrogenation affords the 3-hydroxy derivative (5) which reacts with an aliphatic aldehyde $R^5CHO$ to give compound (6). The direct conversion of compound (6) to a compound of formula (IIB) is not possible via amine insertion of $R^1NH_2$. Rather, compound (6) is again protected in step (g) with sodium hydroxide and benzyl bromide to give compound (7). Compound (7) undergoes amine insertion to give compound (8), which can be converted to a compound of formula (IIB) by catalytic hydrogenation with palladium on charcoal.

In Process (C), compound (7) is treated with thionyl chloride to give compound (9) in situ. Without isolation, zinc metal reduction with hydrochloric acid produces compound (10). Amine insertion with $R^1NH_2$ gives compound (11), and catalytic hydrogenation produces a compound of formula (IIC).

In Process (D), compound (8) is reacted with triethylamine and methanesulfonyl chloride to give compound (8A). Without isolation, compound (8A) is hydrogenated over palladium on charcoal in the presence of acetic acid to give a compound of formula (IIC).

In Process (E), a compound of formula (IIA) is reacted with $CF_3CH(O-C_1-C_4$ linear alkyl)OH, preferably $CF_3CH(OCH_3)OH$ or $CF_3CH(OCH_2CH_3)OH$, and most preferably $CF_3CH(OCH_3)OH$, in the presence of potassium carbonate at a temperature of about 100° C. to about 130° C. in a sealed tube to give a compound of formula (IIB) wherein $R^3$ is hydrogen and $R^2$ is $R^5CHOH$ wherein $R^5$ is trifluoromethyl.

In Process (B), step (i) hydrogenation will convert a compound (8) wherein $R^1$ is allyl to a compound of formula (IIB) wherein $R^1$ is propyl. In Process (C), step (m) hydrogenation will convert a compound (11) wherein $R^1$ is allyl to a compound of formula (IIC) wherein $R^1$ is propyl. In Process (D), step (o) hydrogenation will convert a compound (8A) wherein $R^1$ is allyl to a compound of formula (IIC) wherein $R^1$ is propyl.

In accordance with another aspect of the present invention, there is provided a method for the preparation of a compound of formula (III)

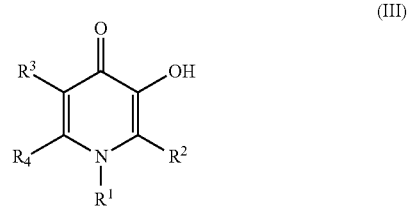

wherein:
$R^1$ is selected from the group consisting of hydrogen, $C_1$-$C_4$alkyl, allyl, cyclopropyl and cyclopropylmethyl;
$R^4$ is selected from the group consisting of methyl and hydrogen;

$R^3$ is selected from the group consisting of methyl and hydrogen;

$R^2$ is selected from the group consisting of $CF_2$, $CF_3CHOH$ and $CF_3CH_2$; and wherein the method comprises the following steps:

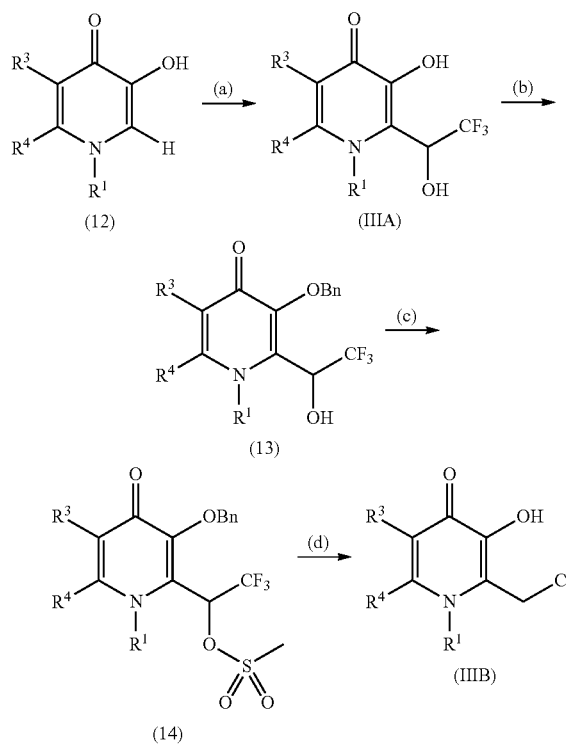

(a) reaction of compound (12) with $CF_3CH(O—C_1-C_4$ linear alkyl)OH, preferably $CF_3CH(OCH_3)OH$ or $CF_3CH(OCH_2CH_3)OH$, and most preferably $CF_3CH(OCH_3)OH$, to give a compound of formula (IIIA) (a compound of formula (III) wherein $R^2$ is $CF_3CH(OH)$);

(b) reacting the product of formula (IIIA) from step (a) with benzyl bromide and sodium hydroxide to give compound (13) wherein $R^3$, $R^4$ and $R^1$ are defined as above;

(c) converting compound (13) into the methanesulfonate (14) with methanesulfonyl chloride and triethylamine, wherein $R^1$, $R^3$ and $R^4$ are as defined as above; and (d) hydrogenation of compound (14) in the presence of palladium on charcoal to give a compound of formula (IIIB) (a compound of formula (III) wherein $R^1$ is selected from the group consisting of $C_1$-$C_4$ alkyl, cyclopropyl and cyclopropylmethyl; $R^4$ is selected from the group consisting of methyl and hydrogen; $R^3$ is hydrogen; and $R^2$ is $CF_3CH_2$), with the proviso that $R^1$ is not allyl.

The 3-hydroxy-4-pyridinone (12) reacts with $CF_3CH(O—C_1-C_4$ linear alkyl)OH, preferably $CF_3CH(OCH_3)OH$ or $CF_3CH(OCH_2CH_3)OH$, and most preferably $CF_3CH(OCH_3)OH$, and potassium carbonate to give a compound of formula (IIIA). It should be noted that the reaction of compound (12) with an aliphatic aldehyde to give a compound of formula (IIIA) directly is unknown in the literature. In the traditional approach, the aldehyde reaction is carried out with the 3-hydroxy-4-pyranone (15) to give compound (16), followed by O-benzylation of compound (16) to give compound (17). The amine insertion of compound (17) with $R^1NH_2$ normally gives the protected derivative (13), which is then hydrogenated to give the compound of formula (IIIA). We have determined that compound (17) does not readily undergo amine insertion to give compound (13) in good yield. Therefore, the present invention provides a novel and direct synthesis of compound (IIIA) using a one step reaction from compound (12). Compound IIIA is protected in step (b) with benzyl bromide and sodium hydroxide to give compound (14). Compound (14) is converted into the methanesulfonate (15) with methanesulfonyl chloride and triethylamine. Catalytic hydrogenation with palladium on charcoal produces the compound of formula (IIIB). In step (b) above, hydrogenation will convert compound (14) wherein $R^1$ is allyl to a compound of formula (IIIB) wherein $R^1$ is propyl.

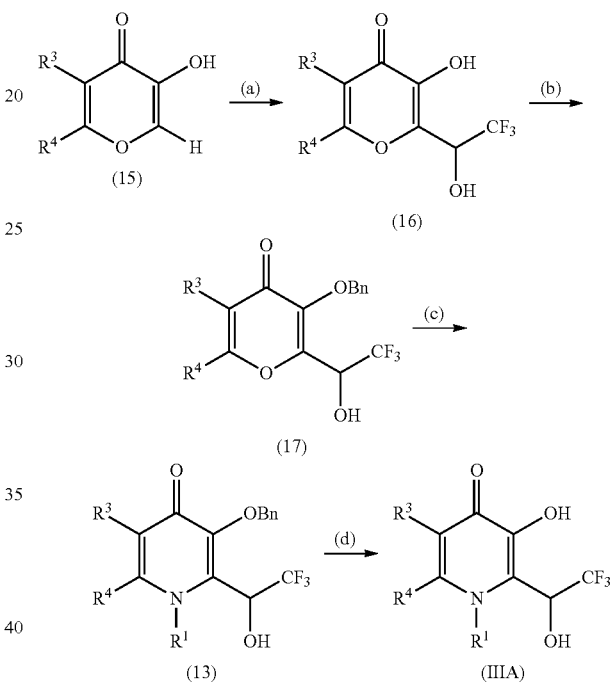

In accordance with another aspect of the present invention, there is provided a process for the preparation of a compound of formula (IV) wherein Y is O; $R^3$ is selected from the group consisting of hydrogen and methyl; $R^4$ is selected from the group consisting of hydrogen and $C_1$-$C_6$ alkyl (preferably $C_1$-$C_4$ alkyl); and $R^2$ is $CF_3CHOH$,

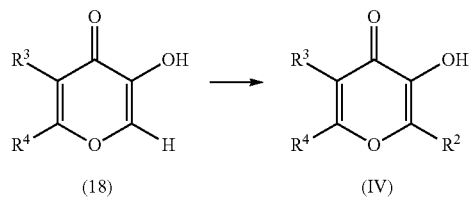

wherein the process comprises reacting compound (18), wherein $R^4$ is selected from the group consisting of hydrogen and $C_1$-$C_6$ alkyl (preferably $C_1$-$C_4$ alkyl) and $R^3$ is selected from the group consisting of hydrogen and methyl, with $CF_3CH(O—C_1-C_4$ linear alkyl)OH, preferably $CF_3CH(OCH_3)OH$ or $CF_3CH(OCH_2CH_3)OH$, and most preferably $CF_3CH(OCH_3)OH$, in the presence of potassium carbonate.

The synthesis of a compound of formula (IV) is illustrated in Example 12 below.

In accordance with another aspect of the present invention, there is provided a process for preparing a compound of formula (I),

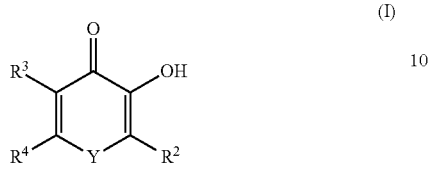

(I)

wherein Y is O, $R^3$ is hydrogen, $R^2$ is hydrogen, and $R^4$ is $CHF_2$, the compound being 2-difluoromethyl-5-hydroxy-pyran-4-one, and wherein the process comprises the following steps:
(a) reacting kojic acid with sodium hydroxide and benzyl bromide to give 5-benzyloxy-2-hydroxymethyl-pyran-4-one;
(b) oxidizing the compound from step (a) with TEMPO, sodium hypochlorite and potassium bromate or with sulfur trioxide pyridine complex to give 5-benzyloxy-4-oxo-4H-pyran-2-carbaldehyde;
(c) reacting the compound from step (b) with DAST to give 5-benzyloxy-2-difluoromethyl-pyran-4-one; and
(d) reacting the compound from step (c) with boron tribromide to give 2-difluoromethyl-5-hydroxy-pyran-4-one.

The synthesis of 2-difluoromethyl-5-hydroxy-pyran-4-one, as discussed above, is illustrated in Example 4 below.

In accordance with another aspect of the present invention, there is provided a process for the preparation of a compound of the formula (IIIC)

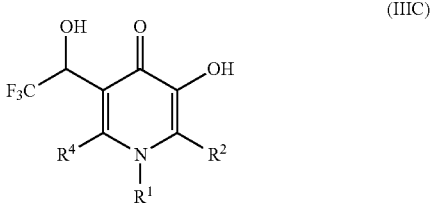

(IIIC)

wherein $R^1$ is selected from the group consisting of hydrogen, $C_1$-$C_6$ alkyl (preferably $C_1$-$C_4$ alkyl), allyl, cyclopropyl and cyclopropylmethyl;
$R^2$ is selected from the group consisting of hydrogen and $C_1$-$C_6$ alkyl (preferably $C_1$-$C_4$ alkyl), with the proviso that when $R^4$ is hydrogen, $R^2$ is not hydrogen; and
$R^4$ is selected from the group consisting of hydrogen and methyl; and
wherein the method comprises the following steps:

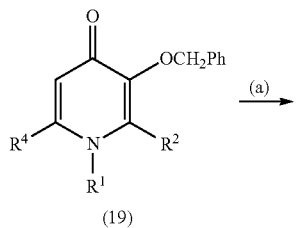

(19)

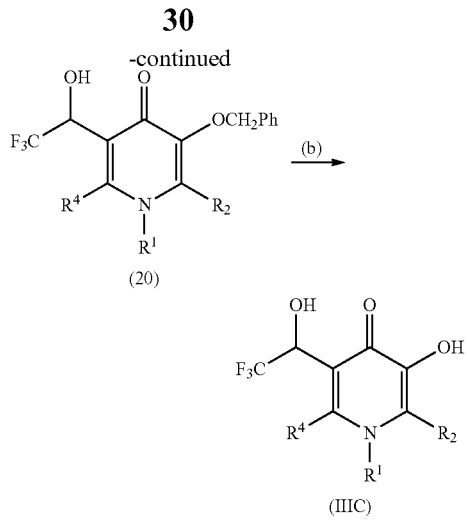

(a) reaction of compound (19) with $CF_3CH(O$—$C_1$-$C_4$ linear alkyl)OH, preferably $CF_3CH(OCH_3)OH$ or $CF_3CH(OCH_2CH_3)OH$, and most preferably $CF_3CH(OCH_3)OH$, to give compound (20); and
(b) hydrogenation of compound (20) in the presence of palladium on charcoal to give a compound of formula (IIIC), with the proviso that $R^1$ is not allyl.

Compound (19) is reacted with $CF_3CH(O$—$C_1$-$C_4$ linear alkyl)OH, preferably $CF_3CH(OCH_3)OH$ or $CF_3CH(OCH_2CH_3)OH$, and most preferably $CF_3CH(OCH_3)OH$, in the presence of potassium carbonate at a temperature of about 100° C. to about 130° C. in a sealed tube to give compound (20). Catalytic hydrogenation with palladium on charcoal produces the compound of formula (IIIC).

The synthesis of a compound of formula (IIIC) wherein $R^2$ is methyl and $R^4$ is hydrogen is illustrated in Example 19 below.

Certain compounds of the present invention may be converted to their corresponding pharmaceutically acceptable acid addition salts by virtue of the presence of a basic amine nitrogen. These compounds may be converted from the free base form to various acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as p-dioxane or dimethoxyethane, and the acid added thereto. The temperature is maintained from about 0° C. to about 50° C. The resulting acid addition salt precipitates spontaneously or may be precipitated out of solution with a less polar solvent. These acid addition salts may be decomposed to the corresponding free base by treating with a stoichiometric amount of a suitable base, such as potassium carbonate or sodium hydroxide, typically in the presence of aqueous solvent, and at a temperature of from about 0° C. to about 50° C. The free base form is isolated by conventional means, such as extraction with an organic solvent. Acid addition salts of the compounds of the present invention may be interchanged by taking advantage of differential solubilities of the salts, volatilities or acidities of the acids, or by treating with an appropriately loaded ion exchange resin. For example, the interchange is effected by the reaction of a salt of the compounds of formula (I) with a slight stoichiometric excess of an acid of a lower pKa than the acid component of the starting salt. This is carried out at a temperature of from about 0° C. to about the boiling point of the solvent being used.

For the treatment of diseases and/or disorders herein above referred to, the compounds of the present invention may be used orally or parenterally in formulations containing conventional non-toxic pharmaceutically acceptable carriers, adjuvants and vehicles. The term parenteral as used herein includes subcutaneous injection or infusion techniques. In addition to the treatment of warm-blooded animals, such as mice, rats, horses, cattle, sheep, dogs, cats, etc., the compounds of the present invention are effective in the treatment of humans.

For compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compounds as defined above may be formulated as liquid pharmaceutically administrable compositions and can, for example, be prepared by mixing, dissolving, dispersing, etc. the active compounds as defined above the optional pharmaceutically adjuvants in a carrier, such as, for example, water, saline, aqueous dextrose, glycerol, ethanol, and the like, to hereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanolamine oleate, etc. Actual methods of preparing such dosage forms are known, or will be apparent to those skilled in this art: for example, see Remington: The Science and Practice of Pharmacy, $21^{st}$ Edition, 2006, Part 5, Pharmaceutical Manufacturing, Chapters 37, 39, 41-47 and 50, pp. 702-719, 745-775, 802-938, and 1000-1017 (formerly known as Remington's Pharmaceutical Sciences), David B. Troy (Ed.), Lipincott Williams & Wilkins, Baltimore, Md.

The composition or formulation to be administered will, in any event, contain a quantity of the active compounds in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known in the art for the manufacture of pharmaceutical compositions and such compositions contain one or more agents selected from the group consisting of sweetening agents, flavouring agents, colouring agents and preserving agents in order to provide pharmaceutically elegant and palatable preparations.

Tablets contain the active ingredient in admixture with the non-toxic pharmaceutically acceptable excipients which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be coated by known techniques to delay the disintegration and absorption in the gastrointestinal tract and thereby provide a sustained action over long period.

Formulations for oral use may also be presented as had gelatin capsules wherein the active ingredients are mixed with inert solid diluent, for example, calcium phosphate or kaolin, or as soft gelating capsules wherein the active ingredient is mixed with water or an oil medium, for example peanut oil, liquid paraffin, or olive oil.

Aqueous suspensions contain the active materials in admixture with the excipients suitable for the manufacture of aqueous suspensions. Such excipients are suspending agents, for example sodium carboxymethyl-cellulose, methylcellulose, hydroxypropylmethylcellulose, sodium alginate, polyvinylpyrrolidone, gum and gum acacia; dispersing or wetting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxy-benzoate, one or more colouring agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above. Additional recipients, for example sweetening, flavouring and colouring agents, may also be present.

The pharmaceutical composition of the present invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphates, esters derived from fatty acids and hexitol anhydrides, for example sorbitan monooleate, and condensation products of the said partial ester with ethylene oxide, for example polyoxyethylene sorbitan monooleate. The emulsion may also contain sweetening and flavouring agents.

Syrups and elixirs may be formulated with sweetening agents, for example glycerol, propylene glycol, sorbitol or sucrose. Such formulations may also contain a demulcent, a preservative, a flavouring agent and a colouring agent. The pharmaceutical compositions may be formulated according to methods known in the art using the suitable dispersing or wetting agents and suspending agents which have been mentioned above. The sterile injectable preparations may also be sterile injectable solutions or suspensions in a non-toxic parenterally-acceptable diluent or solvent, for example as a solution in 1,3-butanediol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation of injectables.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

The amounts of the active ingredients of the present invention that may be combined with the carrier materials to produce a single dosage form will vary depending upon the host treated and the particular mode of administration of humans may contain from about 0.5 mg to about 5 mg of active agent compounded with an appropriate amount of carrier material which may vary from about 5 to about 95% of the total composition. Unit dosage unit forms will generally contain from about 1 mg to about 500 mg of the active ingredients of the present invention.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

In vivo pharmacokinetic (PK) and blood brain barrier (BBB) studies were conducted in male Sprague-Dawley rats using cassette dosing. The topic of cassette dosing has been reviewed by Manitpisitkul, P. and White, R. E. (August 2004), Drug Discovery, Vol 9. No. 15, pp. 652-658. The mode of administration was through tail vein injection. The results are summarized in the Table below:

vacuum using a rotary evaporator, and a dense solid separated. The solid was collected by suction filtration, and the filtrate was set aside for further extraction.

The solid was slurried in a mixture of water (2 L) and acetone (200 mL), then collected by suction filtration and dried to constant weight under vacuum in an oven at 40° C. for overnight. The weight of this first crop of white solid product was 150.0 g.

The filtrate set aside above was diluted with water (300 mL). It was extracted with $CH_2Cl_2$ (3×500 mL). The combined organic fractions were dried over sodium sulfate, filtered and concentrated in vacuo to give a solid. The solid was slurried in water (200 mL) and acetone (20 mL), then collected and dried as described above for the first crop. The weight of this second crop of white solid product was 22.0 g. The two crops were combined to give a total yield of 74%. The purity (peak area percent: >95%) of this material was analysed by HPLC Method 1: Column: XTerra MS C18; 5 μm, 4.6×250 mm; Mobile phase: A=the aqueous phase: 8 mM Tris, 4 mM EDTA, pH 7.4; B=the organic phase: $CH_3CN$; gradient: % B: 0 min—5%, 15 min—55%, 15 to 25 min—55%, 25 to 30 min—5%; Flow rate: 1 mL/min; λ: 254, 280, 320, 450 nm; RT=retention time, given in the experimental wherever appropriate. $^1$H NMR (400 MHz, DMSO-$D_6$) δ (ppm): 8.18 (s, 1H), 7.35-7.43 (m, 5H), 6.33 (s, 1H), 5.70 (t, J=6.0 Hz, 1H, OH), 4.95 (s, 2H, $CH_2Ph$), 4.30 (d, J=5.6 Hz, 2H, $CH_2OH$).

| Compound | AUC brain* (μg-h/mL) | AUC plasma* (μg-h/mL) | AUC brain/AUC plasma | Kα (1/h) | Kβ (1/h) | $t_{1/2}α$ (h) | $t_{1/2}β$ (h) | Brain/Plasma ratio at 5 min |
|---|---|---|---|---|---|---|---|---|
| Deferiprone | 0.86 | 1.08 | 0.79 | 1.36 | 0.215 | 0.51 | 3.22 | 0.45 |
| Apo6825 | 2.73 | 4.52 | 0.60 | 0.68 | 0.133 | 1.02 | 5.21 | 0.46 |
| Apo6855 | 0.58 | 0.89 | 0.65 | 2.37 | 0.136 | 0.29 | 5.10 | 0.50 |

*normalized to 2 mg/kg dose
Apo6825 is a compound of formula I (group (vi)) wherein $R^3$ is hydrogen, $R^4$ is hydrogen, $R^2$ is $CH_2CF_3$, Y is $NR^1$ and $R^1$ is methyl.
Apo6855 is compound of formula I ((group (vi)) wherein $R^3$ is $CH_2CF_3$, $R^4$ is hydrogen, $R^2$ is methyl, Y is $NR^1$ and $R^1$ is methyl.
Deferiprone is 3-hydroxy-1,2-dimethyl-1H-pyridin-4-one and was used as a reference in the cassette dosing study.
Apo6825 achieves significantly higher brain exposure (AUC = 2.73 μg-h/mL) than deferiprone (AUC = 0.86 μg-h/mL). In addition, a two-fold improvement of the intrinsic $t_{1/2}α$ value of Apo6825 (1.02 h) over deferiprone (0.51 h) is observed.

Further details of the preferred embodiments of the present invention are illustrated in the following examples which are understood to be non-limiting with respect to the appended claims.

EXAMPLE 1

Preparation of
5-benzyloxy-2-hydroxymethyl-pyran-4-one

A 10M NaOH solution (110 mL, 1.10 mol) was added to a suspension of kojic acid (142.1 g, 1.00 mol) in methanol (1 L) with mechanical stirring at room temperature. Benzyl bromide (137.0 mL, 1.15 mol) was added, and the resulting clear yellow solution was refluxed using a heating mantle for 3 h. The progress of the reaction was monitored by TLC using a mixture of $CH_2Cl_2$ and MeOH (9/1, v/v) as eluant, and by HPLC (method 1). Most of the MeOH was removed under

EXAMPLE 2

Preparation of
5-benzyloxy-4-oxo-4H-pyran-2-carbaldehyde

Method 1-TEMPO oxidation: Solid $NaHCO_3$ (96.0 g, 1.21 mol) and deionized water (125 mL) were added to a mixture of 5-benzyloxy-2-hydroxymethyl-pyran-4-one (40.0 g, 0.17 mol) in $CH_2Cl_2$ (550 mL) and deionized water (200 mL). The mixture was cooled in an ice-salt bath to about 0° C. Then, $KBrO_3$ (4.00 g, 24.1 mmol), n-$Bu_4N^+Br^-$ (2.20 g, 6.90 mmol) and TEMPO (0.54 g, 3.44 mmol) were successively added. To the resulting heterogeneous mixture at 0° C. was added a solution of 1.59 M NaOCl (140 mL, 1.3 equiv) within 5-7 min. The reaction mixture turned to orange then to bright yellow during the NaOCl addition. The mixture was stirred for an additional 1-2 min, and then the solid was filtered off by suction filtration. The filtrate was placed in a separatory funnel, and the organic fraction was collected and dried over sodium sulfate. Analysis of the crude mixture by HPLC Method 1 (λ=280 nm), as described above, indicated the presence of the over-oxidized product (5-benzyloxy-4-oxo-4H-pyran-2-carboxylic acid, peak percent area: 6%, RT=9.42 min), the desired product (5-benzyloxy-4-oxo-4H-pyran-2-carbaldehyde, peak percent area is 85%, and its RT is 11.34 min) and the starting material (5-benzyloxy-2-hydroxymethyl-pyran-4-one, peak percent area is 8%, and its RT is 12.18 min).

The organic fraction was filtered and the volume was reduced to about 60 mL using the rotary evaporator. The mixture was placed on top of a wet-packed silica gel column, and eluted with ethyl acetate. The fractions containing the product were combined. Upon concentration on the rotary evaporator (volume reduction), the product separated out as a solid. The solid was collected by suction filtration to provide a first crop (10 g after drying under vacuum). The filtrate was collected and the volume of solvent reduced under vacuum. The precipitated solid was collected by filtration to give a second crop (5 g after drying under vacuum). The crops were combined to provide a 38% yield of the titled compound. The purity (peak area percent is 97.4%) of this material was analysed by HPLC Method 1 as described above. $^1$H NMR (400 MHz, DMSO-D$_6$) δ (ppm): 9.64 (s, 1H), 8.41 (s, 1H), 7.32-7.43 (m, 5H), 7.13 (s, 1H), 5.01 (s, 2H, CH$_2$Ph).

Method 2: sulfur trioxide pyridine complex oxidation: A suspension of 5-benzyloxy-2-hydroxymethyl-pyran-4-one (30.0 g, 0.129 mol) in CHCl$_3$ (500 mL) and CH$_2$Cl$_2$ (100 mL) was cooled in an ice-salt bath to about 0° C. DMSO (150 mL) and Et$_3$N (105 mL, 0.752 mol) were added, and a clear yellow solution was obtained. The mixture was stirred for about 30 min as the temperature reached to below 0° C. Then, sulfur trioxide pyridine crushed powder (105 g, 0.660 mol) was added portionwise over 30 min. No significant exotherm was observed as the reaction temperature read below 0° C. The progress of the reaction was monitored by TLC using a mixture of hexanes and ethyl acetate (1/1, v/v) as eluant. After 1 h, the cooling bath was removed, and the reaction mixture was allowed to stir at room temperature for overnight. The reaction mixture was diluted with CH$_2$Cl$_2$ (200 mL), then quenched with a 5% citric acid solution (150 mL). The organic fraction was washed again with 100 mL of the citric acid solution. Each of the aqueous acidic fractions were back-extracted with CH$_2$Cl$_2$ (2×100 mL), and all of the organic fractions were combined, dried over sodium sulfate, and purified as described in method 1 above. Thus, 13.4 g (45%) of the desired compound was obtained, and its $^1$H NMR was similar to the one described in method 1 above.

EXAMPLE 3

Preparation of
5-benzyloxy-2-difluoromethyl-pyran-4-one

To a clear solution of 5-benzyloxy-4-oxo-4H-pyran-2-carbaldehyde (10.0 g, 43.4 mmol) in CH$_2$Cl$_2$ (125 mL) was added DAST (8.40 g, 52.1 mmol) dropwise at room temperature. Soon after addition, TLC analysis of the reaction mixture using a mixture of hexanes and ethyl acetate (4/1, v/v) as eluant indicated consumption of the starting material. The reaction mixture was diluted with CH$_2$Cl$_2$ (80 mL), and quenched by the slow addition of a 10% NaHCO$_3$ solution (80 mL). Another portion of CH$_2$Cl$_2$ (125 mL) was added, and the mixture was left stirring for about 20 min. The organic fraction was collected, and the aqueous layer was extracted with CH$_2$Cl$_2$ (80 mL). The combined organic fractions were dried over sodium sulfate, filtered, and the volume was reduced using the rotary evaporator to about 30 mL. Purification of the residue by column chromatography on silica gel using a mixture of hexanes and ethyl acetate (4/1, v/v) as eluant afforded the title compound (5.02 g, 46% yield). $^1$H NMR (400 MHz, DMSO-D$_6$) δ (ppm): 8.40 (s, 1H), 7.35-7.43 (m, 5H), 6.96 (t, J=52.6 Hz, 1H, CF$_2$H), 6.77 (s, 1H), 4.98 (s, 2H, CH$_2$Ph).

EXAMPLE 4

Preparation of
2-difluoromethyl-5-hydroxy-pyran-4-one

To an ice-salt cooled, clear solution of 5-benzyloxy-2-difluoromethyl-pyran-4-one (252 mg, 1 mmol) in CH$_2$Cl$_2$ (4 mL) was added dropwise a solution of 1.0 M BBr$_3$ in CH$_2$Cl$_2$ (1 mL, 1 mmol) diluted with CH$_2$Cl$_2$ (1 mL). After 10 min, TLC analysis of the reaction mixture using a mixture of CH$_2$Cl$_2$ and MeOH (20/1, v/v) as eluant indicated consumption of the starting material. The reaction mixture was quenched with MeOH (5 mL), and evaporated to dryness. The residual oil was taken up in ethyl acetate (30 mL), and the organic layer was washed with brine (2×10 mL), dried over sodium sulfate. The mixture was filtered, and the filtrate was concentrated in vacuo to give a solid. The solid was triturated with ether, and was then collected by suction filtration. The title compound was obtained as an off-white solid (80 mg, 50% yield). The purity (peak area percent is 97.3%) of this material was analysed by HPLC Method 1 as described above.

$^1$H NMR (400 MHz, DMSO-D$_6$) δ (ppm): 9.59 (s, 1H), 8.22 (s, 1H), 6.93 (t, J=52.8 Hz, 1H, CF$_2$H), 6.76 (s, 1H).

On a 2.6 g scale, the product was isolated in 90% yield (1.5 g).

EXAMPLE 5

Preparation of 5-benzyloxy-2-difluoromethyl-1-methyl-1H-pyridin-4-one

A 2.0M methylamine solution in methanol (19.0 mL, 38.0 mmol) was added to a suspension of 5-benzyloxy-2-difluoromethyl-pyran-4-one (3.15 g, 12.5 mmol) in methanol (18 mL). The reaction mixture slowly turned into a clear yellow solution. The progress of the reaction was monitored by TLC using a mixture of methanol and dichloromethane (1/20, v/v) as eluant, and HPLC method 1 as described above. After 70 minutes, the reaction mixture was concentrated in vacuo to obtain an oil. The oil was diluted with ether and allowed to stir overnight at room temperature. A precipitate had formed and it was collected by filtration. The solid was washed with ether, and the title compound was obtained as an off white solid (2.50 g, 75% yield). The purity of this material was analysed by HPLC Method 1 (peak area percent is 98.8% at λ=288 nm) as described above. $^1$H NMR (400 MHz, DMSO-D$_6$) δ (ppm): 7.75 (s, 1H), 7.44-7.34 (m, 5H, ArH), 7.12 (t, J=53.0 Hz, 1H, CF$_2$H), 6.48 (s, 1H), 5.02 (s, 2H, OCH$_2$), 3.71 (s, 3H, N—CH$_3$).

The following compounds were prepared in a similar fashion:

5-Benzyloxy-2-difluoromethyl-1-ethyl-1H-pyridin-4-one

5-Benzyloxy-2-difluoromethyl-pyran-4-one (2.0 g, 7.93 mmol) was suspended in 15 mL of methanol. A 2.0M solution of ethylamine in methanol (8.0 mL) was added at room temperature, and the reaction slowly turned into a clear yellow/green solution over 10 min. After 4 h, the reaction mixture was concentrated in vacuo to an oil. The oil was diluted with 10 mL of ethyl acetate and stirred until a solid precipitated out. The solid was collected by suction filtration, thoroughly washed with ether, and dried to afford the title product (1.14 g, 52% yield). HPLC purity (peak area percent) is 97.5% at λ=280 nm using HPLC Method 1 as described above.

1-Allyl-5-benzyloxy-2-difluoromethyl-1H-pyridin-4-one

A mixture of 5-benzyloxy-2-difluoromethyl-pyran-4-one (4.00 g, 15.8 mmol), allylamine (3.60 mL, 47.5 mmol) in methanol (40 mL) was stirred at room temperature for 1 hour. The reaction mixture was evaporated to dryness, and the residual solid was dissolved in 10 mL of ethyl acetate, and again concentrated in vacuo. The solid was suspended in a mixture of ethyl acetate and ether, then collected by suction filtration and thoroughly washed with ether. The off-white solid was dried to constant weight in a vacuum oven at 40° C. to afford the title product (3.38 g, 73% yield). HPLC purity (peak area percent) is 98.9% at λ=278 nm using HPLC Method 1 as described above. $^1$H NMR (400 MHz, CDCl$_3$) δ (ppm): 7.35-7.43 (m, 5H, ArH), 7.16 (s, 1H), 6.79 (s, 1H), 6.48 (t, J=53.1 Hz, 1H, CF$_2$H), 5.80-5.86 (m, 1H), 5.29 (d, J=10.4 Hz, 1H), 5.22 (s, 2H, OCH$_2$), 5.10 (d, J=17.1 Hz, 1H), 4.58 (d, J=5.2 Hz, 2H); MS-ESI (m/z): 291.9 [M+1]$^+$, 91.0.

5-Benzyloxy-1-cyclopropyl-2-difluoromethyl-1H-pyridin-4-one

A mixture of 5-benzyloxy-2-difluoromethyl-pyran-4-one (4.0 g, 15.8 mmol) and cyclopropylamine (3.6 mL, 47.5 mmol) in methanol (40 mL) was stirred at room temperature for 7.5 hrs. The reaction mixture was concentrated in vacuo to obtain an oil. The oil was diluted with dichloromethane and ether, and a solid precipitated out. The solid was collected by suction filtration to afford 1.64 g of the title compound as the first crop. The filtrate was concentrated and then purified by column chromatography using a mixture of methanol and dichloromethane (1:20, v/v) as eluant. Fractions rich in the product were pooled together and evaporated to dryness, thereby affording a second crop (2.4 g). Crops 1 and 2 were combined to give 4.0 g (87%) of the title product. HPLC purity (peak area percent) is 98.8% at λ=280 nm using HPLC Method 1 as described above. $^1$H NMR (400 MHz, DMSO-D$_6$) δ (ppm): 7.57 (s, 1H), 7.21-7.48 (m, 6H, 5ArH+CF$_2$H), 6.44 (s, 1H), 5.05 (s, 2H, OCH$_2$), 3.50-3.56 (m, 1H), 1.10-1.16 (m, 2H, CH$_2$), 1.05-1.09 (m, 2H, CH$_2$).

5-Benzyloxy-1-cyclopropylmethyl-2-difluoromethyl-1H-pyridin-4-one

A mixture of 5-benzyloxy-2-difluoromethyl-pyran-4-one (4.03 g, 16.0 mmol) and cyclopropyl-methylamine (3.50 g, 47.9 mmol) in methanol (40 mL) was stirred at room temperature for 3 hrs. The reaction was concentrated in vacuo to obtain an oil. The oil was diluted with ethyl acetate and ether and allowed to stir overnight at room temperature. A precipitate had formed and was collected by suction filtration. The solid was thoroughly washed with ether and dried. The title product was thus obtained as an off white solid (3.98 g, 82% yield). HPLC purity (peak area percent) is 99.5% at λ=280 nm using HPLC Method 1 as described above. $^1$H NMR (400 MHz, CDCl$_3$) δ (ppm): 7.29-7.44 (m, 6H, 5ArH+CH), 6.78 (s, 1H), 6.51 (t, J=53.2 Hz, 1H, CF$_2$H), 5.26 (s, 2H, OCH$_2$), 3.86 (d, J=7.0 Hz, 2H), 1.06-1.09 (m, 1H), 0.58-0.63 (m, 2H, CH$_2$), 0.25-0.30 (m, 2H, CH$_2$); MS-ESI (m/z): 306.3 [M+1]$^+$, 252.0, 91.4.

EXAMPLE 6

Preparation of 2-difluoromethyl-5-hydroxy-1-methyl-1H-pyridin-4-one

A mixture of 5-benzyloxy-2-difluoromethyl-1-methyl-1H-pyridin-4-one (1.90 g, 7.16 mmol) and 10% Pd/C (190 mg) in methanol (60 mL) was hydrogenated under a hydrogen atmosphere at 15 psi of pressure in a Parr apparatus for 25 min. The mixture was diluted with methanol (180 mL), sonicated for 15 min, and then filtered through a pad of CELITE™ (pre-treated with dilute HCl and washed to neutral with deionized water). The volume of the filtrate was reduced using a rotary evaporator until a solid precipitated out. The mixture was diluted with 2 mL of methanol and the solid was collected by suction filtration. The solid was thoroughly washed with ether, and then dried in a vacuum oven to afford the title product (1.00 g, 79% yield). HPLC purity (peak area percent) of the product is 99.2% at λ=288 nm using HPLC Method 1 as described above. $^1$H NMR (400 MHz, DMSO-D$_6$) δ (ppm): 7.56 (s, 1H), 7.12 (t, J=52.7 Hz, 1H, CF$_2$H), 6.47 (s, 1H), 3.70 (s, 3H, N—CH$_3$); MS-ESI (m/z): 176.5 [M+1]$^+$, 126.2; Anal. Calcd. for C$_7$H$_7$F$_2$NO$_2$: C, 48.01; H, 4.03; N, 8.00%. Found: C, 48.15; H, 4.14; N, 7.88%.

The following compounds were prepared similarly:

2-Difluoromethyl-1-ethyl-5-hydroxy-1H-pyridin-4-one

A mixture of 5-benzyloxy-2-difluoromethyl-1-ethyl-1H-pyridin-4-one (2.00 g, 7.16 mmol) and 10% Pd/C (200 mg) in methanol (75 mL) was hydrogenated under 15.0 psi pressure in a hydrogen atmosphere in a Parr apparatus for 23 min. The reaction mixture was worked up as described above. The title compound (0.87 g, 64%) was obtained as an off-white solid. HPLC purity (peak area percent) of the compound is 97.7% at λ=280 nm using HPLC Method 1 as described above. $^1$H NMR (400 MHz, DMSO-D$_6$) δ (ppm): 7.61 (s, 1H), 7.15 (t, J=52.7 Hz, 1H, CF$_2$H), 6.46 (s, 1H), 4.03 (q, J=7.0 Hz, 2H, N—CH$_2$), 1.31 (t, J=7.1 Hz, 3H, CH$_3$); MS-ESI (m/z): 190.2 [M+1]$^+$, 142.2 (100%); Anal. Calcd. for C$_8$H$_9$F$_2$NO$_2$: C, 50.80; H, 4.80; N, 7.40%. Found: C, 50.64; H, 4.85; N, 7.38%.

1-Cyclopropyl-2-difluoromethyl-5-hydroxy-1H-pyridin-4-one

A mixture of 5-benzyloxy-1-cyclopropyl-2-difluoromethyl-1H-pyridin-4-one (3.0 g, 10.3 mmol) and 10% Pd/C (340 mg) in methanol (60 mL) was subjected to hydrogenation in a Parr apparatus under a 15 psi hydrogen pressure for 22 min. The mixture was diluted with 300 mL of methanol, sonicated for 20 min, and then filtered through a pad of CELITE™ (pre-treated with HCl and washed to neutral with deionized water). The volume of the filtrate was reduced in vacuo until a solid precipitated out. The solid was collected by suction filtration. The recrystallization was repeated on the filtrate to obtain a second crop of solid. The combined solids were dried to constant weight in a vacuum oven thereby affording the title product (1.61 g) in 77% yield. HPLC purity (peak area percent) of product is 99.5% at λ=280 nm using HPLC Method 1 as described above. $^1$H NMR (400 MHz, DMSO-D$_6$+D$_2$O) δ (ppm): 7.54 (s, 1H), 7.33 (t, J=53.0 Hz, 1H, CF$_2$H), 6.51 (s, 1H), 3.53-3.57 (m, 1H, N—CH), 1.07-1.10 (m, 4H, 2CH$_2$); MS-ESI (m/z): 202.5 [M+1]$^+$, 142.3

(100%); Anal. Calcd. for $C_9H_9F_2NO_2$: C, 53.73; H, 4.51; N, 6.96%. Found: C, 53.75; H, 4.80; N, 6.89%.

1-Cyclopropylmethyl-2-difluoromethyl-5-hydroxyl-1H-pyridin-4-one

A mixture of 5-benzyloxy-1-cyclopropylmethyl-2-difluoromethyl-1H-pyridin-4-one (3.0 g, 9.82 mmol) and 10% Pd/C (300 mg) in methanol (90 mL) was subjected to hydrogenation in a Parr apparatus under a 15 psi hydrogen pressure for 27 min. Work-up as described above for the cyclopropyl derivative, afforded the title product (1.76 g, 83% yield) after vacuum oven drying. HPLC purity (peak area percent) of the title compound is 99.5% at λ=288 nm using HPLC Method 1 as described above.

$^1$H NMR (400 MHz, DMSO-$D_6$) δ (ppm): 7.65 (s, 1H), 7.19 (t, J=52.6 Hz, 1H, $CF_2H$), 6.48 (s, 1H), 3.88 (d, J=7.1 Hz, 2H, N—$CH_2$), 1.19 (m, 1H), 0.45-0.57 (m, 4H); MS-ESI (m/z): 216.1 $[M+1]^+$, 55.2 (100%); Anal. Calcd. for $C_{10}H_{11}F_2NO_2$: C, 55.81; H, 5.15; N, 6.51%. Found: C, 56.20; H, 5.44; N, 6.40%.

EXAMPLE 7

1-Allyl-2-difluoromethyl-5-hydroxy-1-H-pyridin-4-one

An alternative debenzylation procedure was used for the allyl derivative in order to avoid reduction of the allyl double bond. Thus, a clear yellow/brown solution of 1-allyl-5-benzyloxy-2-difluoromethyl-1H-pyridin-4-one (2.91 g, 10 mmol) in dichloromethane (30 mL) was cooled in an ice-salt bath under a positive nitrogen atmosphere. Then, a pre-mixed 1.0 M boron tribromide solution (10 mL) and dichloromethane (10 mL) was added dropwise. After 20 min, the reaction mixture was quenched with 25 mL of methanol. The solution was concentrated to dryness. The obtained solid was suspended in ether. The solid was collected by filtration to afford the title product (2.65 g, 94% yield) as the hydrobromide salt. HPLC purity (peak area percent) is 99.4% at λ=267 nm using HPLC Method 1 as described above. $^1$H NMR (400 MHz, DMSO-$D_6$+$D_2O$) δ (ppm): 8.10 (s, 1H), 7.29 (t, J=53.0 Hz, 1H, $CF_2H$), 6.26 (s, 1H), 5.07-6.00 (m, 1H), 5.36 (d, J=10.3 Hz, 1H), 5.20 (d, J=17.1 Hz, 1H), 4.95 (d, J=5.1 Hz, 2H).

The hydrobromide salt (2.1 g, 7.44 mmol) was dissolved in ice cold deionized water to give a clear brown solution. The solution was filtered to remove solid particulates, and the filtrate was cooled in an ice bath. A 6N NaOH solution (1.24 mL) was added dropwise, the pH of the solution was adjusted to about 5.5, and a solid precipitated out. The solid was collected by suction filtration, washed twice with ice cold deionized water and twice with 5 mL of ether. The solid was dried in a vacuum oven at 40° C. to afford the title product (1.37 g, 91% yield). HPLC purity (peak area percent) of the title compound is 99.2% at λ=280 nm using HPLC Method 1 as described above.

$^1$H NMR (400 MHz, DMSO-$D_6$) δ (ppm): 7.50 (s, 1H), 7.10 (t, J=52.6 Hz, 1H, $CF_2H$), 6.51 (s, 1H), 5.92-6.00 (m, 1H), 5.27 (d, J=10.6 Hz, 1H), 5.13 (d, J=17.1 Hz, 1H), 4.65 (d, J=5.0 Hz, 2H); MS-ESI (m/z): 202.4 $[M+1]^+$, 142.1, 41.2 (100%); Anal. Calcd. for $C_9H_9F_2NO_2$: C, 53.73; H, 4.51; N, 6.96%. Found: C, 53.85; H, 4.69; N, 6.84%.

EXAMPLE 8

Preparation of 6-difluoromethyl-3-hydroxy-2-hydroxymethyl-1-methyl-1H-pyridin-4-one A clear slightly yellow solution of a mixture of 2-difluoromethyl-5-hydroxy-1-methyl-1H-pyridin-4-one (3.50 g, 20 mmol), prepared as described in Example 6 above, a 37-40% formaldehyde solution in water (60 mL, 0.80 mol) and a 6M NaOH solution (4 mL, 24 mmol) was heated at 42-44° C. for 24 hrs.

The reaction mixture was cooled to room temperature, then placed in an ice bath, and the pH of the mixture was adjusted to about 5 with a 6.0N solution of HCl (2.5 mL). The mixture was stirred at room temperature for 48 hrs. The bulk of the solvent was removed under reduced pressure using a rotary evaporator and a solid precipitated out. Deionized water (5 mL) and a small amount of methanol were added. The first solid crop was isolated by suction filtration. The filtrate was concentrated and recrystallization as described above afforded 1.18 g of a second crop. Thus, a combined yield of 73% was obtained for the title product. HPLC purity (peak area percent) of the title product is 97.5% at λ=280 nm using HPLC Method 1 as described above. $^1$H NMR (400 MHz, DMSO-$D_6$) δ (ppm): 7.21 (t, J=52.7 Hz, 1H, $CF_2H$), 6.48 (s, 1H), 4.68 (s, 2H, $CH_2$), 3.77 (s, 3H, $NCH_3$); MS-ESI (m/z): 206.0 $[M+1]^+$, 188.3, 160.3 (100%); Anal. Calcd. for $C_8H_9F_2NO_3$: C, 46.83; H, 4.42; N, 6.83%. Found: C, 47.01; H, 4.43; N, 6.78%.

EXAMPLE 9

Preparation of 6-difluoromethyl-3-hydroxy-1,2-dimethyl-1H-pyridin-4-one

Step 1: A mixture of 6-difluoromethyl-3-hydroxy-2-hydroxymethyl-1-methyl-1H-pyridin-4-one (2.47 g, 12.0 mmol), obtained as described in Example 8, benzyl bromide (1.72 mL, 14.4 mmol) and a 6.0 M NaOH solution (2.20 mL, 13.2 mmol) in MeOH (15 mL) was refluxed for 3.5 hrs. The progress of the reaction was monitored by TLC using a mixture of $CH_2Cl_2$ and MeOH (10/1, v/v) as eluant. The reaction mixture was concentrated in vacuo. The residual oil was taken up in $CH_2Cl_2$ and then washed with brine. The organic fraction was collected, dried over sodium sulfate, filtered, and evaporated to dryness. The residue was triturated with i-PrOH, and on stirring a solid precipitated out. The solid was collected and dried under vacuum to afford 2.55 g of crop 1.

The filtrate was evaporated to dryness, and the residue was purified by column chromatography on silica gel using a solvent gradient of a mixture of $CH_2Cl_2$ and MeOH (20/1 to 10/1, v/v) as eluant to afford another 350 mg of the benzylated product as a second crop. The 2 crops were combined to give 2.9 g (80% yield) of 3-benzyloxy-6-difluoromethyl-2-hydroxymethyl-1-methyl-1H-pyridin-4-one. HPLC purity (peak area percent) of the title product is 99.6% at λ=280 nm using HPLC Method 1 as described above. $^1$H NMR (400 MHz, DMSO-$D_6$) δ (ppm): 7.33-7.50 (m, 5H), 7.22 (t, J=52.7 Hz, 1H, $CF_2H$), 6.56 (s, 1H), 5.57 (t, J=5.1 Hz, 1H, OH), 5.07 (s, 2H, $CH_2Ar$), 4.61 (d, J=5.1 Hz, 2H, $CH_2OH$), 3.74 (s, 3H, $NCH_3$).

Step 2: To an ice-cooled suspension of the benzylated derivative, (1.51 g, 5.10 mmol) obtained in step 1 above, in $CH_2Cl_2$ (50 mL) was added a solution of $Et_3N$ (1.20 mL, 8.63 mmol) in 2 mL CH$_2$Cl$_2$, followed by methanesulfonyl chloride (0.65 mL, 8.40 mmol). After 5 min, TLC analysis indicated consumption of starting material. The reaction mixture was diluted with CH$_2$Cl$_2$ (50 mL). The organic layer was washed with brine (2×30 mL), dried over Na$_2$SO$_4$, filtered and concentrated to an oil.

The oil was taken up in i-PrOH (120 mL), AcOH (1.2 mL) and a 10% wet Pd—C solid (750 mg) were added. The mixture was subjected to hydrogenation in a Parr apparatus under a 16 psi hydrogen pressure. The progress of the reaction was monitored by HPLC Method 1 as described above. The reaction had stopped after 1 hr. The mixture was filtered over an acid pre-treated CELITE™ bed. The filtrate was collected; fresh Pd—C (300 mg) and AcOH (0.6 mL) were added. The mixture was again hydrogenated at 16 psi pressure of hydrogen for another 10 min, at which time all the sulfonylated material had been consumed. The mixture was filtered over pre-treated CELITE™. The filtrate was collected and evaporated to dryness to give an oil. The oily residue was dissolved in de-ionized water, and the pH of the solution was adjusted to 6 with a 6.0N NaOH solution. A solid which separated, was collected by suction filtration. The solid was thoroughly washed with ether and then dried overnight under vacuum in an oven at 40° C. The title compound was obtained as an off-white solid. HPLC purity (peak area percent) of title compound is 96.5% at λ=280 nm using HPLC Method 1 as described above. $^1$H NMR (400 MHz, DMSO-D$_6$+D$_2$O) δ (ppm): 7.17 (t, J=52.7 Hz, 1H, CF$_2$H), 6.46 (s, 1H), 3.45 (s, 3H, NCH$_3$), 2.35 (s, 3H, CH$_3$); Anal. Calcd. for C$_8$H$_9$F$_2$NO$_2$: C, 50.80; H, 4.80; N, 7.40%. Found: C, 50.69; H, 4.99; N, 7.22%.

EXAMPLE 10

Preparation of 6-difluoromethyl-3-hydroxy-2-(1-hydroxy-ethyl)-1-methyl-1H-pyridin-4-one Step 1: To an ice bath cooled suspension of 2-difluoromethyl-5-hydroxy-pyran-4-one (1.00 g, 6.17 mmol), obtained as described in Example 4, in deionized water was added a 6.0M NaOH solution (1.23 mL, 7.40 mmol). A clear dark brown red solution was obtained, and CH$_3$CHO (6.0 mL, 107 mmol) was added dropwise. After 2 hrs, the reaction mixture was cooled in ice and another 3 mL of CH$_3$CHO (54 mmol) was added. The cooling bath was removed and the reaction mixture was allowed to warm to room temperature overnight. The progress of the reaction was monitored by HPLC Method 1 as described above. Thus, after 24 hrs, the composition (% as peak percent area) of the reaction mixture was as follows: desired product (72%), starting material (7%), side products (15%, 2 major less polar components). The reaction mixture was cooled in ice and the pH was adjusted to 6 with the addition of a 6.0M HCl solution (1 mL). The mixture was concentrated in vacuo, and the residue was taken up in EtOAc. The organic layer was washed with brine (2×15 mL). The combined brine layers were back-extracted with EtOAc (2×). The organic fractions were combined, dried over Na$_2$SO$_4$, filtered, and evaporated to dryness. The residue was purified by column chromatography on silica gel using a mixture of CH$_2$Cl$_2$ and MeOH (25/1, v/v) as eluant. Fractions rich in product were combined together, and concentrated to give 6-difluoromethyl-3-hydroxy-2-(1-hydroxy-ethyl)-pyran-4-one as an oil. HPLC purity (peak area percent) of this material is 88.0% at λ=280 nm using HPLC Method 1 as described above.

This reaction was scaled up, and 3.0 g (18.5 mmol) of 2-difluoromethyl-5-hydroxy-pyran-4-one was used. The reaction mixture was stirred at ice-cold temperature for 6 h. The progress of the reaction every hr was monitored by HPLC Method 1 as described above. Thus, after 6 hrs, the composition (% as peak percent area) of the reaction mixture was as follows: desired product (67%), starting material (9%), side products (24%, 2 major less polar components). The work-up and column purification were as described above. HPLC purity (peak area percent) of this material is 91.0% at λ=280 nm using HPLC Method 1 as described above.

Step 2: The 6-difluoromethyl-3-hydroxy-2-(1-hydroxy-ethyl)-1-methyl-1H-pyridin-4-one product obtained in the 2 experiments in step 1 above were combined together and dissolved in MeOH (50 mL). A 6.0 M NaOH solution (4 mL, 24 mmol) and BnBr (2.85 mL, 24 mL) were successively added at room temperature. The progress of the reaction was monitored by HPLC Method 1 as described above. After 1.5 hrs, HPLC analysis of the reaction mixture indicated presence of about 15% of unreacted starting material. Thus, another 1 mL of a 6.0 M NaOH solution and 1 mL of BnBr were added, and the mixture was refluxed for 1 hr. The mixture was cooled to room temperature, and evaporated to dryness. The residue was taken up in CH$_2$Cl$_2$, and the organic layer was washed with brine (40 mL). The aqueous brine layer was back washed with CH$_2$Cl$_2$ (40 mL). The organic fractions were combined, dried over Na$_2$SO$_4$, filtered, and evaporated to dryness. The residue was purified by column chromatography on silica gel using a mixture of CH$_2$Cl$_2$ and MeOH (100/3, v/v) as eluant. Fractions rich in product were combined together, and concentrated to give 3-benzyloxy-6-difluoromethyl-2-(1-hydroxy-ethyl)-pyran-4-one (4.00 g) as a bright yellow oil. HPLC purity (peak area percent) of this material is 88.8% at λ=280 nm using HPLC Method 1 as described above.

Step 3: A mixture of the benzylated pyran-4-one derivative (4.00 g, 13.5 mmol), obtained in the step 2 above, and a 2M methanolic MeNH$_2$ solution (20 mL, 40.0 mmol) in MeOH (50 mL) was stirred at room temperature for overnight. The mixture was evaporated in vacuo to dryness, and the dark red oily residue was dissolved in CH$_2$Cl$_2$ (30 mL). The mixture was purified by column chromatography on silica gel using a mixture of CH$_2$Cl$_2$ and MeOH (25/1, v/v) as eluant. Fractions rich in product were pooled together, and concentrated to give 3-benzyloxy-6-difluoromethyl-2-(1-hydroxy-ethyl)-1-methyl-1H-pyridin-4-one as an oil (0.75 g). HPLC purity (peak area percent) of this material is 96.5% at λ=280 nm using HPLC Method 1 as described above.

Step 4: A mixture of the benzylated pyridin-4-one derivative (0.75 g) obtained as described in step 3 above and 97 mg of a wet 10% Pd—C in methanol (25 mL) was hydrogenated under a 15 psi hydrogen pressure in a Parr apparatus for 25 min. The mixture was diluted with MeOH (40 mL), sonicated, and filtered over a bed of acid pre-treated CELITE™. The volume of the filtrate was reduced by rotary evaporation under reduced pressure, as a solid precipitated out. The solid was collected by suction filtration, dried overnight in a vacuum oven. Thus, this first crop provided 260 mg of the compound as a white solid.

The filtrate was collected and the volume of solution was reduced. The flask was then cooled in ice. The precipitated solid was collected and vacuum-dried. This second crop afforded another 100 mg of the product.

The combined crops afforded 360 mg of 6-difluoromethyl-3-hydroxy-2-(1-hydroxy-ethyl)-1-methyl-1H-pyridin-4-one. HPLC purity (peak area percent) of the title compound is 99.5% at λ=280 nm using HPLC Method 1 as described above. $^1$H NMR (400 MHz, DMSO-D$_6$) δ (ppm): 7.20 (t, J=52.9 Hz, 1H, CF$_2$H), 6.48 (s, 1H), 5.53 (q, J=6.9 Hz, 1H, CH$_3$CH), 3.92 (s, 3H, NCH$_3$), 1.45 (d, J=6.9 Hz, 3H, CH$_3$);

MS-ESI (m/z): 220.0 [M+1]$^+$, 202.4 (100%); Anal. Calcd. for $C_9H_{11}F_2NO_3$: C, 49.32; H, 5.06; N, 6.39%. Found: C, 49.67; H, 5.42; N, 6.29%.

EXAMPLE 11

Preparation of 6-difluoromethyl-2-ethyl-3-hydroxy-1-methyl-1H-pyridin-4-one

Step 1: To a solution of 3-benzyloxy-6-difluoromethyl-2-(1-hydroxy-ethyl)-pyran-4-one (1.30 g, 4.38 mmol), described in step 2 of Example 10, in $CH_3CN$ (14 mL) cooled in an ice-salt bath was added a solution of $SOCl_2$ (0.45 mL, 5.44 mmol) in $CH_3CN$ (0.5 mL). The reaction mixture was stirred at ice-cold temperature for 9 hrs. The progress of the reaction was monitored by TLC using a mixture of hexanes and EtOAc (1/1, v/v) as eluant. Volatile materials were removed in vacuo, and ice-cold i-PrOH (15 mL) was added, and the mixture was cooled in an ice-salt bath. Then Zn dust (600 mg, 9 mmol) was added followed by concentrated HCl (1.1 mL). After 20 min, the reaction mixture was filtered through a CELITE™ bed, and the filtrate was evaporated to dryness. The residue was taken up in $CH_2Cl_2$ (100 mL), and the organic layer was washed with brine (2×30 mL), dried over $Na_2SO_4$, filtered and concentrated in vacuo. The residual oil was purified by column chromatography on silica gel using a mixture of hexanes and EtOAc (10/3, v/v) as eluant. Fractions rich in product were combined together, and concentrated to give 3-benzyloxy-6-difluoromethyl-2-ethyl-pyran-4-one (0.62 g) as a yellow oil. HPLC purity (peak area percent) of this material is 99.0% at λ=280 nm using HPLC Method 1 as described above. $^1$H NMR (400 MHz, DMSO-$D_6$) δ (ppm): 7.30-7.40 (m, 5H), 7.06 (t, J=52.7 Hz, 1H, $CF_2H$), 6.76 (s, 1H), 5.07 (s, 2H), 2.56 (q, J=7.4 Hz, 1H, $CH_2CH_3$), 0.97 (t, J=7.5 Hz, 3H, $CH_2CH_3$).

Step 2: A mixture of the 2-ethyl-pyran-4-one derivative (0.62 g, 2.21 mmol) obtained in step 1 above, and 8 mL of a 2.0M methanolic $MeNH_2$ solution in MeOH (6 mL) was stirred at room temperature for 2 hrs. Volatiles were removed in vacuo, and the residue was subjected to purification by column chromatography on silica gel using a mixture of $CH_2Cl_2$ and MeOH (20/1, v/v) as eluant, thereby affording 3-benzyloxy-6-difluoromethyl-2-ethyl-1-methyl-1H-pyridin-4-one (400 mg). HPLC purity (peak area percent) of this compound is 98.6% at λ=280 nm using HPLC Method 1 as described above.

Step 3: A mixture of the benzylated pyridin-4-one (400 mg, 1.36 mmol) obtained in step 2 above, and 63 mg of a wet 10% Pd—C in MeOH (25 mL) was hydrogenated under a 15 psi hydrogen atmosphere in a Parr apparatus for 25 min. The mixture was diluted with MeOH (40 mL), sonicated, and filtered over a bed of acid pre-treated CELITE™. The volume of the filtrate was reduced by rotary evaporation under reduced pressure, as a solid precipitated out. The solid was collected by suction filtration, dried overnight in a vacuum oven. Thus, this first crop provided 76 mg of the compound as a white solid after vacuum drying.

The filtrate was collected, and the volume reduced to obtain a precipitate. In this manner, a second crop (71 mg) and a third crop (30 mg) were obtained. The combined 3 crops thus afforded the title compound, 6-difluoromethyl-2-ethyl-3-hydroxy-1-methyl-1H-pyridin-4-one, (177 mg). HPLC purity (peak area percent) of this compound is 99.4% at λ=280 nm using HPLC Method 1 as described above. $^1$H NMR (400 MHz, DMSO-$D_6$) δ (ppm): 7.17 (t, J=52.8 Hz, 1H, $CF_2H$), 6.47 (s, 1H), 3.67 (s, 3H, $NCH_3$), 2.80 (q, J=7.4 Hz, 1H, $CH_2CH_3$), 1.13 (t, J=7.4 Hz, 3H, $CH_2CH_3$); MS-ESI (m/z): 204.3 [M+1]$^+$, 100%), 189.4; Anal. Calcd. for $C_9H_{11}F_2NO_2$: C, 53.20; H, 5.46; N, 6.89%. Found: C, 52.94; H, 5.48; N, 6.85%.

EXAMPLE 12

Preparation of 3-hydroxy-6-methyl-2-(2,2,2-trifluoro-1-hydroxy-ethyl)-pyran-4-one Step 1: A mixture of allomaltol (5.00 g, 39.6 mmol), trifluoroacetaldehyde methyl hemiacetal (4.67 mL, 54.2 mmol, 90% technical grade) and zinc iodide (632 mg, 2.00 mmol) was refluxed for 7 hrs, then allowed to cool to room temperature and stirred overnight. Analysis of the reaction mixture by using HPLC Method 2 indicated the presence of about 53% (peak area percent) of the starting allomaltol. HPLC Method 2: Column: Waters symmetry C18; 5 µm, 3.9×150 mm; Mobile phase: A=the aqueous phase: 0.035% $HClO_4$, pH 2; B=the organic phase: $CH_3CN$; gradient: B %: 0 min—10%, 10 min—90%, 12 min—90%; Flow rate: 1 ml/min; λ: 220, 254, 280 nm. Thus, another 200 mg of zinc iodide (0.63 mmol) and 2 mL of trifluoroacetaldehyde methyl hemiacetal (20.0 mmol) were added. The mixture was refluxed for another 8 hrs, then allowed to cool to room temperature and stirred for overnight.

The reaction mixture was quenched with water and extracted with EtOAc (2×). The combined EtOAc layers was washed with brine, dried over anhydrous sodium sulphate, filtered, concentrated to dryness. The solid residue was suspended in EtOAc and hexanes and stirred. The solid was collected by suction filtration, and dried to afford 5.47 g of a light yellow solid. Analysis of the reaction mixture using HPLC Method 2, as described above, indicated the presence of 3-hydroxy-6-methyl-2-(2,2,2-trifluoro-1-hydroxy-ethyl)-pyran-4-one (peak area is 82%) and allomaltol (16%). $^1$H NMR of mixture (400 MHz, DMSO-$D_6$) δ(ppm): 7.98 (s, 0.3H, allomaltol), 6.30 (s, 1H), 6.25 (s, 0.3H, allomaltol), 5.32 (q, J=7.0 Hz, 1H, $CHCF_3$), 2.28 (s, 3H, $CH_3$), 2.24 (s, 0.78H, $CH_3$, allomaltol).

Step 2: To obtain a pure sample of 3-hydroxy-6-methyl-2-(2,2,2-trifluoro-1-hydroxy-ethyl)-pyran-4-one, the mixture above was reacted with benzyl bromide as described in Example 1 above. Purification by flash column chromatography afforded a pure sample of 3-benzyloxy-6-methyl-2-(2,2,2-trifluoro-1-hydroxy-ethyl)-pyran-4-one (3.08 g). HPLC purity (peak area percent) of this compound is 98.4% at λ=254 nm using HPLC Method 2 as described above. $^1$H NMR (400 MHz, $CDCl_3$) δ(ppm): 7.38-7.45 (m, 5H), 6.25 (s, 1H), 5.18-5.29 (2d, J=10.6 Hz, 2H, $CH_2Ar$), 5.10 (q, J=7, 0 Hz, 1H, $CHCF_3$), 2.29 (s, 3H, $CH_3$); MS-ESI (m/z): 315.0 [M+1]$^+$, 91.4 (100%).

Debenzylation of this material was carried out as described in step 3 of Example 11 above, to afford a pure sample of 3-hydroxy-6-methyl-2-(2,2,2-trifluoro-1-hydroxy-ethyl)-pyran-4-one. The reaction time was 1.5 hrs. HPLC purity (peak area percent) of this compound is 99.7% at λ=254 nm using HPLC Method 2 as described above. $^1$H NMR (400 MHz, DMSO-$D_6$) δ: 9.66 (br s, 1H, OH), 7.14 (br s, 1H, OH), 6.31 (s, 1H), 5.34 (q, 1H, J=7.2 Hz, $CHCF_3$), 2.28 (s, 3H); MS m/z 225.2 [M+1]$^+$, 207.1, 179.4 (100%), 159.3, 91.1; Anal. Calcd. for $C_8H_7F_3O_4$: C, 42.87; H, 3.15%. Found: C, 42.55; H, 3.20%.

EXAMPLE 13

Preparation of 3-hydroxy-1,6-dimethyl-2-(2,2,2-trifluoro-1-hydroxy-ethyl)-1H-pyridin-4-one A mixture of 5-hydroxy-1,2-dimethyl-1H-pyridin-4-one (9.40 g, 67.6 mmol), trifluoroacetaldehyde methyl hemiacetal (28 mL) and $K_2CO_3$ (1.40 g, 10.0 mmol) was sealed in a parallel reactor and stirred overnight at 130° C. The reaction mixture was evaporated to dryness, and the residue was purified by flash column chromatography using a mixture of i-PrOH and a 28-30% conc. $NH_4OH$ solution (70/30, v/v) as eluent. Fractions containing pure product were pooled together, and evaporated to give the title compound as a light orange powder (6.3 g, 39% yield). HPLC purity (peak area percent) of this compound is 99.8% at λ=254 nm using HPLC Method 2 as described above. $^1H$ NMR (400 MHz, DMSO-$D_6$) δ: 6.83 (br s, 2H, 2OH), 6.21 (s, 1H), 5.88 (q, J=8.7 Hz, 1H), 3.73 (s, 3H, $NCH_3$), 2.31 (s, 3H, $CH_3$); MS m/z 238.1 $[M+1]^+$, 220.2, 192.3, 172.3 (100%). A second less pure fraction of the title compound (7.0 g) was also obtained, and was used without further purification in step 1 of Example 14 below.

EXAMPLE 14

Preparation of 3-hydroxy-1,6-dimethyl-2-(2,2,2-trifluoro-ethyl)-1H-pyridin-4-one Step 1: The benzylation reaction was carried out as described in Example 1 above, using 7 g of 3-hydroxy-1,6-dimethyl-2-(2,2,2-trifluoro-1-hydroxy-ethyl)-1H-pyridin-4-one as starting material. After usual work-up, purification of the crude by flash column chromatography on silica gel (5% MeOH in $CH_2Cl_2$ as eluant) afforded 3.49 g of 3-benzyloxy-1,6-dimethyl-2-(2,2,2-trifluoro-1-hydroxy-ethyl)-1H-pyridin-4-one as a orange solid. $^1H$ NMR (400 MHz, DMSO-$D_6$) δ: 7.32-7.46 (m, 5H), 6.29 (s, 1H), 5.99 (q, J=9.0 Hz, 1H), 5.05-5.20 (two d, J=10.8 Hz, 2H, $CH_2Ar$), 3.72 (s, 3H, $NCH_3$), 2.32 (s, 3H, $CH_3$); MS m/z 328.3 $[M+1]^+$, 91.1 (100%).

Step 2: To an ice-cooled solution of the product obtained in step 1 above (3.47 g, 10.6 mmol), and $Et_3N$ (1.92 mL, 13.8 mmol) in $CH_2Cl_2$ (60 mL) was added dropwise methanesulfonyl chloride (0.99 mL, 12.7 mmol). After stirring for 2 hrs, the reaction mixture was quenched with water and then extracted with $CH_2Cl_2$ (2×). The combined $CH_2Cl_2$ layer was washed with brine, dried over anhydrous sodium sulphate, filtered, and concentrated to dryness. The residue was purified by flash column chromatography on silica gel (5% MeOH in $CH_2Cl_2$ as eluant) to afford 2.3 g (53% yield) of methanesulfonic acid 1-(3-benzyloxy-1,6-dimethyl-4-oxo-1,4-dihydro-pyridin-2-yl)-2,2,2-trifluoro-ethyl ester. HPLC purity (peak area percent) of this compound is 91.1% at λ=254 nm using HPLC Method 2 as described above. $^1H$ NMR (400 MHz, $CDCl_3$) δ: 7.50-7.55 (m, 2H), 7.32-7.40 (m, 3H), 6.98 (q, J=7.5 Hz, 1H, $CHCF_3$), 6.60 (s, 1H), 5.28-5.50 (two d, J=10.7 Hz, 2H, $CH_2Ar$), 3.68 (s, 3H), 3.03 (s, 3H), 2.39 (s, 3H); MS m/z 406.0 $[M+1]^+$, 220.4, 192.2, 172.3, 91.0.

Step 3: To a solution of the product obtained in step 2 above (1.46 g, 3.60 mmol) in 100 mL of EtOH was added 10% wet Pd—C (330 mg), and the mixture was hydrogenated under a hydrogen atmosphere at 50 psi pressure for 2 hrs. The reaction mixture was filtered through CELITE™, and the filtrate was concentrated to dryness. The residue was purified by flash column chromatography on silica gel using a mixture of i-PrOH and a 28-30% conc. $NH_4OH$ solution (80/20, v/v) as eluent. The solid obtained was stirred in a mixture of i-PrOH (4 mL) and $H_2O$ (1 mL), then collected by suction filtration. Then, the solid was thoroughly washed with 4 mL of a mixture of i-PrOH and $H_2O$ (9/1, v/v). The solid was then dried overnight in a vacuum oven at 40° C. to afford the title product, 3-hydroxy-1,6-dimethyl-2-(2,2,2-trifluoro-ethyl)-1H-pyridin-4-one (420 mg, 53% yield) as light orange powder. HPLC purity (peak area percent) of this compound is 97.2% at λ=254 nm using HPLC Method 2 as described above. $^1H$ NMR (400 MHz, MeOD-$D_4$) δ: 6.39 (s, 1H), 3.96 (q, J=10.1 Hz, 2H), 3.69 (s, 3H, $NCH_3$), 2.42 (s, 3H); MS m/z 222.2 $[M+1]^+$, 202.4, 182.3, 153.3.

EXAMPLE 15

Preparation of 2-difluoromethyl-3-hydroxy-1,6-dimethyl-1H-pyridin-4-one

Step 1: The benzylation of 3-hydroxy-2-hydroxymethyl-6-methyl-pyran-4-one (25 g, 160.1 mmol) was carried out as described in Example 1 above. The benzylated product was slurried in a mixture of EtOAc and hexanes, filtered and dried to constant weight. Thus, 3-benzyloxy-2-hydroxymethyl-6-methyl-pyran-4-one was obtained as a light yellow solid (32.5 g, 82.4% yield). $^1H$ NMR (400 MHz, $CDCl_3$) δ: 7.39 (s, 5H), 6.29 (s, 1H), 5.23 (s, 2H), 4.30 (s, 2H), 2.30 (s, 3H).

Step 2: A solution of the product obtained in step 1 above (5.00 g, 20.3 mmol) in 20 mL of $CH_2Cl_2$ was cooled to 0° C., TEMPO (57.3 mg, 0.367 mmol) was added followed by a 2.75M aqueous solution of potassium bromide (5.2 g) and a saturated aqueous solution of sodium bicarbonate (22.4 g). To this resulting mixture was added 18 mL of bleach (10-14%) over period of 30 min. After stirring for 40 min at 0-5° C., a 1.0M aqueous solution of sodium thiosulphate (11.8 g) was added. The organic layer was collected, and the aqueous fraction was extracted with $CH_2Cl_2$, and the combined organic fractions were washed with brine, dried over anhydrous sodium sulphate, filtered and concentrated to give 3.6 g of crude 3-benzyloxy-6-methyl-4-oxo-4H-pyran-2-carbaldehyde. $^1H$ NMR (400 MHz, $CDCl_3$) δ: 9.86 (s, 1H), 7.37 (s, 5H), 6.32 (s, 1H), 5.51 (s, 2H), 2.34 (s, 3H); MS m/z 245.2 $[M+1]^+$, 91.2.

Step 3: To a solution of the crude aldehyde obtained above (3.2 g, 13.1 mmol) in 50 mL of $CH_2Cl_2$ was added diethylaminosulfur trifluoride (DAST, 2.2 mL, 17.06 mmol) at ice-salt bath temperature (−5° C. to 0° C.) under $N_2$ protection. The reaction was complete after 5 hrs based on HPLC analysis (HPLC Method 2 as described above). The reaction mixture was quenched with a 10% $NaHCO_3$ solution, then extracted with $CH_2Cl_2$, the combined organic layers was washed with brine, dried over anhydrous sodium sulphate, filtered and concentrated to dryness. The residue was purified by flash column chromatography on silica gel using a mixture of EtOAc and hexanes (1/1, v/v) as eluant. Thus, 3-benzyloxy-2-difluoromethyl-6-methyl-pyran-4-one was obtained as a light brown solid (2.01 g 57.6% yield). HPLC purity (peak area percent) is 95.7% using HPLC Method 2 as described above. $^1H$ NMR (400 MHz, $CDCl_3$) δ: 7.38-7.37 (m, 5H), 6.54 (t, J=52.3 Hz, 1H), 6.27 (s, 1H), 5.30 (s, 2H), 2.33 (s, 3H); MS m/z 267.0 $[M+1]^+$, 91.3 (100%).

Step 4: To a solution of difluoro compound obtained as described in step 3 above (1.94 g, 7.29 mmol) in 10 mL of MeOH was added $MeNH_2$ (2M in MeOH, 36.5 mL, 72.9 mmol) at RT and then stirred for 2.5 h. The reaction mixture was evaporated to dryness, and the residue was purified via flash column chromatography on silica gel using a mixture of $CH_2Cl_2$ and MeOH (19/1, v/v) to afford 1.3 g (63.9% yield) of 3-benzyloxy-2-difluoromethyl-1,6-dimethyl-1H-pyridin-4-one as a light brown solid. $^1H$ NMR (400 MHz, DMSO-$D_6$) δ: 7.41-7.36 (m, 5H), 7.18 (t, J=52.5 Hz, 1H), 6.31 (s, 1H), 5.23 (s, 2H), 3.55 (s, 3H, $NCH_3$), 2.31 (s, 3H); MS m/z 280.0 $[M+1]^+$, 91.2 (100%).

Step 5: To a solution of benzylated pyridin-4-one obtained in step 4 above (100 mg, 0.358 mmol) in 20 mL of MeOH was added 10% Pd—C (10 mg). The mixture was hydrogenated under 15 psi hydrogen pressure for 1 h. The reaction mixture was filtered through CELITE™, the filtrate was concentrated to dryness. The residue was suspended in EtOAc and then filtered to afford the title compound, 2-difluoromethyl-3-hydroxy-1,6-dimethyl-1H-pyridin-4-one, as a light brown powder (34 mg, 50.2% yield). HPLC purity (peak area percent) is >99% using HPLC Method 2 as described above. $^1$H NMR (400 MHz, DMSO-D$_6$) δ: 7.40 (t, J=52.0 Hz, 1H), 6.22 (s, 1H), 3.63 (s, 3H, NCH$_3$), 2.33 (s, 3H); MS m/z 190.1 [M+1]$^+$, 170.3, 142.2 (100%).

In a similar manner, 2-difluoromethyl-3-hydroxy-1-methyl-1H-pyridin-4-one (R═H) was prepared. $^1$H NMR (400 MHz, DMSO-D$_6$+a few drops of D$_2$O) δ: 7.99 (d, J=7.0 Hz, 1H), 7.46 (t, J=51.2 Hz, 1H, CHF$_2$), 6.79 (d, J=7.0 Hz, 1H), 3.95 (s, 3H, NCH$_3$); MS m/z 176.3 [M+1]$^+$, 156.1, 128.2 (100%).

EXAMPLE 16

Preparation of 2-fluoromethyl-5-hydroxy-1-methyl-1H-pyridin-4-one

Step 1: To an ice/salt cooled suspension of 5-benzyloxy-2-hydroxymethyl-pyran-4-one (30.0 g, 0.129 mol) in dichloromethane (500 mL) were added, successively, triethylamine (21.0 mL, 0.151 mol) and a solution of methanesulfonyl chloride (8.3 mL, 0.129 mol) in 10 mL of dichlroromethane. The progress of the reaction was monitored by TLC (CH$_2$Cl$_2$/MeOH, 10/1, v/v), and by HPLC Method 1 as described above. An additional methanesulfonyl chloride (0.5 mL, 7.70 mmol) and triethylamine (2.0 mL, 14.2 mmol) were added to the solution after 50 min. Again, an additional methanesulfonyl chloride (1.0 mL, 15.4 mmol) and triethylamine (2 mL, 14.2 mmol) were added an hour later. The reaction was quenched with 150 mL of brine. The organic phase was separated and collected, dried over sodium sulfate and concentrated in vacuo to give an oil. The oil was diluted with 200 mL of hexanes and a precipitate was formed. The solid was collected by suction filtration, and dried in a vacuum oven to give methanesulfonic acid 5-benzyloxy-4-oxo-4H-pyran-2-ylmethyl ester (39 g, 85% yield). HPLC purity (peak area percent) is 82.1% at λ=280 nm using HPLC Method 1 as described above. $^1$H NMR (400 MHz, DMSO-D$_6$) δ (ppm): 8.32 (m, 1H), 7.43-7.37 (m, 5H), 6.62 (m, 1H), 5.18 (m, 2H$_2$OCH$_2$), 4.98 (m, 2H, OCH$_2$), 3.36 (m, 3H, SCH$_3$).

Step 2: To an ice/salt cooled solution of the sulfonate ester obtained in step 1 above ester (20.0 g, 64.4 mmol) in acetonitrile (120 mL) was added a mixture of a 75 wt % solution of tetrabutylammonium fluoride (35 g, 96.6 mmol) and 40 mL of acetonitrile. Additional tetrabutylammonium fluoride solution (35 g, 96.6 mmol) was added after 2.5 hrs and the reaction mixture was allowed to stir at room temperature for overnight. The reaction was concentrated in vacuo to give a dark red oil. The residue was diluted with 700 mL of ethyl acetate and washed 5 times with 120 mL of a 10% sodium hydrogen carbonate solution and twice with 120 mL of brine. The organic layer was dried over sodium sulfate, and concentrated to give a dark red oil. The crude product was purified by column chromatography on silica gel using a mixture of ethyl acetate and hexanes (1/1, v/v) as the eluant to give 5-benzyloxy-2-fluoromethyl-pyran-4-one as a waxy-like solid (10.0 g, 66% yield). $^1$H NMR (400 MHz, DMSO-D$_6$) δ (ppm): 7.69 (s, 1H), 7.42-7.37 (m, 5H, H—Ar)), 6.57 (s, 1H), 5.36 (d, J=46.5 Hz, 2H, CFH$_2$), 4.97 (m, 2H, OCH$_2$).

Step 3: A mixture of the 2-fluoromethyl-pyran-4-one derivative obtained in step 2 above (5.0 g, 21.3 mmol) and a methanolic 2M methylamine (53 mL, 106.7 mmol) in methanol was heated to 40° C. for 80 min. The reaction mixture was concentrated to give a dark oil. The residue was purified by column chromatography on silica gel using a gradient of 100% CH$_2$Cl$_2$ to 6% methanol in CH$_2$Cl$_2$ to give a brown solid. The solid was suspended in CH$_2$Cl$_2$ and ether, and then collected by suction filtration. The filtrate was concentrated and crystallized to obtain a second crop. The combined crops were dried in a vacuum oven to give 5-benzyloxy-2-fluoromethyl-2-methyl-1H-pyridin-4-one (2.62 g, 50% yield). HPLC purity (peak area percent) is 93.1% at λ=280 nm using HPLC Method 1 as described above. $^1$H NMR (400 MHz, DMSO-D$_6$) δ (ppm): 8.31 (s, 1H), 7.43-7.36 (m, 5H, H—Ar), 6.36 (s, 1H), 5.48 (d, J=46.9 Hz, 2H, CFH$_2$), 5.01 (s, 2H, OCH$_2$), 3.64 (s, 3H, N—CH$_3$).

Step 4: A mixture of 5-benzyloxy-2-fluoromethyl-2-methyl-1H-pyridin-4-one obtained in step 3 above (0.5 g, 2.02 mmol) in 5 mL of 4.0M HCl solution was heated to 70° C. and then to 120° C. The progress of the reaction was monitored by HPLC Method 1 as described above. After 3 hrs, the reaction mixture was cooled in an ice/salt bath and the pH of the solution was adjusted to 6 with aqueous NaOH. A precipitate formed upon stirring. The solid was collected by suction filtration, and thoroughly washed with cold 0.01M HCl solution, and then with ether. The solid was dried under vacuum in an oven (40° C.) to give the title product, 2-fluoromethyl-5-hydroxy-1-methyl-1H-pyridin-4-one (110 mg). HPLC purity (peak area percent) is >98% at λ=280 nm using HPLC Method 1 as described above. $^1$H NMR (400 MHz, DMSO-D$_6$) δ (ppm): 7.52 (s, 1H), 6.36 (s, 1H), 5.47 (d, J=46.8 2H, CFH$_2$), 3.70 (s, 3H, N—CH$_3$); MS-ESI (m/z): 158.2 [M+1]$^+$, 110.1.

EXAMPLE 17

Preparation of 2-Difluoromethyl-5-hydroxy-1H-pyridin-4-one

Preparation of 5-Benzyloxy-2-difluoromethyl-1H-pyridin-4-one

5-Benzyloxy-2-difluoromethyl-pyran-4-one (0.47 g, 1.9 mmol) was dissolved in ethanol (15 mL) to give a slightly yellow clear solution. Ammonium hydroxide (28-30% aqueous solution, 15 mL, 235 mmol) was added at room temperature. The resulting solution was stirred at ambient temperature for 24 hours. The progress of the reaction was monitored by TLC (CH$_2$Cl$_2$/EtOAc, 7/3, v/v) and HPLC Method 2. Volatiles were removed in vacuo and the residue was purified by column chromatography on silica (95/5 then 85/15 CH$_2$Cl$_2$/MeOH, v/v) to give the title compound as a light yellow solid (0.35 g, 74%) with a HPLC purity (peak percent area) of 98.2%. $^1$H NMR (300 MHz, DMSO-D6) δ (ppm): 10.99 (br. s, 1H), 8.22 (s, 1H), 7.32-7.32 (m, 5H), 7.06 (s, 1H), 6.75 (t, J=55.4 Hz, 1H), 5.23 (s, 2H); MS (m/z) 252 [M+1]$^+$, 192.2, 91.3 (100%).

Preparation of 2-Difluoromethyl-5-hydroxy-1H-pyridin-4-one

5-Benzyloxy-2-difluoromethyl-1H-pyridin-4-one (300 mg, 1.19 mmol) was dissolved in methanol (20 mL) to give clear a yellow solution. Pd/C (55 mg) was added at RT. After purging with hydrogen gas, the mixture was hydrogenated at 50 psi H$_2$ pressure for 15 min. The reaction mixture was filtered through a short pre-treated CELITE™ bed. The filtrate was collected, and the solvent was removed in vacuo to give the title compound as an off-white solid (170 mg, 88%) with an HPLC purity (peak percent area) of 98.8%. HPLC Method 1 is used (see Example 1). $^1$H NMR (300 MHz, DMSO-D$_6$) δ (ppm): 10.3 (br s, 1H), 7.97 (s, 1H), 6.98 (s, 1H), 6.72 (t, J=55.4 Hz, 1H); MS (m/z) 162.2 [M+1]$^+$, 142.1 (100%).

EXAMPLE 18

Preparation of 3-hydroxy-6-methyl-2-(2,2,2-trifluoro-1-hydroxy-ethyl)-1H-pyridin-4-one Preparation of 5-benzyloxy-2-methyl-1H-pyridin-4-one A suspension of 3-Benzyloxy-6-methyl-4-oxo-1,4-dihydro-pyridine-2-carboxylic acid (3.2 g, 0.02 mol) in DMF (30 ml) was heated in an oil bath at 120° C. for 8 hrs. The mixture was cooled to room temperature and the insoluble solid was filtered. The solid was washed with hexane and dried under vacuum for 16 hrs to give 5-benzyloxy-2-methyl-1H-pyridin-4-one (3.32 g, 77% yield).

H-NMR (MeOH-d$_4$) δ 2.30 (s, 1H, CH$_3$), 5.06 (s, 2H, OCH$_2$), 6.34 (s, 1H, CH), 7.29-7.38 (overlapping peaks, 4H, Ph), 7.44-7.46 (overlapping peaks, 2H, CH and 1H of Ph).

Preparation of 5-hydroxy-2-methyl-1H-pyridin-4-one

A solution of 5-benzyloxy-2-methyl-1H-pyridin-4-one (2 g, 9.29 mmol) in methanol (30 ml) and water (8 ml) was placed in a Parr bottle. 10% Pd/C was added and the mixture was hydrogenated at 50 psi for 3 hours. A bed of CELITE™ was placed on a sintered glass, and washed with 0.1N HCl and then water. The content in the Parr bottle was removed from the Parr hydrogenator and flushed with nitrogen. The solution was filtered under suction. The filtrate was evaporated to give a white solid (820 mg, 70% yield).

H-NMR (300 MHz, DMSO-d$_6$) δ 2.178 (apparent s, 1H, CH$_3$), 5.99 (s, 1H, CH), 7.22 (s, 1H CH).

Preparation of 3-hydroxy-6-methyl-2-(2,2,2-trifluoro-1-hydroxy-ethyl)-1H-pyridin-4-one A. 5-Hydroxy-2-methyl-1H-pyridin-4-one (700 mg, 5.59 mol) was suspended in a parallel synthesizer reaction tube. Potassium carbonate (231 mg, 1.67 mmol) and CF$_3$CH(OH)OMe (2.1 ml, 22.36 mmol) were added. The mixture was heated in a sealed tube at 120° C. (metal block temperature) for 2 hrs. The mixture started to solidify and it was cooled. An additional amount of CF$_3$CH(OH)OMe (2.1 ml, 22.36 mmol) was added. The suspension was heated for another 8 hrs at 120° C. The material was cooled and evaporated to dryness. Water (10 ml) was added and the insoluble product was filtered. It was dried under vacuum for 16 hrs at 40° C. Yield (920 mg, 73% yield).

H-NMR (DMSO-d$_6$) δ 2.49 (apparent s, 3H, CH$_3$), 5.39 (dd, J$_{HF1}$=7.2 Hz, J$_{HF2}$=7.2 Hz, J$_{HF3}$=7.2 Hz), 6.04 (br. s, 1H, CH). MS (m/z) 224.1 [M+1]$^+$.

B. Proceeding in a similar manner as A, 2-difluoromethyl-5-hydroxy-1-methyl-1H-pyridin-4-one was converted to 6-difluoromethyl-3-hydroxy-1-methyl-2-(2,2,2-trifluoro-1-hydroxy-ethyl)-1H-pyridin-4-one. $^1$H NMR (DMSO-d$_6$+1 drop of D$_2$O) δ ppm: 7.12 (t, J=52.8 Hz, 1H), 6.56 (s, 1H), 5.83 (b, 1H), 3.79 (s, 3H). $^{19}$F NMR (DMSO-d$_6$+1 drop of D$_2$O) δ ppm: −73.3 (3F), −117.8 (2F). MS (m/z) 274.1 [M+1]$^+$. HPLC conditions: Column: XTerra MS C18 5 μm 4.6×250 mm. Mobile phase: A=the aqueous phase: 4 mM Tris, 2 mM EDTA, pH 7.4; B=the organic phase: CH$_3$CN. The gradient program: B %: 0 min. 5%, 15 min. 55%, 25 min. 55%, 25.05 min. 5%, 30 min. 5%. Flow rate=1 ml/min.; injection volume=5 μL; wavelength: 220, 254, 280, 450 nm. Retention time of 2-Difluoromethyl-5-hydroxy-1-methyl-1H-pyridin-4-one=6.7 min. Retention time of 6-difluoromethyl-3-hydroxy-1-methyl-2-(2,2,2-trifluoro-1-hydroxy-ethyl)-1H-pyridin-4-one=11.4 min.

EXAMPLE 19

Preparation of 3-Hydroxy-2-methyl-5-(2,2,2-trifluoro-1-hydroxy-ethyl)-M-pyridin-4-one Preparation of 3-Benzyloxy-2-methyl-5-(2,2,2-trifluoro-1-hydroxy-ethyl)-1H-pyridin-4-one 3-Benzyloxy-2-methyl-1H-pyridin-4-one (1 g, 4.64 mmol) was mixed with potassium carbonate (0.2 g, 1.45 mmol) and CF$_3$CH(OCH$_3$)OH (4.34 g, 33.36 mmol) in sealed parallel synthesizer reactor and heated at 120° C. metal block temperature for 2 days. The mixture was cooled, and an additional amount of potassium carbonate (2 g, 14.5 mmol) and CF$_3$CH(OCH$_3$)OH (2 g, 15.30 mmol) was added. The mixture was again heated in a sealed tube at 120° C. for 60 hours. The mixture was cooled to room temperature and then evaporated to dryness. The residual material was purified by column chromatography (5% MeOH: dichloromethane) to give 3-benzyloxy-2-methyl-5-(2,2,2-trifluoro-1-hydroxy-ethyl)-1H-pyridin-4-one (0.55 g, 37.8% yield).

H-NMR (300 MHz, DMSO-d$_6$) δ 2.08 (s, 3H, CH$_3$), 5.06 (dd, 2H, CH$_2$Ph, J=11, 8.4 Hz), 5.35 (m, 1H, CHCF$_3$), 7.31-7.35 (m, 5H, Ph), 7.57 (s, 1H, CH).

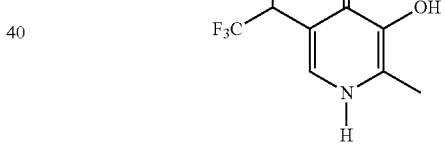

Preparation of 3-Hydroxy-2-methyl-5-(2,2,2-trifluoro-1-hydroxy-ethyl)-1H-pyridin-4-one 3-benzyloxy-2-methyl-5-(2,2,2-trifluoro-1-hydroxy-ethyl)-1H-pyridin-4-one (0.5 g, 1.60 mmol) was dissolved in methanol and hydrogenated over 10% Pd/C for 3 hrs at 50 psi hydrogen on a Parr hydrogenator. The mixture was filtered through CELITE™ and the filtrate was evaporated to give a solid (300 mg, 84.2%).

H-NMR (300 MHz, DMSO-d$_6$) δ 2.20 (s, 3H, CH$_3$), 5.32 (m, 1H, CHCF$_3$), 7.51 (s, 1H, CH).

EXAMPLE 20

Stability studies
The stability of the following products:
(i) 2-difluoromethyl-5-hydroxy-1-methyl-1H-pyridin-4-one;
(ii) 3-hydroxy-1,6-dimethyl-2-(2,2,2-trifluoro-ethyl)-1H-pyridin-4-one;
(iii) 3-hydroxy-1,6-dimethyl-2-(2,2,2-trifluoro-1-hydroxy-ethyl)-1H-pyridin-4-one;

(iv) 2-difluoromethyl-3-hydroxy-1,6-dimethyl-1H-pyridin-4-one;
(v) 2-difluoromethyl-3-hydroxy-1-methyl-1H-pyridin-4-one;
(vi) 3-hydroxy-1-methyl-4-oxo-1,4-dihydro-pyridine-2-carbaldehyde; and
(vii) 2-fluoromethyl-5-hydroxy-1-methyl-1H-pyridin-4-one
in
(1) aqueous 0.01 N HCl;
(2) de-ionized water at pH 5.6;
(3) 50 mM phosphate buffer at pH 7.4; and
(4) aqueous 0.01 N NaOH
was monitored at room temperature over 4-19 hrs by HPLC Methods 1 and 2 as described above.

Under these conditions, it was observed that the di-fluorinated compound (i), the tri-fluorinated compound (ii), and the aldehyde (vi) were stable in all the four media at room temperature for at least 8 hrs.

The trifluoro derivative (iii) was stable in 0.1N HCl, in the 50 mM phosphate buffer at pH 7.4 and in 0.1 N NaOH solution for at least 21 hrs at room temperature.

Freshly prepared solutions of the difluoro compounds (iv) and (v) were stable in aqueous 0.01 N HCl and in de-ionized water at pH 5.6. However, the difluoro compounds (iv) and (v) were almost instantaneously hydrolysed to their corresponding aldehydes either in 50 mM phosphate buffer at pH 7.4 or in aqueous 0.01 N NaOH. In both cases, the corresponding aldehyde was the only major product formed in each case, as monitored by HPLC Method 1.

The mono-fluoro derivative (vii) was stable in MeOH for at least 4 hrs, but decomposed rapidly in aqueous 0.01 N NaOH to form at least 3 decomposition products. In 50 mM phosphate buffer at pH 7.4, about half of the compound (vii) remained after 5 hrs. At least 4 decomposition products were detected by HPLC Method 1.

EXAMPLE 21

Determination of log $K_{BMC}$ of compounds of formula (I) of the present invention and reference drug substances by Bio-partitioning Micellar Chromatrography (BMC).

The BMC determination was conducted on an Aligent HPLC 1100 model equipped with a column heater set at 36.5° C. The chromatographic column was a Kromasil C18 column with guard column (5µ, 150 mm×4.6 mm). The flow rate was 1 ml min$^{-1}$ in the isocratic mode. The mobile phase was 0.04 M Brij35-polyoxyethylene lauryl ether solution or 0.04 M Brij35 solution with 4 mM EDTA, 0.05 M phosphate buffer at pH 7.4 and 9.2 g/L NaCl. EDTA was used in the mobile phase to ensure that the chelator was completely free of metal chelates. A UV variable wavelength detector was used, with the $\lambda_{max}$ selected for each analyte. Thirty-one reference drug substances were analyzed by BMC according to the technique reported by Escuder-Gilabert et al. (Escuder-Gilabert, L., et al., Journal of Chromatography B, 2004, 807, 193-201). The results for the reference drug substances are provided in the table of FIG. 2. The log $K_{BMC}$ and log BB values for the reference drug substances reported in the literature are provided in Columns 3 and 4 of the table. The log $K_{BMC}$ for the reference drug substances measured by us are provided in Columns 1 and 2 of the table. The compounds of formula (I) of the present invention were analyzed by the same chromatography method. The log $K_{BMC}$ values for the compounds of formula (I) of the present invention, using 4 mM EDTA in the mobile phase, are recorded in the table of FIG. 1. The calculated log BB values were computed using the linear regression mathematical equation shown in FIG. 3. The test articles showed calculated log BB values between −1.05 to −0.22. These values fall within the log BB range of the compounds provided in the table of FIGS. 2, and 14 of the drug substances studied have log BB values below zero and are in the negative range.

EXAMPLE 22

A. Preparation of 5-benzyloxy-1-methyl-4-oxo-1,4-dihydro-pyridine-2-carboxylic acid A mixture of 5-benzyloxy-4-oxo-4H-pyran-2-carboxylic acid (20.0 g, 81.2 mmol) and a solution of 2M MeNH$_2$ in methanol (162.5 mL, 325 mmol) was stirred at RT for 16 h. Volatiles were removed under reduced vacuum, and the residue was dissolved in 70 mL of de-ionized water. To the ice-cold mixture was added a 6N HCl solution (13.5 mL, 81.0 mmol) dropwise. The precipitated solid was collected via filtration, and washed with water and acetone to give the title compound as a light yellow solid (18.9 g, 90% yield). $^1$H NMR (400 MHz, DMSO-D$_6$) δ (ppm): 7.82 (s, 1H), 7.45-7.33 (m, 5H), 6.72 (s, 1H), 5.05 (s, 2H) and 3.84 (s, 3H); MS-ESI (m/z): 259.8 [M+1]$^+$, 91.2.

B. Preparation of 3-hydroxy-1-methyl-1H-pyridin-4-one

A suspension of 5-benzyloxy-1-methyl-4-oxo-1,4-dihydro-pyridine-2-carboxylic acid (18.2 g, 70.2 mmol) in 100 mL of DMF was stirred at oil bath temperature (130-140° C.) for 1.5 h. The reaction mixture was concentrated in vacuo, and the residual oil was diluted with dichloromethane (10 mL) and ethyl acetate (80 mL). The precipitated solid was collected by suction filtration to give 3-benzyloxy-1-methyl-1H-pyridin-4-one as a yellow powder (14.2 g, 94% yield). MS-ESI (m/z): 215.7 [M+1]$^+$, 91.2.

A mixture of 3-benzyloxy-1-methyl-1H-pyridin-4-one (14.1 g, 65.5 mmol) and 10% Pd/C (1.20 g) in methanol was subjected to hydrogenation in a Parr apparatus under 50 psi pressure of hydrogen for 70 min. The mixture was filtered through a pad of CELITE™, the filtrate was concentrated to dryness, and the residue was triturated with acetone. The solid was then collected by suction filtration. The title compound was obtained as a light-brown powder (7.13 g, 87% yield) after vacuum oven drying. $^1$H NMR (400 MHz, DMSO-D$_6$) δ (ppm): 7.49 (br. s, 1H), 7.38 (s, 1H), 6.12 (br. s, 1H) and 3.63 (s, 3H); MS-ESI (m/z): 125.7 [M+1]$^+$.

EXAMPLE 23

A. Preparation of 3-Hydroxy-1-methyl-2-(2,2,2-trifluoro-1-hydroxy-ethyl)-1H-pyridin-4-one A mixture of 3-hydroxy-1-methyl-1H-pyridin-4-one (7.60 g, 60.7 mmol) and K$_2$CO$_3$ (0.84 g, 6.07 mmol) in trifluoroacetaldehyde methyl hemiacetal (26 mL) was sealed in a parallel reactor and stirred for overnight at 120° C. The reaction mixture was evaporated to dryness, and the residue was purified by flash column chromatography on silica gel using a mixture of isopropyl alcohol and a conc. NH$_4$OH solution (80/20, v/v) as eluant. Pure fractions were combined together and evaporated to give the title compound as a white solid (2.32 g, 17% yield). HPLC purity (peak area percent) of this compound is 99% at λ=254 nm. $^1$H NMR (400 MHz, DMSO-D$_6$) δ (ppm): 7.59 (d, J=7.2 Hz, 1H), 6.20 (d, J=7.4 Hz, 1H), 5.80 (q, J=8.5 Hz, 1H) and 3.83 (s, 3H); MS-ESI (m/z): 223.7 [M+1]$^+$, 206, 158. Other fractions were combined to give a second crop of the product (8.26 g, 61% yield). HPLC purity (peak area percent) of this compound is 98% at λ=254 nm. HPLC method: Column: Waters Symmetry C18; 5 μm, 3.9×150 mm; Mobile phase: A=the aqueous phase: 0.035% $HClO_4$ pH 2.5; B=the organic phase: $CH_3CN$; gradient: % B: 0 min—10%, 10 min—90%, 12 min—90%, 15 min—10%; flow rate: 1 mL/min; wavelength: 220, 254, 280 nm.

B. Preparation of 3-hydroxy-1-methyl-2-(2,2,2-trifluoro-ethyl)-1H-pyridin-4-one A solution of NaOH (1.77 g dissolved in 20 mL, 44.4 mmol) in de-ionized water was added dropwise to a suspension of 3-hydroxy-1-methyl-2-(2,2,2-trifluoro-1-hydroxy-ethyl)-1H-pyridin-4-one (9.00 g, 40.3 mmol) in methanol (100 mL), and followed by benzyl bromide (5.28 mL, 44.4 mmol) at room temperature. The resulting suspension was refluxed for 3.5 h, and then stirred at RT for overnight. Methanol was removed under vacuum using the rotary evaporator, and the residue was diluted with water and extracted two times with $CH_2Cl_2$ (2×100 mL). The combined organic fractions were washed with brine, dried over anhydrous sodium sulfate, filtered and concentrated to dryness. The residue was purified by flash column chromatography on silica gel using a mixture of methanol and ethyl acetate (10/90, v/v) as eluant. Fractions rich in the product were pooled together and evaporated to dryness to give 4 g of 3-benzyloxy-1-methyl-2-(2,2,2-trifluoro-1-hydroxy-ethyl)-1H-pyridin-4-one as a solid.

To a suspension of 3-benzyloxy-1-methyl-2-(2,2,2-trifluoro-1-hydroxy-ethyl)-1H-pyridin-4-one (4 g) in $CH_2Cl_2$ (80 mL) was added $Et_3N$ (2.40 mL, 17.5 mmol), followed by methanesulfonyl chloride (1.25 mL, 16.2 mmol) at ice-water bath temperature. The resulting mixture was then stirred for 3 h. The reaction mixture was quenched with water and extracted twice with $CH_2Cl_2$ (2×50 mL). The combined organic fractions were washed with brine and dried over anhydrous sodium sulfate, filtered and concentrated to dryness. The residue was purified by flash column chromatography on silica gel using a mixture of $CH_2Cl_2$ and MeOH (95/5, v/v) as eluant, thereby affording the product, methanesulfonic acid 1-(3-benzyloxy-1-methyl-4-oxo-1,4-dihydro-pyridin-2-yl)-2,2,2-trifluoro-ethyl ester (0.97 g, 19.4% yield). MS-ESI (m/z): 391.9 $[M+1]^+$, 206, 91.

A mixture of methanesulfonic acid 1-(3-benzyloxy-1-methyl-4-oxo-1,4-dihydro-pyridin-2-yl)-2,2,2-trifluoro-ethyl ester (2.80 g, 7.15 mmol) and 10% Pd/C (0.56 g) in ethyl alcohol was subjected to hydrogenation in a Parr apparatus under 50 psi hydrogen pressure for 90 min. The mixture was filtered through a pad of CELITE™, and the filtrate was concentrated to dryness. The residue was purified by flash column chromatography on silica gel using a mixture of isopropyl alcohol and a conc. $NH_4OH$ solution (90/10, v/v) as eluant. Fractions rich in the product were pooled together and evaporated to dryness, thereby affording 3-hydroxy-1-methyl-2-(2,2,2-trifluoro-ethyl)-1H-pyridin-4-one (first crop: 143 mg, 9.7% yield, second crop: 240 mg, 16.2% yield). $^1$H NMR (90 MHz, $CD_3OD$) δ (ppm): 7.66 (d, J=7.2 Hz, 1H), 6.41 (d, J=7.4 Hz, 1H), 3.89 (q, J=10.2 Hz, 1H) and 3.82 (s, 3H); MS-ESI (m/z): 208 $[M+1]^+$, 188.2, 168.2. HPLC purity (peak area percent) of both fractions are about 98% at λ=254 nm, RT=3.75 min (HPLC method is described in Part A above).

EXAMPLE 24

HPLC Methods Used in the Preparation of Compounds of the Present Invention

The HPLC methods used (Methods 1 to 4) in the monitoring of the synthesis of the compounds of the present invention and their intermediates are described below:
Column: XTerra MS C18, 4.6×250 mm
A=Aqueous phase: 4 mM Tris, 2 mM EDTA, pH 7.4
B=Organic phase: $CH_3CN$
Flow rate=1.0 mL/min
Injection volume=5 μL
Wavelength (λ): 220, 254, 280, 450 nm
Method 1: Gradient method; min-B % 0-5, 15-55, 25-55, 25.05-5, 30-5.
Method 2: Isocratic method; aqueous:organic=80:20.
Method 3: Gradient method: min-B % 0-5, 15-55, 32-55, 35-5, 40-5
Method 4
A=Aqueous phase: 8 mM Tris, 4 mM EDTA, pH 7.4
B=Organic phase: $CH_3CN$
Flow rate=1.0 mL/min
Injection volume=5 μL
Wavelength=220, 254, 280, 450 nm
Gradient: min-B % 0-5, 15-55, 25-55, 25.05-5, 30-5

EXAMPLE 25

Preparation of 5-Hydroxy-1-methyl-2-(2,2,2-trifluoro-ethyl)-1H-pyridin-4-one

A. Preparation of 5-Benzyloxy-2-(2,2,2-trifluoro-1-hydroxy-ethyl)-pyran-4-one The entire experiment was performed under an inert atmosphere by bubbling argon gas into the ice-salt cooled reaction mixture. To a cloudy solution of 5-benzyloxy-4-oxo-4H-pyran-2-carbaldehyde (5.00 g, 21.7 mmol) in dry tetrahydrofuran (185 mL) previously purged with argon for 35 min was added trimethyl(trifluoromethyl)silane (10.8 g, 76.0 mmol) dropwise, followed by caesium fluoride (0.34 g, 2.2 mmol). The color of the reaction mixture turned to yellow and almost clear within a min. TLC was used to monitor the reaction (eluant: 50:50, ethyl acetate:hexanes, v:v). The reaction was completed within 10 min. The reaction mixture was quenched with a 6.0N hydrochloric acid solution (20 mL) under cooling, followed by addition of a brine solution (50 mL). The mixture was stirred for 10 min, and then transferred to a separatory funnel. The organic THF fraction was collected, and then concentrated in vacuo to about 10 mL using the rotary evaporator. The residual solution was diluted with dichloromethane (80 mL). The mixture was transferred to a separatory funnel, and the separated dichloromethane layer was collected, dried over $Na_2SO_4$ and filtered. Upon concentration under reduced pressure, a first crop of the titled compound was obtained as a solid product (3.72 g, 57% yield, HPLC Method 1 (Example 24), RT=16.8 min, HPLC purity (peak percent area): 96% at λ=280 nm). $^1$H NMR (DMSO-$d_6$+$D_2O$) δ ppm: 8.20 (s, 1H), 7.36 (br m, 5H), 6.57 (s, 1H), 5.11 (q, J=7 Hz, 1H), 4.92 (s, 2H).

B. Preparation of 5-Benzyloxy-1-methyl-2-(2,2,2-trifluoro-1-hydroxy-ethyl)-1H-pyridin-4-one In each of four parallel synthesis tubes equipped with a magnetic stir bar was placed 5-benzyloxy-2-(2,2,2-trifluoro-1-hydroxy-ethyl)-pyran-4-one (0.90 g, 3.0 mmol), and a 2M methylamine solution in MeOH (5.5 mL, 11 mmol). The resulting solution was heated to reflux. The reaction was completed in 60 min. The solutions from the four reaction tubes were combined, and evaporated to dryness to give a semi solid mixture. The mixture was taken up in dichloromethane (15 mL) to give a thick solution. On standing, a solid product precipitated out to give the first crop of the title compound (2.90 g, 77% yield, HPLC Method 1 (Example 24); RT=13.0 min, HPLC purity (peak percent area): 99.5% at λ=280 nm). $^1$H NMR (DMSO-d$_6$+D$_2$O) δ ppm: 7.64 (s, 1H), 7.37 (m, 5H), 6.49 (s, 1H), 5.38 (q, J=6.5 Hz, 1H), 4.97 (s, 2H), 3.69 (s, 3H).

C. Preparation of Methanesulfonic acid 1-(5-benzyloxy-1-methyl-4-oxo-1,4-dihydro-pyridin-2-yl)-2,2,2-trifluoro-ethyl ester To a tap-water cooled suspension of 5-benzyloxy-1-methyl-2-(2,2,2-trifluoro-1-hydroxy-ethyl)-1H-pyridin-4-one (1.81 g, 5.8 mmol) in dichloromethane (95 mL) was added triethylamine (0.80 mL, 5.8 mmol) dropwise, followed by methanesulfonyl chloride (0.45 mL, 5.8 mmol). The suspension cleared and a slightly cloudy solution was obtained. The progress of the reaction was monitored by HPLC Method 1 (Example 24), which indicated about 75% conversion at this time. Another portion of triethylamine (0.30 mL, 2.1 mmol) and methanesulfonyl chloride (0.160 mL, 2.1 mmol) was added to the reaction mixture, and a bright yellow clear solution resulted. The reaction was completed within 10 min after the addition. The resulting solution was washed with a brine solution (2×50 mL). The organic layer was dried over Na$_2$SO$_4$, and then filtered. To the filtrate was added morpholine polymer-bound beads (1% cross-linked w/DVB, 200-400 mesh, 2.5-4.0 mmol N/g, 4.3 g), and the mixture was vortexed for 1 h. The solid morpholine beads were removed by filtration. The filtrate was evaporated to dryness, and the residual oil was taken up in dichloromethane and ethyl ether, and a solid product was obtained upon stirring. A first crop of the title compound was collected by filtration (1.80 g, 80% yield, HPLC Method 1 (Example 24); RT=15.0 min, HPLC purity (peak percent area): 99.3% at λ=280 nm). $^1$H NMR (DMSO-d$_6$) δ ppm: 7.77 (s, 1H), 7.40 (m, 5H), 6.61 (q, J=6 Hz, 1H), 6.43 (s, 1H), 5.01 (s, 2H), 3.77 (s, 3H), 3.50 (s, 3H).

D. Preparation of 5-Hydroxy-1-methyl-2-(2,2,2-trifluoro-ethyl)-1H-pyridin-4-one

In a 500-mL reaction vessel was placed methanesulfonic acid 1-(5-benzyloxy-1-methyl-4-oxo-1,4-dihydro-pyridin-2-yl)-2,2,2-trifluoro-ethyl ester (1.80 g, 4.60 mmol), and ethanol (120 mL). The mixture was sonicated to give a clear solution. To the solution was added 1.80 g of Pd/C (10 wt. %, dry basis, on activated carbon, wet, Degussa type E101 NE/W). Hydrogenation was carried out under a hydrogen atmosphere set at a pressure of 50 psi. The reaction was completed within 90 min. The reaction mixture was diluted with methanol (120 mL), and the resulting mixture was sonicated for 10 min. The reaction mixture was then filtered through a short hydrochloric acid pre-treated CELITE™ bed. The filtrate was collected, and concentrated in vacuo to a volume of about 100 mL. To the resulting solution was added morpholine polymer-bound beads (1% cross-linked w/DVB, 200-400 mesh, 2.5-4.0 mmol N/g, 5.2 g), and the mixture was vortexed for 3 h. The morpholine beads were removed by filtration. Upon partial concentration in vacuo, a solid separated and the first crop of the title compound was obtained as the free base (0.74 g, 77% yield, HPLC Method 1 (Example 24); RT=8.2 min, HPLC purity (peak percent area): 98.7% at λ=280 nm). $^1$H NMR (CD$_3$OD) δ ppm: 7.55 (s, 1H), 6.52 (s, 1H), 3.77 (q, J=10 Hz, 2H), 3.78 (s, 3H); MS-ESI (m/z): 208.2 ([M+1]$^+$, 100%), 188.2, 139.2.

EXAMPLE 26

Preparation of 3-Hydroxy-2-hydroxymethyl-1-methyl-6-(2,2,2-trifluoro-ethyl)-1H-pyridin-4-one In a parallel synthesis tube equipped with a magnetic stir bar was placed 5-hydroxy-1-methyl-2-(2,2,2-trifluoro-ethyl)-1H-pyridin-4-one (0.70 g, 3.40 mmol), a 36.5% by wt. formaldehyde solution (8 mL, 107 mmol) and a 6.00 N sodium hydroxide solution (0.62 mL, 3.70 mmol). The resulting solution was heated to about 40° C. for 3 h. The progress of the reaction was monitored by HPLC (Example 24, HPLC method 2: RT of 5-hydroxy-1-methyl-2-(2,2,2-trifluoro-ethyl)-1H-pyridin-4-one and 3-hydroxy-2-hydroxymethyl-1-methyl-6-(2,2,2-trifluoro-ethyl)-1H-pyridin-4-one are 4.4 and 4.2 min, respectively), which indicated that there was about 90% conversion at this time. To the solution was further added a 6.00 N NaOH solution (40 μL, 0.24 mmol). The reaction was heated at about 40° C. for another 1.5 h. The reaction mixture was cooled in an ice-water bath, and the pH of the solution was adjusted to 6 by adding a 6.00 N hydrochloric acid solution (475 μL, 2.85 mmol). A lot of solid separated upon stirring. The reaction mixture was concentrated. The solid product 3-hydroxy-2-hydroxymethyl-1-methyl-6-(2,2,2-trifluoro-ethyl)-1H-pyridin-4-one was collected by filtration and thoroughly washed with deionized water, then dried (0.62 g, 77% yield, HPLC Method 2 (Example 24), RT=4.2 min, HPLC purity (peak percent area): 94% at λL=280 nm). Recrystallization of the solid in methanol gave a 1$^{st}$ crop of purer 3-hydroxy-2-hydroxymethyl-1-methyl-6-(2,2,2-trifluoro-ethyl)-1H-pyridin-4-one (250 mg, HPLC purity (peak percent area): 98% at λ=280 nm). $^1$H NMR (DMSO-d$_6$) δ ppm: 6.28 (s, 1H), 4.66 (s, 2H), 3.95 (q, J=11 Hz, 2H), 3.73 (s, 3H). MS-ESI (m/z): 238.3 [M+1]$^+$, 220.1, 192.2 (100%).

EXAMPLE 27

Preparation of 3-Hydroxy-1,2-dimethyl-6-(2,2,2-trifluoro-ethyl)-1H-pyridin-4-one In a parallel synthesis tube equipped with a magnetic stir bar, 3-hydroxy-2-hydroxymethyl-1-methyl-6-(2,2,2-trifluoro-ethyl)-1H-pyridin-4-one (0.50 g, 2.11 mmol) was suspended in methanol (9 mL). A clear solution resulted upon addition of a 6.00 N sodium hydroxide solution (0.39 mL, 2.32 mmol). Benzyl bromide (0.32 mL, 2.69 mmol) was then added, and the resulting solution was heated to reflux for 60 min. The reaction was monitored by HPLC Method 1 (Example 24), which indicated that about 15% of the starting material still remained. An additional solution of 6.00 N sodium hydroxide solution (95 μL, 0.57 mmol) and benzyl bromide (85 μL, 0.71 mmol) were added to the reaction mixture, and the resulting solution was heated to reflux for another 30 min. The reaction mixture was purified by column chromatography on silica (methanol:dichloromethane 5:100 to 8:100 v:v) to give 3-benzyloxy-2-hydroxymethyl-1-methyl-6-(2,2,2-trifluoro-ethyl)-1H-pyridin-4-one as a solid (0.34 g, 49% yield, HPLC Method 1 (Example 24), RT=13.1 min, HPLC purity (peak percent area): 96.2% at λ=280 nm). The product was used directly in the next step without further characterization.

To a suspension of 3-benzyloxy-2-hydroxymethyl-1-methyl-6-(2,2,2-trifluoro-ethyl)-1H-pyridin-4-one (0.34 g, 1.04 mmol) in acetonitrile (15 mL), was added thionyl chloride (0.38 mL, 5.19 mmol) at room temperature. A clear solution resulted and the reaction was completed within 10 min. The reaction mixture was evaporated to dryness to give the crude 3-benzyloxy-2-chloromethyl-1-methyl-6-(2,2,2-trifluoro-ethyl)-1H-pyridin-4-one as an oil, which was taken up in ethanol (15 mL) to give a clear solution. Sodium borohydride (430 mg, 11.4 mmol) was added to the solution portionwise. The reaction mixture was stirred for another 10 min, and the progress of the reaction was monitored by TLC (methanol/dichloromethane, 1/10 v/v as eluant). There was still some unreacted chloride derivative present at this time. Additional sodium borohydride (360 mg, 9.5 mmol) was added in several portions. The reaction mixture was stirred for another 10 min. The reaction mixture was purified by column chromatography on silica gel (methanol/dichloromethane, 1/20 v/v as eluant) to give 3-benzyloxy-1,2-dimethyl-6-(2,2,2-trifluoro-ethyl)-1H-pyridin-4-one as an oil (0.20 g, 61% for the two combined steps, HPLC Method 1 (Example 24), RT=15.1 min, HPLC purity (peak percent area): 92% at $\lambda$=280 nm). This material, 3-benzyloxy-1,2-dimethyl-6-(2,2,2-trifluoro-ethyl)-1H-pyridin-4-one (0.20 g, 0.64 mmol) was taken up in methanol (25 mL) to give a clear solution. To the solution was added Pd/C (10 wt. %, dry basis, on activated carbon, wet, Degussa type E101 NE/W, 90 mg). The hydrogenation reaction was conducted under a hydrogen pressure of 50 psi. The reaction was completed in 30 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was evaporated to give the first crop of 3-hydroxy-1,2-dimethyl-6-(2,2,2-trifluoro-ethyl)-1H-pyridin-4-one as a solid product (free base, 74 mg, 52% yield), HPLC Method 1 (Example 24), RT=9.9 min, HPLC purity (peak percent area): 96.4% at $\lambda$=280 nm). $^1$H NMR (DMSO-$d_6$) $\delta$ ppm: 6.25 (s, 1H), 3.94 (q, J=11 Hz, 2H), 3.57 (s, 3H), 2.32 (s, 3H). MS-ESI (m/z) 222.2 ([M+1]$^+$, 100%), 202.3, 153.2.

EXAMPLE 28

Preparation of 5-Hydroxy-1-methyl-2-(2,2,2-trifluoro-1-hydroxy-ethyl)-1H-pyridin-4-one A mixture of 5-benzyloxy-1-methyl-2-(2,2,2-trifluoro-1-hydroxy-ethyl)-1H-pyridin-4-one (3.1 g, 9.9 mmol) and methanol (60 mL) was sonicated to give a clear solution. To the solution was added Pd/C (10 wt. %, dry basis, on activated carbon, wet, Degussa type E101 NE/W, 0.58 g). The debenzylation reaction was conducted in a Parr hydrogenator under an atmosphere of hydrogen pressurized to 50 psi. The reaction was completed within 20 min. The reaction mixture was diluted with MeOH (100 mL), sonicated for about 20 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was collected and concentrated in vacuo to give 5-hydroxy-1-methyl-2-(2,2,2-trifluoro-1-hydroxy-ethyl)-1H-pyridin-4-one as a solid product (2.05 g, 92% yield, HPLC Method 1 (Example 24), RT=7.4 min, HPLC purity (peak percent area): 99.4% at $\lambda$=280 nm). $^1$H NMR (DMSO-$d_6$+D$_2$O) $\delta$ ppm: 7.50 (s, 1H), 6.50 (s, 1H), 5.37 (q, J=6.5 Hz, 1H), 3.67 (s, 3H); MS-ESI (m/z) 224.2 [M+1]$^+$, 206.2, 155.2 (100%), 140.1, 126.1.

EXAMPLE 29

Preparation of 3-Hydroxy-2-hydroxymethyl-1-methyl-6-(2,2,2-trifluoro-1-hydroxy-ethyl)-1H-pyridin-4-one In each of three parallel synthesis tubes equipped with a magnetic stir bar was placed 5-hydroxy-1-methyl-2-(2,2,2-trifluoro-1-hydroxy-ethyl)-1H-pyridin-4-one (0.50 g, 2.24 mmol), a 36.5% by wt formaldehyde solution (6 mL, 80.4 mmol), and a 6.00 N sodium hydroxide solution (0.45 mL, 2.7 mmol). The resulting solution was heated to about 40° C. for overnight. Analysis by HPLC Method 1 (Example 24) indicated consumption of the starting material. The contents of the three tubes were combined, and the resulting solution was cooled in an ice-water bath. A 6.00 N hydrochloric acid solution (1.1 mL, 6.6 mmol) was added to adjust the pH of the solution to about 6. The mixture was concentrated in vacuo to remove most of the solvent to give a solid/liquid mixture. To the mixture was added methanol (100 mL), and the mixture was stirred for 1 h. The first crop of the solid was collected by suction filtration and washed with de-ionized water thoroughly to give 3-hydroxy-2-hydroxymethyl-1-methyl-6-(2,2,2-trifluoro-1-hydroxy-ethyl)-1H-pyridin-4-one (0.83 g, 48% yield, HPLC Method 1 (Example 24), RT=7.7 min, HPLC purity (peak percent area): 99.2% at $\lambda$=280 nm). $^1$H NMR (DMSO-$d_6$+D$_2$O) $\delta$ ppm: 6.53 (s, 1H), 5.54 (q, J=6.5 Hz, 1H), 4.67 (s, 2H), 3.76 (s, 3H); MS-ESI (m/z) 254.1 [M+1]$^+$, 236.1, 208.1 (100%), 139.2.

EXAMPLE 30

Preparation of 3-Hydroxy-1,2-dimethyl-6-(2,2,2-trifluoro-1-hydroxy-ethyl)-1H-pyridin-4-one A. Preparation of 3-Benzyloxy-2-hydroxymethyl-1-methyl-6-(2,2,2-trifluoro-1-hydroxy-ethyl)-1H-pyridin-4-one A 6.00 N sodium hydroxide solution (785 µL, 4.71 mmol) was added to a suspension of 3-hydroxy-2-hydroxymethyl-1-methyl-6-(2,2,2-trifluoro-1-hydroxy-ethyl)-1H-pyridin-4-one (1.08 g, 4.26 mmol) in methanol (5 mL). Benzyl bromide (650 µL, 5.46 mmol) was added to the clear solution, and the resulting solution was heated to reflux for 45 min Some solid had separated out in the solution. Analysis of the reaction mixture using HPLC Method 1 (Example 24) indicated that the starting material was consumed. The reaction mixture was allowed to cool down to room temperature, and the first crop of solid product was collected by suction filtration, and washed with acetonitrile. The title compound was thus obtained as a solid product (1.11 g, 76% yield, HPLC Method 1 (Example 24), RT=12.6 min, HPLC purity (peak percent area): 99% at $\lambda$=280 nm). $^1$H NMR (DMSO-$d_6$+D$_2$O) $\delta$ ppm: 7.36 (m, 5H), 6.59 (s, 1H), 5.53 (q, J=6.5 Hz, 1H), 5.01 (s, 2H), 4.58 (s, 2H), 3.72 (s, 3H).

B. Preparation of 3-Benzyloxy-1,2-dimethyl-6-(2,2,2-trifluoro-1-hydroxy-ethyl)-1H-pyridin-4-one To a suspension of 3-benzyloxy-2-hydroxymethyl-1-methyl-6-(2,2,2-trifluoro-1-hydroxy-ethyl)-1H-pyridin-4-one (0.31 g, 0.90 mmol) in acetonitrile (8 mL) was added thionyl chloride (0.33 mL, 4.5 mmol) at room temperature. A clear solution resulted. The reaction was completed in 10 min. The reaction mixture was evaporated to dryness to give crude 3-benzyloxy-2-chloromethyl-1-methyl-6-(2,2,2-trifluoro-1-hydroxy-ethyl)-1H-pyridin-4-one as an oil. The crude oil obtained was taken up in ethanol (10 mL) to give a clear solution. To the solution was added sodium borohydride (380 mg, 10 mmol) in several portions. The reaction was completed within a few min. The reaction mixture was diluted with methanol. The resulting clear solution was evaporated to dryness to give a solid. The solid was repeatedly extracted with dichloromethane. The combined dichloromethane solutions were combined and evaporated to dryness. Purification of the residue by column chromatography on silica gel (methanol/dichloromethane, 5/100 to 8/100 v/v) afforded the title compound (0.20 g, 67% yield, HPLC Method 1 (Example 24), RT=14.4 min). $^1$H NMR (DMSO-d$_6$+D$_2$O) δ ppm: 7.36 (m, 5H), 6.53 (s, 1H), 5.50 (q, J=6.5 Hz, 1H), 5.00 (s, 2H), 3.56 (s, 3H), 2.24 (s, 3H).

C. Preparation of 3-Hydroxy-1,2-dimethyl-6-(2,2,2-trifluoro-1-hydroxy-ethyl)-1H-pyridin-4-one A suspension of 3-benzyloxy-1,2-dimethyl-6-(2,2,2-trifluoro-1-hydroxy-ethyl)-1H-pyridin-4-one (190 mg, 0.58 mmol) and methanol (30 mL) was sonicated for a few min. The addition of a 6.00 N hydrochloric acid solution (50 µL, 0.30 mmol) gave a clear solution. To the solution was added Pd/C (10 wt. %, dry basis, on activated carbon, wet, Degussa type E101 NE/W, 80 mg). The debenzylation reaction was conducted under a hydrogen pressure of 50 psi. The reaction was completed within 30 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The pH of the filtrate was adjusted to 6 by addition of a solution of 6.00 N sodium hydroxide (ca. 50 µL), and then concentrated in vacuo. The first crop of the solid was collected by suction filtration and washed with deionized water thoroughly to give 3-hydroxy-1,2-dimethyl-6-(2,2,2-trifluoro-1-hydroxy-ethyl)-1H-pyridin-4-one (54 mg, 39% yield, HPLC Method 1 (Example 24), RT=9.4 min, HPLC purity (peak percent area): 95.8% at λ=280 nm). $^1$H NMR (CD$_3$OD) δ ppm: 6.78 (s, 1H), 5.51 (q, J=6.5 Hz, 2H), 3.80 (s, 3H), 2.50 (s, 3H); MS-ESI (m/z) 238.2 [M+1]$^+$, 169.2, 154.2 (100%), 140.1.

EXAMPLE 31

Preparation of 6-Difluoromethyl-3-hydroxy-1-methyl-2-(2,2,2-trifluoro-1-hydroxy-ethyl)-1H-pyridin-4-one A suspension of 2-difluoromethyl-5-hydroxy-1-methyl-1H-pyridin-4-one (0.50 g, 2.85 mmol), CF$_3$CH(OH)OCH$_3$ (2.37 g, 18.2 mmol) and potassium carbonate (0.122 g, 0.88 mmol) in a sealed parallel reactor test tube was heated to about 100° C. The progress of the reaction was monitored by HPLC Method 1 (Example 24), and only one major product peak was detected (HPLC peak percent area was about 20% after 1.5 h, and 38% after 3 h). The reaction mixture was heated for another 21 h, then cooled down to RT, and some white solid separated. The solid was collected by suction filtration. HPLC analysis of the solid dissolved in methanol showed the presence of 2-difluoromethyl-5-hydroxy-1-methyl-1H-pyridin-4-one and 6-difluoromethyl-3-hydroxy-1-methyl-2-(2,2,2-trifluoro-1-hydroxy-ethyl)-1H-pyridin-4-one in 18/82 ratio. A portion of the solid was purified by column chromatography on silica gel (conc. NH$_4$OH/isopropanol 10/100 v/v as eluant) to afford 6-difluoromethyl-3-hydroxy-1-methyl-2-(2,2,2-trifluoro-1-hydroxy-ethyl)-1H-pyridin-4-one (35 mg). HPLC Method 1 (Example 24), RT=11.3 min, HPLC purity (peak percent area): 97.9% at λ=280 nm. $^1$H NMR (DMSO-d$_6$+1 drop of D$_2$O) δ ppm: 7.12 (t, J=52.8 Hz, 1H), 6.56 (s, 1H), 5.83 (b, 1H), 3.79 (s, 3H). $^{19}$F NMR (DMSO-d$_6$+1 drop of D$_2$O) δ ppm: −73.3 (3F), −117.8 (2F). MS-ESI (m/z) 274.1 [M+1]$^+$, 256.1, 228.1, 208.1 (100%), 180.1.

EXAMPLE 32

Preparation of 3-Hydroxy-2-methyl-5-(2,2,2-trifluoro-1-hydroxy-ethyl)-1H-pyridin-4-one

A. Preparation of 3-Benzyloxy-2-methyl-1H-pyridin-4-one

To a suspension of maltol (126 g, 1.0 mol) and methanol (450 mL) in a 2 L 3-necked round bottom flask equipped with a mechanical stirrer was added a 10.0 N sodium hydroxide solution (110 mL, 1.1 mol). A clear solution resulted upon stirring. Benzyl chloride (138 mL, 1.2 mol) was then added, and the resulting solution was heated to reflux for 1.5 h. To the reaction mixture was further added a 10.0 N sodium hydroxide (20 mL, 0.2 mol) and benzyl chloride (27 mL, 0.23 mol), and the reaction mixture was heated to reflux for another 2 h. The progress of the reaction was monitored by HPLC Method 4 (Example 24), and the amount of remaining unreacted maltol was about 2%. The reaction mixture was stirred overnight. The mixture was cooled to RT and filtered. The filtrate was concentrated in vacuo to a volume of about 300 mL, as two phases could be observed. The top layer was collected via separatory funnel, and was concentrated under reduced pressure to give 3-(benzyloxy)-2-methyl-4H-pyran-4-one as an oil (220 g, 95% yield, HPLC Method 4 (Example 24), RT=15.5 min, HPLC purity (peak percent area): 95% at λ=280 nm). $^1$H NMR (DMSO-d$_6$) δ ppm: 8.04 (d, J=5.5 Hz, 1H), 7.37, (m, 5H), 6.37 (d, J=5.5 Hz, 1H), 5.02 (s, 2H), 2.12 (s, 3H).

A clear solution of 3-(benzyloxy)-2-methyl-4H-pyran-4-one (150 g, 0.69 mol), ethanol (300 mL) and ammonium hydroxide (28.0-30.0% solution, 690 mL, 10.5 mol) in a 2 L 3-necked round bottom flask equipped with a mechanical stirrer was heated to reflux for 5 h. The reaction mixture was allowed to cool to room temperature, and a further 230 mL of ammonium hydroxide (3.5 mol) was added. The resulting solution was heated to reflux for another 3.5 h, then allowed to cool to RT and stirred for overnight. A solid product had separated, and was collected by suction filtration. Thus, 95 g of 3-benzyloxy-2-methyl-1H-pyridin-4-one (64% yield) was obtained as a first crop. HPLC Method 4 (Example 24), RT=10.7 min, HPLC purity (peak percent area): 99% at λ=280 nm)). $^1$H NMR (DMSO-d$_6$) δ ppm: 11.3 (br s, 1H), 7.46 (s, 1H), 7.35, (m, 5H), 6.13 (s, 1H), 5.04 (s, 2H), 2.05 (s, 3H); $^1$H NMR (DMSO-d$_6$+D$_2$O) δ ppm: 7.47 (d, J=7.0 Hz, 1H), 7.39, (m, 5H), 6.20 (d, J=7.0 Hz, 1H), 5.01 (s, 2H), 2.03 (s, 3H).

B. Preparation of 3-Benzyloxy-2-methyl-5-(2,2,2-trifluoro-1-hydroxy-ethyl)-1H-pyridin-4-one A mixture of 3-benzyloxy-2-methyl-1H-pyridin-4-one (10.0 g, 46.4 mmol), potassium carbonate (19 g, 138 mmol), and CF$_3$CH(OH)OCH$_3$ (35 mL, 0.35 mol) in a 500 mL 3-necked round bottom flask equipped with a mechanical stirrer was heated to reflux for 6 days. The progress of the reaction was monitored by HPLC Method 3 (Example 24). Analysis of the HPLC data indicated that there was about 42% conversion. The reaction was stopped, and dichloromethane and deionized water were added. The organic fraction was collected, washed with brine, dried over $Na_2SO_4$, filtered and concentrated to dryness. Purification of the residue by column chromatography on silica (methanol/dichloromethane 2/100 to 5/100 v:v) afforded 3-benzyloxy-2-methyl-5-(2,2,2-trifluoro-1-hydroxy-ethyl)-1H-pyridin-4-one as a solid product (3.5 g, 24% yield, HPLC Method 3 (Example 24), RT=14.3 min). $^1$H NMR (DMSO-$d_6$) δ ppm: 11.68 (br s, 1H), 7.58 (s, 1H), 7.35, (m, 5H), 5.34 (q, J=7.3 Hz, 1H), 5.06 (m, 2H), 2.08 (s, 3H); MS-ESI (m/z) 313.7 [M+1]$^+$, 206.1, 91.1 (100%).

C. Preparation 3-Hydroxy-2-methyl-5-(2,2,2-trifluoro-1-hydroxy-ethyl)-1H-pyridin-4-one A mixture of 3-benzyloxy-2-methyl-5-(2,2,2-trifluoro-1-hydroxy-ethyl)-1H-pyridin-4-one (1.00 g, 3.19 mmol) and methanol (30 mL) was sonicated to give a clear solution. Pd/C (10 wt %, dry basis, on activated carbon, wet, Degussa type E101 NE/W, 0.158 g) was added. The debenzylation reaction was conducted under a hydrogen atmosphere pressurized to 50 psi. The reaction was completed in 20 min. The reaction mixture was diluted with methanol (30 mL), sonicated for 10 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was collected and concentrated in vacuo to give 3-hydroxy-2-methyl-5-(2,2,2-trifluoro-1-hydroxy-ethyl)-1H-pyridin-4-one as a solid product (0.59 g, 83% yield, HPLC Method 1 (Example 24), RT=7.9 min, HPLC purity (peak percent area): 99.5% at λ=280 nm). $^1$H NMR (DMSO-$d_6$) δ ppm: 11.72, (br s, 1H), 7.51 (s, 1H), 5.32 (q, J=7.4 Hz, 1H), 2.20 (s, 3H). MS-ESI (m/z) 224.2 [M+1]$^+$, 206.2 (100%), 186.2, 178.2, 158.2.

D. Preparation of 3-hydroxy-2-methyl-17H-pyridin-4-one

A 500-mL high-pressure reaction vessel equipped with a magnetic stir bar and a thermometer was charged with maltol (20 g, 0.16 mol), ethanol (40 mL) and ammonium hydroxide solution (28.0-30.0%, 35 mL, 0.52 mol). The reaction vessel was sealed and heated at 66° C. for 2.5 h. HPLC analysis (HPLC Method 1, Example 24) indicated that only 26% of product (peak percent area) was formed. Another 30 mL of conc. ammonium hydroxide (28.0-30.0%, 0.45 mol) was added, and the resulting mixture was sealed and heated to 75° C. for overnight. Upon cooling, a solid separated, and it was collected by suction filtration (8.7 g). HPLC analysis of the solid indicated presence of the desired product and maltol in about 4/1 ratio. The solid was slurried in methanol (30 mL), and the resulting mixture was stirred. The solid 3-hydroxy-2-methyl-1H-pyridin-4-one was collected by suction filtration (4.8 g, 24% yield, HPLC purity (peak percent area): 99.7% at λ=280 nm). $^1$H NMR (DMSO-$d_6$) δ ppm: 11.6 (br s, 1H), 7.40 (d, J=6.8 Hz, 1H), 6.09 (d, J=6.8 Hz, 1H), 2.17 (s, 3H).

E. Preparation of 3-Hydroxy-2-methyl-S-(2,2,2-trifluoro-1-hydroxy-ethyl)-1Hpyridin-4-one A mixture of 3-hydroxy-2-methyl-1H-pyridin-4-one (6.1 g, 48.7 mmol), potassium carbonate (17 g, 123 mmol), and $CF_3CH(OH)OCF_3$ (25 mL, 0.25 mol) was heated to reflux under a blanket of nitrogen for 30 h. The progress of the reaction was monitored by HPLC Method 1 (Example 24), which indicated 63% (peak percent area) of conversion to the product. The reaction mixture was diluted with methanol (50 mL), then filtered to remove solid particulates. The filtrate was evaporated to dryness to afford an oil. The oily residue was taken up in ethyl acetate (150 mL) and washed with a saturated ammonium chloride solution (80 mL). The organic fraction was collected and set aside. The pH of the aqueous fraction was adjusted to 6 with a dilute hydrochloric acid solution, and the resulting aqueous solution was extracted with ethyl acetate (2×40 mL). All the organic fractions were combined, then washed with saturated ammonium chloride, dried over $Na_2SO_4$, filtered and then evaporated to dryness to give an oil. On trituration with ether, 3-hydroxy-2-methyl-5-(2,2,2-trifluoro-1-hydroxy-ethyl)-1H-pyridin-4-one separated as a solid product and was collected by suction filtration (3.5 g, 33%). NMR data is described in Part C above.

EXAMPLE 33

Preparation of 3-Benzyloxy-1,2-dimethyl-5-(2,2,2-trifluoro-1-hydroxy-ethyl)-1H-pyridin-4-one A mixture of 3-benzyloxy-2-methyl-5-(2,2,2-trifluoro-1-hydroxy-ethyl)-1H-pyridin-4-one (2.07 g, 6.6 mmol), acetonitrile (60 mL), potassium carbonate (2.62 g. 19 mmole) and methyl iodide (15 mL, 0.24 mol) was heated to reflux for 30 min. On cooling to RT, the reaction mixture was filtered over a pad of CELITE™, and the filtrate was concentrated in vacuo to give a solid. The solid was dissolved in dichloromethane, and the resulting solution was washed with brine, dried over $Na_2SO_4$, filtered and concentrated to afford 3-benzyloxy-1,2-dimethyl5-(2,2,2-trifluoro-1-hydroxy-ethyl)-1H-pyridin-4-one (1.48 g, 70% yield, HPLC Method 1 (Example 24), RT=15.4 min, HPLC purity (peak percent area): 99.9% at λ=280 nm). $^1$H NMR (DMSO-$d_6$+$D_2O$) δ ppm: 7.75 (s, 1H), 7.37, (m, 5H), 5.35 (q, J=7.1 Hz, 1H), 5.01 (m, 2H), 3.63 (s, 3H), 2.18 (s, 3H); MS-ESI (m/z) 328.1 [M+1]$^+$, 220.2, 91.2 (100%).

EXAMPLE 34

Preparation of 3-Hydroxy-1,2-dimethyl-5-(2,2,2-trifluoro-1-hydroxy-ethyl)-1H-pyridin-4-one 3-Benzyloxy-1,2-dimethyl-5-(2,2,2-trifluoro-1-hydroxy-ethyl)-1H-pyridin-4-one (0.97 g, 2.96 mmol) in methanol (30 mL) was debenzylated with Pd/C (10 wt. %, dry basis, on activated carbon, wet, Degussa type E101 NE/W, 0.15 g) as catalyst under a hydrogen atmosphere at 50 psi pressure. The reaction was completed in 10 min. The reaction mixture was diluted with methanol (30 mL), sonicated for 10 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was collected and concentrated in vacuo to give 3-hydroxy-1,2-dimethyl-5-(2,2,2-trifluoro-1-hydroxy-ethyl)-1H-pyridin-4-one as a solid product (0.43 g, 61% yield, HPLC Method 1 (Example 24), RT=9.4 min, HPLC purity (peak percent area): 99.8% at λ=280 nm). $^1$H NMR (DMSO-$d_6$) δ ppm: 7.72 (s, 1H), 5.34 (q, J=7.3 Hz, 1H), 3.71 (s, 3H), 2.27 (s, 3H); MS (m/z) 238.1 [M+1]$^+$, 220.2 (100%), 192.3, 172.1.

EXAMPLE 35

Preparation of 3-Hydroxy-1,2-dimethyl-5-(2,2,2-trifluoro-ethyl)-1H-pyridin-4-one

A. Preparation of 3-Benzyloxy-5-(1-chloro-2,2,2-trifluoro-ethyl)-2-methyl-1H-pyridin-4-one hydrochloric acid salt Thionyl chloride (7.5 mL, 102 mmol) was added to a suspension of 3-benzyloxy-2-methyl-5-(2,2,2-trifluoro-1-hydroxy-ethyl)-1H-pyridin-4-one (8.0 g, 25.5 mmol) in acetonitrile (100 mL) at room temperature. The resulting mixture was heated to 60° C. for 1 h. The progress of the reaction was monitored by TLC (methanol/dichloromethane 5/100 v/v as eluant). The reaction mixture (suspension) was evaporated to dryness to afford a solid. After stirring in acetonitrile, the title compound was collected by suction filtration (7.1 g, 75% yield). $^1$H NMR (DMSO-$d_6$+$D_2$O) δ ppm: 7.88 (s, 1H), 7.33 (m, 5H), 6.03 (q, J=7.3 Hz, 1H), 5.02 (s, 2H), 2.10 (s, 3H).

B. Preparation of 3-Benzyloxy-2-methyl-5-(2,2,2-trifluoro-ethyl)-1H-pyridin-4-one and 3-Benzyloxy-2-methyl-5-(2,2,2-trifluoro-1-methoxy-ethyl)-1H-pyridin-4-one To a clear solution of 3-benzyloxy-5-(1-chloro-2,2,2-trifluoro-ethyl)-2-methyl-1H-pyridin-4-one hydrochloric acid salt (2.03 g, 5.50 mmol) in methanol (70 mL) was added sodium borohydride (1.25 g, 33.0 mmol) in several portions. The reaction was completed within 20 min. The reaction mixture was quenched with deionized water (80 mL). The volume of the resulting clear solution was reduced to about 10 mL by evaporation under reduced pressure to give a solid/liquid mixture. Another 50 mL of deionized water was added. The aqueous solution was extracted with dichloromethane (3×50 mL). The combined organic fractions was dried over $Na_2SO_4$, filtered, then concentrated in vacuo to give an oil (1.3 g), which solidified upon standing. HPLC analysis (HPLC Method 1, Example 24) of the crude solid material indicated presence of a mixture of the desired compound 3-benzyloxy-2-methyl-5-(2,2,2-trifluoro-ethyl)-1H-pyridin-4-one (RT=14.7 min, peak percent area=80.6%) and 3-benzyloxy-2-methyl-5-(2,2,2-trifluoro-1-methoxy-ethyl)-1H-pyridin-4-one (RT=15.7 min, peak percent area=16.2%) in about 5/1 ratio. Purification of the solid by column chromatography on silica gel (methanol/dichloromethane 2/100 to 3/100 v/v as eluant) afforded the title compound (0.9 g, 56% yield, HPLC purity (peak percent area): 98% at λ=280 nm). $^1$H NMR (DMSO-$d_6$) δ ppm: 11.47 (br s, 1H), 7.60 (s, 1H), 7.37 (m, 5H), 5.06 (s, 2H), 3.41 (q, J=11.5 Hz, 2H), 2.06 (s, 3H); MS-ESI (m/z) 298.2 [M+1]$^+$, 91.1 (100%).

3-Benzyloxy-2-methyl-5-(2,2,2-trifluoro-1-methoxy-ethyl)-1H-pyridin-4-one was also isolated from the column (0.2 g, HPLC purity (peak percent area): 95% at λ=280 nm). $^1$H NMR (DMSO-$d_6$) δ ppm: 11.67 (br s, 1H), 7.50 (s, 1H), 7.35 (m, 5H), 5.22 (q, J=6.9 Hz, 1H), 5.08 (m, 2H), 2.09 (s, 3H); $^1$H NMR (DMSO-$d_6$+$D_2$O) δ ppm: 7.51 (s, 1H), 7.35 (m, 5H), 5.19 (q, J=6.8 Hz, 1H), 5.05 (m, 2H), 3.32 (s, 3H), 2.06 (s, 3H). MS-ESI (m/z) 328.2 [M+1]$^+$, 206.2, 91.1 (100%).

C. Preparation of 3-Hydroxy-1,2-dimethyl-5-(2,2,2-trifluoro-ethyl)-1H-pyridin-4-one Methyl iodide (11 mL, 176 mmol) was added to a suspension of 3-benzyloxy-2-methyl-5-(2,2,2-trifluoro-ethyl)-1H-pyridin-4-one (1.18 g, 4.0 mmol) and potassium carbonate (1.06 g, 7.7 mmol) in acetonitrile (25 mL). The resulting mixture was heated to reflux, and the reaction was completed within 40 min. The mixture was cooled to RT, and the solid particulates was filtered off. The filtrate was concentrated in vacuo to give a solid. The solid was taken up in dichloromethane, and the organic layer was washed with brine, dried over $Na_2SO_4$, filtered and concentrated in vacuo to afford 3-benzyloxy-1,2-dimethyl-5-(2,2,2-trifluoro-ethyl)-1H-pyridin-4-one as a colorless oil (1.3 g, 95% yield, HPLC Method 1 (Example 24), RT=15.9 min, HPLC purity (peak percent area): 98% at λ=280 nm).

A clear solution of 3-benzyloxy-1,2-dimethyl-5-(2,2,2-trifluoro-ethyl)-1H-pyridin-4-one (1.1 g, 3.53 mmol) in methanol (32 mL) was debenzylated using Pd/C (10 wt. %, dry basis, on activated carbon, wet, Degussa type E101 NE/W, 0.17 g) as catalyst in a hydrogen atmosphere at a pressure of 50 psi for 30 min. The reaction mixture was diluted with methanol (30 mL), and sonicated for 10 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The volume of the filtrate was reduced to about 20 mL by evaporation under reduced pressure. HPLC analysis (HPLC Method 1, Example 24) of the filtrate indicated the presence of about 42% (peak percent area) of the starting material. Another 150 mg of Pd/C was added, and the mixture was subjected to the debenzylation reaction condition for a further 20 min, and worked up as described above. The catalyst was filtered off, and the filtrate was evaporated to dryness to afford 3-hydroxy-1,2-dimethyl-5-(2,2,2-trifluoro-ethyl)-1H-pyridin-4-one as a solid product (0.54 g, 69% yield, HPLC Method 1 (Example 24), RT=9.9 min, HPLC purity (peak percent area): 99.3% at λ=280 nm). $^1$H NMR (DMSO-$d_5$) δ ppm: 7.70 (s, 1H), 3.65 (s, 3H), 3.39 (q, J=11.5 Hz, 2H), 2.26 (s, 3H). MS-ESI (m/z) 222.2 ([M+1]$^+$, 100%), 202.2, 182.2.

EXAMPLE 36

Preparation of 3-Hydroxy-2-methyl-5-(2,2,2-trifluoro-ethyl)-1H-pyridin-4-one

In a similar manner as described in Example 35C, the debenzylation of a clear solution of 3-benzyloxy-2-methyl-5-(2,2,2-trifluoro-ethyl)-1H-pyridin-4-one (0.60 g, 2.02 mmol) in methanol (25 mL) using Pd/C (10 wt. %, dry basis, on activated carbon, wet, Degussa type E101 NE/W, 93 mg) as catalyst under a hydrogen atmosphere at a pressure of 50 psi afforded, after work up as described above, the title compound 3-hydroxy-2-methyl-5-(2,2,2-trifluoro-ethyl)-1H-pyridin-4-one as a solid product (0.29 g, 71% yield, HPLC Method 1 (Example 24), RT=8.4 min, HPLC purity (peak percent area): 99.6% at λ=280 nm). $^1$H NMR (DMSO-$d_6$) δ ppm: 7.51 (s, 1H), 3.41 (q, J=11.7 Hz, 2H), 2.18 (s, 3H); MS-ESI (m/z) 207.9 [M+1]$^+$, 188.2 (100%), 168.2.

EXAMPLE 37

Preparation of 3-Hydroxy-2-methyl-5-(2,2,2-trifluoro-1-methoxy-ethyl)-1H-pyridin-4-one A clear solution of 3-benzyloxy-2-methyl-5-(2,2,2-trifluoro-1-methoxy-ethyl)-1H-pyridin-4-one (609 mg, 1.86 mmol) in methanol (32 mL) was debenzylated using Pd/C (10 wt. %, dry basis, on activated carbon, wet, Degussa type E101 NE/W, 154 mg) as catalyst under a hydrogen atmosphere at 50 psi of pressure. The reaction was completed in 55 min. The mixture was diluted with methanol (50 mL), sonicated for 10 min. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was collected and concentrated in vacuo to give 3-hydroxy-2-methyl-5-(2,2,2-trifluoro-1-methoxy-ethyl)-1H-pyridin-4-one as a solid product (0.27 g, 61% yield, HPLC Method 1 (Example 24), RT=9.7 min, purity (peak percent area): 99.3% at λ=280 nm). $^1$H NMR (DMSO-d$_6$) δ ppm: 7.42 (s, 1H), 5.19 (q, J=7.0 Hz, 1H), 3.32 (s, 3H), 2.20 (s, 3H); MS-ESI (m/z) 238.1 [M+1]$^+$, 206.2 (100%), 186.1, 178.2, 158.2.

EXAMPLE 38

Preparation of 3-hydroxy-6-methyl-2-(2,2,2-trifluoro-1-hydroxy-ethyl)-1H-pyridin-4-one A. Preparation of 5-benzyloxy-2-methyl-1H-pyridin-4-one A mixture of 3-benzyloxy-6-methyl-4-oxo-1,4-dihydropyridine-2-carboxylic acid (5.2 g, 20.0 mmol) in dimethylformamide (12 mL) was heated in an oil bath for 8 h. The temperature of the oil bath was maintained at 120° C. A solid separated upon cooling to RT. The solid 5-benzyloxy-2-methyl-1H-pyridin-4-one was suction filtered and washed with hexane. The isolated solid was dried under high vacuum for 16 h (3.32 g, 77% yield). $^1$H NMR (400 MHz, MeOH-D$_4$) δ (ppm): 7.45-7.46 (m, overlapping peaks, 2H, Ar—H and CH), 7.29-7.39 (m, overlapping peaks, 4H, Ar—H), 6.34 (s, 1H, CH), 5.07 (s, 2H, OCH$_2$), 2.30 (s, 3H, CH$_3$); MS-ESI (m/z): 216.3 [M+1]$^+$, 215.6 [M]$^+$, 188.3.

B. Preparation of 5-hydroxy-2-methyl-1H-pyridin-4-one hydrochloride

5-Benzyloxy-2-methyl-1H-pyridin-4-one (15.5 g, 72.0 mmol) was mixed with 10% Pd/C (1.60 g) in methanol (200 mL) and water (35 mL) in a Parr hydrogenator bottle. The mixture was hydrogenated on a Parr hydrogenator for 45 minutes at 50 psi hydrogen pressure. 6N HCl (12 mL) was added. A CELITE™ bed was prepared on a sintered glass, and washed with 6M HCl (100 mL), followed by water (7×50 mL) and then methanol (2×50 mL) under suction. The reaction mixture was filtered through the pre-treated CELITE™ bed. The filtrate was evaporated to dryness and the residue was triturated with acetone, then filtered to give 5-hydroxy-2-methyl-1H-pyridin-4-one hydrochloride 9.30 g as off-white solid. The mother liquor was diluted with hexane and placed at room temperature over night to give an additional 1.63 g of product. Thus, 10.9 g of the title compound was obtained (94% yield). $^1$H NMR (90 MHz, MeOD) δ (ppm) 7.93 (s, 1H, CH), 7.07 (s, 1H, CH) 2.56 (s, 3H, CH$_3$). MS-ESI (m/z): 126.1 [M+1]$^+$, 108.2, 110.1.

C. Preparation of 3-hydroxy-6-methyl-2-(2,2,2-trifluoro-1-hydroxy-ethyl)-1H-pyridin-4-one 5-Hydroxy-2-methyl-1H-pyridin-4-one hydrochloride (1.00 g, 6.19 mmol) and potassium carbonate (1.02 g, 7.42 mmol) was mixed together in water (10 mL) at room temperature, and stirred until evolution of carbon dioxide ceased. Then, 2,2,2-trifluoro-1-methoxy-ethanol (1.60 g, 12.4 mmol) was added. The reaction mixture was heated in a sealed flask at 100.degree. C. for 20 h. The mixture was cooled down to RT and neutralized with acetic acid to pH at between 5 to 6. The precipitate was collected by suction filtration and washed with water and ether. Thus, 3-hydroxy-6-methyl-2-(2,2,2-trifluoro-1-hydroxy-ethyl)-1H-pyridin-4-one was obtained as an off-white solid (1.06 g, 76% yield). $^1$H NMR (90 MHz, DMSO-d$_6$) δ (ppm): 6.09 (s, 1H, CH); 5.42 (apparent q, 1H, CH), 2.28 (s, 3H, CH$_3$); MS-ESI (m/z) 224.1 [M+1]$^+$, 206.1, 186.1, 178.1.

Although preferred embodiments of the present invention have been described herein, it will be understood by those skilled in the art that variations may be made thereto without departing from the spirit of the invention or the scope of the appended claims.

The invention claimed is:

1. A method of treating a neurodegenerative disease in a patient wherein the method comprises administering to the patient an effective amount of a compound of formula (I)

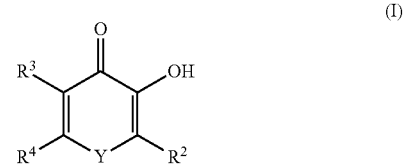

(I)

or a pharmaceutically acceptable salt thereof, selected from the group consisting of:

(a) a compound of formula (II):

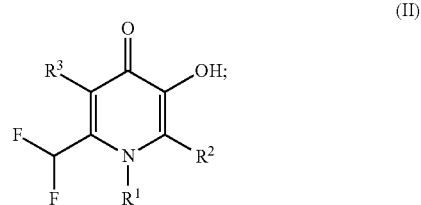

(II)

(b) a compound of formula (III):

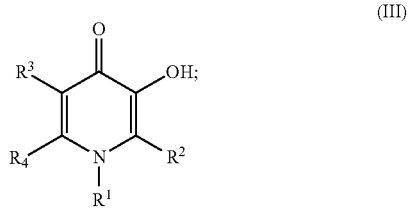

(III)

(c) a compound of formula (IIIC):

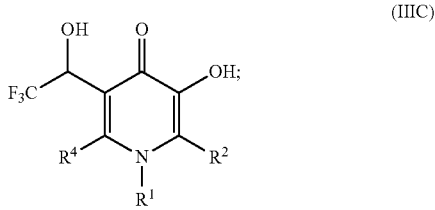

(IIIC)

and (d) a compound of formula (IV):

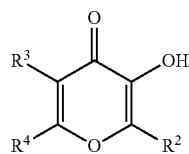

wherein in formula I:
Y is O or $NR^1$,
$R^1$ is selected from the group consisting of: hydrogen, $C_1$-$C_6$ alkyl, cyclopropylmethyl, allyl and cyclopropyl;
$R^2$ is selected from the group consisting of: hydrogen, $C_1$-$C_6$ alkyl, $CHF_2$, $CH_2CF_3$, $CF_3CHOH$ and $R^5CHOH$, $R^5$ is selected from the group consisting of: hydrogen, $C_1$-$C_6$ alkyl and trifluoromethyl;
$R^3$ is selected from the group consisting of: methyl, hydrogen, $CF_3CHOH$, $C_1$-$C_6$ alkyl, $CH_2CF_3$, and $CH(OCH_3)CF_3$ and
$R^4$ is selected from the group consisting of: $CHF_2$, methyl, hydrogen, $C_1$-$C_6$ alkyl, $CH_2CF_3$, and $CF_3CHOH$;
provided that
(a) when the compound of formula (I) is a compound of formula (II), then
Y is $NR^1$, wherein $R^1$ is selected from the group consisting of hydrogen, $C_1$-$C_6$ alkyl, cyclopropylmethyl, allyl and cyclopropyl;
$R^2$ is selected from the group consisting of hydrogen, $C_1$-$C_4$ alkyl, and $R^5CHOH$ wherein $R^5$ is selected from the group consisting of hydrogen, $C_1$-$C_3$ alkyl and trifluoromethyl;
$R^3$ is selected from the group consisting of methyl, hydrogen and $CF_3CHOH$; and
$R^4$ is $CHF_2$;
and
(b) when the compound of formula (I) is a compound of formula (III), then:
Y is $NR^1$, wherein $R^1$ is defined as above;
$R^2$ is selected from the group consisting of $CHF_2$, $CH_2CF_3$, and $CF_3CHOH$; and
$R^3$ and $R^4$ are each selected from the group consisting of methyl and hydrogen;
and
(c) when the compound of formula (I) is a compound of formula (IIIC), then:
Y is $NR^1$ and $R^1$ is defined as above;
$R^2$ is selected from the group consisting of hydrogen and $C_1$-$C_6$ alkyl, with the proviso that when $R^4$ is hydrogen, $R^2$ is not hydrogen;
$R^3$ is $CF_3CHOH$; and
$R^4$ is selected from the group consisting of hydrogen and methyl;
and
(d) when the compound of formula (I) is a compound of formula (IV), then:
Y is O;
$R^2$ is $CF_3CHOH$;
$R^3$ is selected from the group consisting of methyl and hydrogen; and
$R^4$ is selected from the group consisting of hydrogen and $C_1$-$C_6$ alkyl;

or
Y is O;
$R^2$ is hydrogen;
$R^3$ is hydrogen; and
$R^4$ is difluoromethyl;
or:
Y is $NR^1$, wherein $R^1$ is defined as above;
$R^2$ is selected from the group consisting of hydrogen, $C_1$-$C_6$ alkyl, and $R_5CHOH$, wherein $R^5$ is selected from the group consisting of hydrogen, $C_1$-$C_6$ alkyl and trifluoromethyl;
$R^3$ is hydrogen, methyl, $C_1$-$C_6$ alkyl; and
$R^4$ is $CH_2CF_3$, and $CF_3CHOH$;
or
Y is $NR^1$, wherein $R^1$ is defined as above;
$R^2$ is selected from the group consisting of hydrogen, $C_1$-$C_6$ alkyl, and $R_5CHOH$, wherein $R^5$ is selected from the group consisting of hydrogen, $C_1$-$C_6$ alkyl and trifluoromethyl;
$R^3$ is $CH_2CF_3$, $CH(OCH_3)CF_3$; and
$R^4$ is hydrogen, methyl, $C_1$-$C_6$ alkyl.

2. The method of claim 1 wherein the neurodegenerative disease is caused by the presence of free iron or iron accumulation in neural tissues.

3. The method of claim 2 wherein the neurodegenerative disease is selected from the group consisting of Parkinson's disease and Alzheimer's disease.

4. A method of treating an iron overload disease in a patient wherein the method comprises administering to the patient an effective amount of a compound of formula (I)

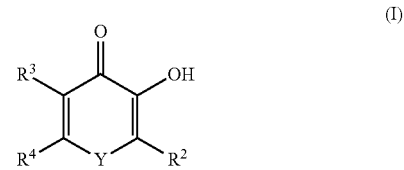

or a pharmaceutically acceptable salt thereof, selected from the group consisting of:
(a) a compound of formula (II):

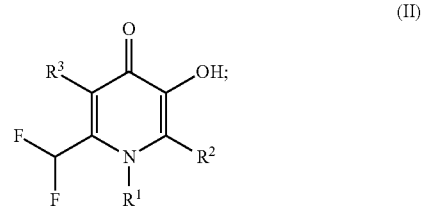

(b) a compound of formula (III):

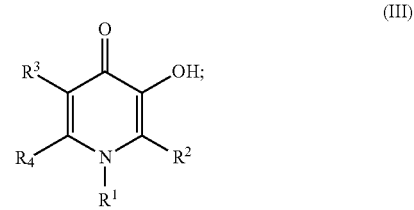

(c) a compound of formula (IIIC):

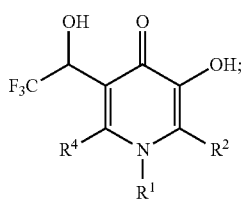

and
(d) a compound of formula (IV):

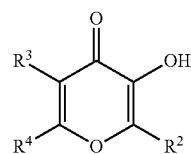

wherein in formula I:
Y is O or $NR^1$,
$R^1$ is selected from the group consisting of: hydrogen, $C_1$-$C_6$ alkyl, cyclopropylmethyl, allyl and cyclopropyl;
$R^2$ is selected from the group consisting of: hydrogen, $C_1$-$C_6$ alkyl, $CHF_2$, $CH_2CF_3$, $CF_3CHOH$ and $R^5CHOH$, $R^5$ is selected from the group consisting of: hydrogen, $C_1$-$C_6$ alkyl and trifluoromethyl;
$R^3$ is selected from the group consisting of: methyl, hydrogen, $CF_3CHOH$, $C_1$-$C_6$ alkyl, $CH_2CF_3$, and $CH(OCH_3)CF_3$ and
$R^4$ is selected from the group consisting of: $CHF_2$, methyl, hydrogen, $C_1$-$C_6$ alkyl, $CH_2CF_3$, and $CF_3CHOH$;
provided that
(a) when the compound of formula (I) is a compound of formula (II), then
Y is $NR^1$, wherein $R^1$ is selected from the group consisting of hydrogen, $C_1$-$C_6$ alkyl, cyclopropylmethyl, allyl and cyclopropyl;
$R^2$ is selected from the group consisting of hydrogen, $C_1$-$C_4$ alkyl, and $R^5CHOH$ wherein $R^5$ is selected from the group consisting of hydrogen, $C_1$-$C_3$ alkyl and trifluoromethyl;
$R^3$ is selected from the group consisting of methyl, hydrogen and $CF_3CHOH$; and
$R^4$ is $CHF_2$;

and
(b) when the compound of formula (I) is a compound of formula (III), then:
Y is $NR^1$, wherein $R^1$ is defined as above;
$R^2$ is selected from the group consisting of $CHF_2$, $CH_2CF_3$ and $CF_3CHOH$; and
$R^3$ and $R^4$ are each selected from the group consisting of methyl and hydrogen;
and
(c) when the compound of formula (I) is a compound of formula (IIIC), then:
Y is $NR^1$ and $R^1$ is defined as above;
$R^2$ is selected from the group consisting of hydrogen and $C_1$-$C_6$ alkyl, with the proviso that when $R^4$ is hydrogen, $R^2$ is not hydrogen;
$R^3$ is $CF_3CHOH$; and
$R^4$ is selected from the group consisting of hydrogen and methyl;
and
(d) when the compound of formula (I) is a compound of formula (IV), then:
Y is O;
$R^2$ is $CF_3CHOH$;
$R^3$ is selected from the group consisting of methyl and hydrogen; and
$R^4$ is selected from the group consisting of hydrogen and $C_1$-$C_6$ alkyl;
or
Y is O;
$R^2$ is hydrogen;
$R^3$ is hydrogen; and
$R^4$ is difluoromethyl;
or:
Y is $NR^1$, wherein $R^1$ is defined as above;
$R^2$ is selected from the group consisting of hydrogen, $C_1$-$C_6$ alkyl, and $R_5CHOH$, wherein $R^5$ is selected from the group consisting of hydrogen, $C_1$-$C_6$ alkyl and trifluoromethyl;
$R^3$ is hydrogen, methyl, $C_1$-$C_6$ alkyl; and
$R^4$ is $CH_2CF_3$, and $CF_3CHOH$;
or
Y is $NR^1$, wherein $R^1$ is defined as above;
$R^2$ is selected from the group consisting of hydrogen, $C_1$-$C_6$ alkyl, and $R_5CHOH$, wherein $R^5$ is selected from the group consisting of hydrogen, $C_1$-$C_6$ alkyl and trifluoromethyl;
$R^3$ is $CH_2CF_3$, $CH(OCH_3)CF_3$; and
$R^4$ is hydrogen, methyl, $C_1$-$C_6$ alkyl.

5. The method of claim 4 wherein the iron overload disease is selected from the group consisting of β-thalassemia, Friedreich's ataxia and Hallervorden-Spatz syndrome.

* * * * *